(12) United States Patent
Barrow et al.

(10) Patent No.: US 7,847,100 B2
(45) Date of Patent: Dec. 7, 2010

(54) 1,3,5-SUBSTITUTED PHENYL DERIVATIVE COMPOUNDS USEFUL AS BETA-SECRETASE INHIBITORS FOR THE TREATMENT OF ALZHEIMER'S DISEASE

(75) Inventors: James C. Barrow, Harleysville, PA (US); Georgia B. McGaughey, Harleysville, PA (US); Philippe G. Nantermet, Landale, PA (US); Hemaka A. Rajapakse, Wyncote, PA (US); Harold G. Selnick, Ambler, PA (US); Shaun R. Stauffer, Schwenksville, PA (US); Craig A. Coburn, Royersford, PA (US)

(73) Assignee: Merck, Sharp & Dohme, Inc., Rahway, NJ (US)

( * ) Notice: Subject to any disclaimer, the term of this patent is extended or adjusted under 35 U.S.C. 154(b) by 1064 days.

(21) Appl. No.: 11/578,559

(22) PCT Filed: Apr. 15, 2005

(86) PCT No.: PCT/US2005/012973

§ 371 (c)(1),
(2), (4) Date: Oct. 10, 2006

(87) PCT Pub. No.: WO2005/103020

PCT Pub. Date: Nov. 3, 2005

(65) Prior Publication Data

US 2007/0244119 A1   Oct. 18, 2007

Related U.S. Application Data

(60) Provisional application No. 60/563,657, filed on Apr. 20, 2004.

(51) Int. Cl.
*A61K 31/4245* (2006.01)
*C07D 271/10* (2006.01)
*C07D 271/06* (2006.01)

(52) U.S. Cl. .................. 548/131; 548/143; 514/364
(58) Field of Classification Search ............... 548/131, 548/143
See application file for complete search history.

(56) References Cited

U.S. PATENT DOCUMENTS

| 7,109,217 B2 | 9/2006 | Coburn et al. |
| 2006/0058278 A1 | 3/2006 | Coburn et al. |
| 2006/0149092 A1 | 7/2006 | Nantermet et al. |
| 2006/0161020 A1 | 7/2006 | Coburn et al. |

FOREIGN PATENT DOCUMENTS

| WO | WO 03/057721 | 7/2003 |
| WO | WO 03/072535 | 9/2003 |
| WO | WO 03/106405 | 12/2003 |
| WO | WO 2004/050619 | 6/2004 |
| WO | WO 2005/005374 | 1/2005 |
| WO | WO 2005/018545 | 3/2005 |
| WO | WO 2005/032471 | 4/2005 |
| WO | WO 2005/051914 | 6/2005 |
| WO | WO 2005/065195 | 7/2005 |
| WO | WO 2005/097767 | 10/2005 |
| WO | WO 2005/103043 | 11/2005 |

OTHER PUBLICATIONS

J. Lloyd et al., "Design and Synthesis of 4-Substituted Benzamides as Potent, Selective, and Orally Bioavailable . . . ," J. med. Chem., vol. 44, pp. 3764-3767 (2001).
C. Coburn et al., "Identification of a Small Molecule Nonpeptide Active Site Beta-Secretase Inhibitors . . . ,", J. Med. Chem., vol. 47, pp. 6117-6119 (2004).
S. Stachel et al., "Structure-Based design of Potent and Selective Cell-Permeable Inhibitors of Human Beta-Secretase (BACE-1)," J. Med. Chem., vol. 47, pp. 6447-6450 (2004).
S. Stachel et al., "Conformationally biased P3 amide replacements of B-secretase inhibitors," Biorganic & Medicinal Chemistry Letters, vol. 16, pp. 641-644 (2006).

*Primary Examiner*—Laura L. Stockton
(74) *Attorney, Agent, or Firm*—Keith D. MacMillan; John C. Todaro

(57) ABSTRACT

The present invention is directed to 1,3,5-phenyl substituted derivative compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

11 Claims, No Drawings

1,3,5-SUBSTITUTED PHENYL DERIVATIVE COMPOUNDS USEFUL AS BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) from U.S. provisional application Ser. No. 60/563,657, filed Apr. 20, 2004.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to a class of novel 1,3,5-substituted phenyl derivative compounds which are useful as inhibitors of the β-secretase enzyme, and to the treatment of diseases in which the β-secretase enzyme is involved, such as Alzheimer's Disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a function of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to 1,3,5-substituted phenyl derivative compounds useful as inhibitors of the β-secretase enzyme, and useful in the treatment of diseases in which the β-secretase enzyme is involved, such as Alzheimer's disease. The invention is also directed to pharmaceutical compositions comprising these compounds, and the use of these compounds and compositions in the treatment of diseases in which the β-secretase enzyme is involved.

DETAILED DESCRIPTION OF THE INVENTION

The present invention is directed to compounds of formula (I):

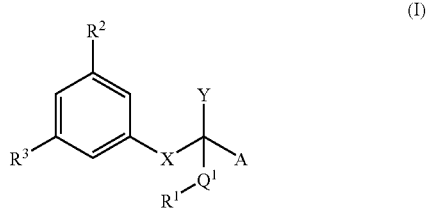

wherein:

X is selected from the group consisting of

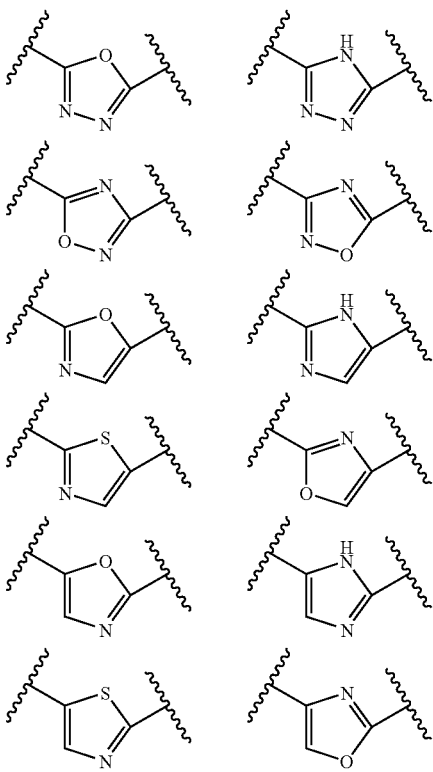

-continued

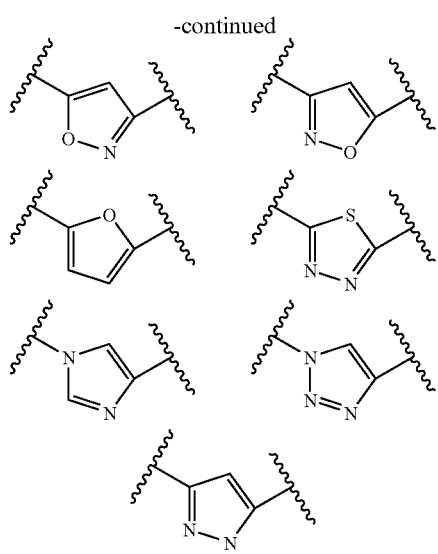

A is selected from the group consisting of
(1) hydrogen,
(2) —$C_{1-10}$ alkyl, and
(3) —$C_{2-10}$ alkenyl,
wherein said alkyl or alkenyl is unsubstituted or substituted with one or more
  (a) halo,
  (b) —$C_{3-12}$ cycloalkyl,
  (c) —OH,
  (d) —CN,
  (e) —O—$C_{1-10}$ alkyl,
  (f) phenyl, or
  (g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
  and said phenyl and heteroaryl is unsubstituted or substituted with one or more
    (i) halo,
    (ii) —OH,
    (iii) —CN,
    (iv) —O—$C_{1-10}$ alkyl,
    (v) —$C_{1-10}$ alkyl, or
    (vi) —$C_{3-12}$ cycloalkyl;
Y is selected from the group consisting of
(1) —OH, and
(2) —$NR^hR^i$,
wherein $R^h$ and $R^i$ are selected from the group consisting of
  (a) hydrogen,
  (b) —$C_{1-10}$ alkyl, or
  (c) $C_{0-6}$ alkyl-$C_{6-10}$ aryl,
or when Y is $NR^hR^i$, and $R^h$ is hydrogen, then $R^i$ and A may be linked together to form the group —$CH_2(CH_2)_qCH_2$—;
$Q^1$ is $C_{0-3}$ alkyl;
$R^1$ is
  (1) aryl selected from the group consisting of phenyl and napthyl, or
  (2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
(3) —$C_{1-10}$ alkyl,
(4) —$C_{3-8}$ cycloalkyl, said cycloalkyl optionally fused to a $C_{6-10}$ aryl group,
wherein said alkyl, cycloalkyl, aryl or heteroaryl is unsubstituted or substituted with one or more
  (a) halo,
  (b) —$C_{1-10}$ alkyl, wherein said alkyl is unsubstituted or substituted with one or more halo,
  (c) —OH,
  (d) —CN,
  (e) —O—$C_{1-10}$ alkyl, or
  (f) —$C_{3-12}$ cycloalkyl;
$R^2$ is selected from the group consisting of:
(1) ($R^4$—$SO_2$)$N(R^7)$—, wherein $R^4$ is selected from the group consisting of
  (a) —$C_{1-10}$ alkyl, or
  (b) —$C_{3-12}$ cycloalkyl,
  wherein said alkyl and cycloalkyl is unsubstituted or substituted with one or more
    (i) halo,
    (ii) —OH,
    (iii) —CN,
    (iv) —O—$C_{1-10}$ alkyl,
    (v) —$C_{1-10}$ alkyl,
    (v) —$C_{3-12}$ cycloalkyl,
    (vi) aryl selected from the group consisting of phenyl and napthyl, or
    (vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
    and said aryl and heteroaryl is unsubstituted or substituted with one or more
      (A) halo,
      (B) —OH,
      (C) —CN,
      (D) —O—$C_{1-10}$ alkyl,
      (E) —$C_{3-12}$ cycloalkyl, or
      (F) —$C_{1-10}$ alkyl; and
$R^7$ is selected from the group consisting of
  (a) hydrogen,
  (b) —$C_{1-10}$ alkyl,
  (c) aryl selected from the group consisting of phenyl and napthyl,
  (d) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
  wherein said alkyl, aryl and heteroaryl is unsubstituted or substituted with one or more
    (i) halo,
    (ii) —OH,
    (iii) —CN,
    (iv) —O—$C_{1-10}$ alkyl,
    (v) —$C_{3-12}$ cycloalkyl,
    (vi) aryl selected from the group consisting of phenyl and napthyl, or (vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl, wherein said alkyl, cycloalkyl, aryl or heteroaryl is unsubstituted or substituted with one or more
(A) halo,
(B) —OH,
(C) —CN,
(D) —O—$C_{1-10}$ alkyl,
(E) —$C_{3-12}$ cycloalkyl, or
(F) aryl selected from the group consisting of phenyl and napthyl;

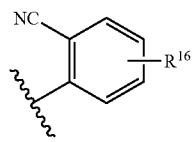
(2)

wherein $R^{16}$ is selected from the group consisting of
(1) hydrogen,
(2) halogen,
(3) $SR^j$,
(4) $SO_2R^j$,
(5) $NR^kR^m$, wherein $R^j$, $R^k$ and $R^m$ are selected from the group consisting of
(a) hydrogen,

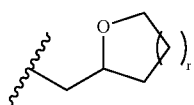
(b)

(c) —$C_{1-10}$ alkyl,
(d) —$C_{2-10}$ alkenyl,
(e) —$C_{2-10}$ alkynyl, and
(f) aryl selected from the group consisting of phenyl and napthyl, wherein said alkyl, alkenyl, alkynyl, and
aryl is unsubstituted or substituted with one or more
(i) halo,
(ii) —OH,
(iii) —CN,
(iv) —O—$C_{1-10}$ alkyl,
(v) —$C_{3-12}$ cycloalkyl,
(vi) aryl selected from the group consisting of phenyl and napthyl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl, or when $R^{16}$ is $NR^jR^k$, then $R^j$ and $R^k$ may be linked together to form a 4-6 membered carbocyclic ring, wherein one or more of the ring carbon atoms may be replaced with an N, O or S atom, or an $SO_2$ group;

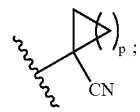
(3)

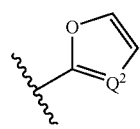
(4)

wherein $Q^2$ is selected from the group consisting of
(1) N, and
(2) C—$R^c$, wherein $R^c$ is selected from the group consisting of
(a) —CN, and
(b) —C(=O)—O—$C_{1-10}$ alkyl,
(b) —C(=O)—OH, and
(c) —C(=O)—$NR^dR^e$,
(d) —$NR^dR^e$, wherein $R^d$ and $R^e$ are selected from the group consisting of
(i) hydrogen, and
(ii) —$C_{1-10}$ alkyl,
(5) hydrogen; and
(6) —$CF_3$;

$R^3$ is selected from the group consisting of

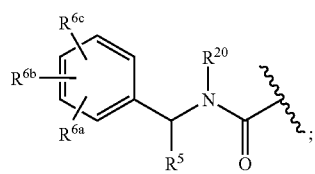
(1)

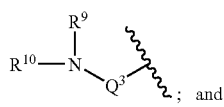
(2)
; and

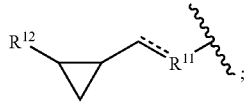
(3)

(4)

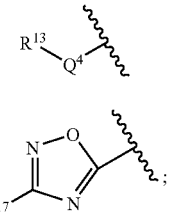
(5)

-continued (6)
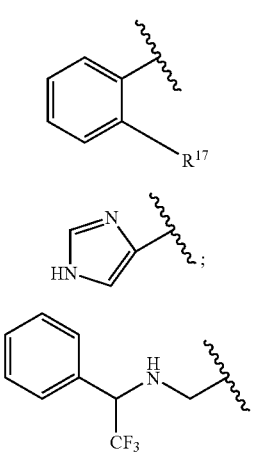

(7)

(8)

wherein $R^5$ is $C_{1-10}$ alkyl, wherein said alkyl is unsubstituted or substituted with one or more halogen;
$Q^3$ is selected from the group consisting of
(1) —C(═O)—, and
(2) a bond;
$Q^4$ is selected from the group consisting of
(1) —C(═O)—,
(2) —CH$_2$—O—, and
(3) a bond;
$R^{6a}$, $R^{6b}$, and $R^{6c}$ are independently selected from the group consisting of:
(1) hydrogen,
(2) halo,
(3) —C$_{1-10}$ alkyl,
(4) —OH,
(5) —CN,
(6) —C$_{3-12}$ cycloalkyl, and
(7) —O—C$_{1-10}$ alkyl;
$R^9$ and $R^{10}$ are independently selected from the group consisting of
(1) hydrogen,
(2) —C$_{1-10}$ alkyl,
(3) —C$_{2-10}$ alkenyl,
(4) —C$_{2-10}$ alkynyl, and
(5) —C$_{1-10}$ alkyl-C$_{3-12}$ cycloalkyl;
wherein said alkyl, alkenyl, alkynyl and cycloalkyl is unsubstituted or substituted with one or more
(a) halo,
(b) —OH,
(c) —CN,
(d) —C$_{1-10}$ alkyl,
(e) —O—C$_{1-10}$ alkyl,
(f) —C$_{3-8}$ cycloalkyl,
(g) —NR$^f$R$^g$, wherein R$^f$ and R$^g$ are selected from the group consisting of
(i) hydrogen, and
(ii) —C$_{1-10}$ alkyl, or R$^f$ and R$^g$ are joined together with the nitrogen atom to which they are attached to form a 4-6 membered ring, or
(h) aryl selected from the group consisting of phenyl and napthyl;
or $R^9$ and $R^{10}$ are joined together with the nitrogen atom to which they are attached to form a 4-6 membered ring, which is unsubstituted or substituted with one or more (1) $C_{1-10}$ alkyl, wherein said alkyl is unsubstituted or substituted with one or more
(i) halogen,
(ii) hydroxy, or
(iii) —C$_{1-6}$ alkoxy;
(2) —C$_{3-12}$ cycloalkyl,
(3) (CH$_2$)$_n$-phenyl, wherein said phenyl is unsubstituted or substituted with or more halogen,
(4) C$_{2-10}$ alkenyl,
(5) C$_{2-10}$ alkynyl,
(6) —CN, (7)
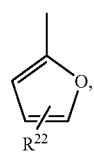

wherein $R^{22}$ is selected from the group consisting of
(a) hydrogen, and
(b) halogen, (8)
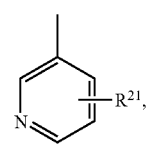

wherein $R^{21}$ is selected from the group consisting of
(a) hydrogen,
(b) halogen, and
(c) —C$_{1-10}$ alkyl, wherein said alkyl is unsubstituted or substituted with one or more
(i) halogen,
(ii) hydroxy, or
(iii) —C$_{1-6}$ alkoxy, or
(d) aryl selected from the group consisting of phenyl and napthyl;
and said alkyl, alkenyl or alkynyl $R^9$ and $R^{10}$ groups are unsubstituted or substituted with one or more
(a) halo,
(b) —OH,
(c) —CN,
(d) —O—C$_{1-10}$ alkyl, or
(e) —C$_{3-12}$ cycloalkyl;
and said cycloalkyl and phenyl $R^9$ and $R^{10}$ groups are unsubstituted or substituted with one or more
(a) halo,
(b) —C$_{1-10}$ alkyl,
(c) —OH,
(d) —CN,
(e) —C$_{3-12}$ cycloalkyl, or
(f) —O—C$_{1-10}$ alkyl;
$R^{11}$ is selected from the group consisting of
(1) —CH—,
(2) —CH$_2$—,

(4) —O—, and
(5) —NR⁸—, provided that when $R^{11}$ is —CH— the dotted line forms a bond and when $R^{11}$ is —CH₂—, —C(=O)—, —O— or —NR⁸— the dotted line is absent;

$R^8$ is hydrogen or $C_{1-10}$ alkyl, wherein said $C_{1-10}$ alkyl is unsubstituted or substituted with one or more
  (1) halo,
  (2) —OH,
  (3) —CN,
  (4) —$C_{3-12}$ cycloalkyl,
  (5) —O—$C_{1-10}$ alkyl;

$R^{12}$ is selected from the group consisting of
  (1) hydrogen,
  (2) —$C_{1-10}$ alkyl;
  (3) halo,
  (4) —$C_{3-12}$ cycloalkyl,
  (5) aryl selected from the group consisting of phenyl and napthyl, and
  (6) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
  wherein said aryl and heteroaryl is unsubstituted or substituted with one or more
    (a) halo,
    (b) —OH,
    (c) —CN,
    (d) —O—$C_{1-10}$ alkyl,
    (e) —$C_{3-8}$ cycloalkyl, or
    (f) —$C_{1-10}$ alkyl;

$R^{13}$ is selected from the group consisting of
  (1) aryl selected from the group consisting of phenyl and napthyl,
  (2) —$C_{1-10}$ alkyl,
  (3) —$C_{1-10}$ alkoxy,
  (4) —$C_{3-12}$ cycloalkyl,
  (5) —$C_{2-10}$ alkenyl,
  (6) —$C_{2-10}$ alkynyl, or
  (7) hydroxyl;

$R^{17}$ is selected from the group consisting of
  (1) —CN,
  (2) —$C_{1-10}$ alkyl, wherein said alkyl is unsubstituted or substituted with one or more
    (i) halogen,
    (ii) hydroxy,
    (iii) —$C_{1-6}$ alkoxy;
  (3) —$C_{0-10}$ alkyl —$NR^{18}R^{19}$, wherein $R^{18}$ and $R^{19}$ are selected from the group consisting of
    (i) hydrogen,
    (ii) —$C_{1-10}$ alkyl, or
    (iii) —C(=O)—$C_{1-10}$ alkyl, wherein alkyl is unsubstituted or substituted with one or more halogen, $R^{20}$ is selected from the group consisting of
  (1) hydrogen, and
  (2) $C_{1-10}$ alkyl;

n is 0, 1, 2, 3 or 4;
p is 1, 2, 3 or 4;
q is 0, 1 or 2;
r is 1 or 2;

and pharmaceutically acceptable salts thereof, and individual enantiomers and diastereomers thereof.

In one embodiment, the invention is directed to compounds of formula (I) wherein $R^1$ is phenyl and $Q^1$ is $CH_2$.

In another embodiment, the invention is directed to compounds of formula (I) wherein Y is $NH_2$.

In another embodiment of compounds of formula (I), Y is OH.

In another embodiment of the compounds of formula (I), A is $C_{1-10}$ alkyl, preferably $C_{1-6}$ alkyl, more preferably methyl.

In another embodiment of the compounds of formula (I), $R^2$ is —($R^4$)$NSO_2R^7$, and $R^4$ and $R^7$ are $C_{1-10}$ alkyl, preferably $C_{1-6}$ alkyl. More preferably, $R^4$ is methyl or isopropyl and $R^7$ is methyl or propyl.

In another embodiment of the compounds of formula (I), $R^2$ is the group

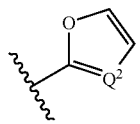

wherein $Q^2$ is selected from the group consisting of
  (1) N, and
  (2) C—$R^c$.

In another embodiment of the compounds of formula (I), $R^3$ is selected from the group of paragraphs (1) to (4) above.

In another embodiment of the compounds of formula (I), X is an oxadiazole selected from the group consisting of

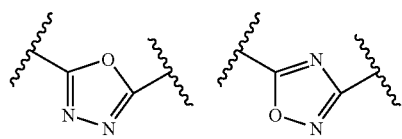

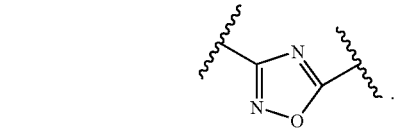

In another embodiment of the compounds of formula (I), X is an oxazole selected from

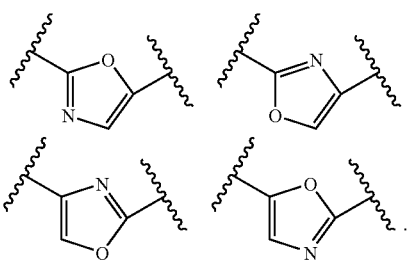

In another embodiment of the compounds of formula (I), X is a furan, as shown below

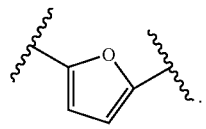

In another embodiment, the invention is directed to compounds of formula (II)

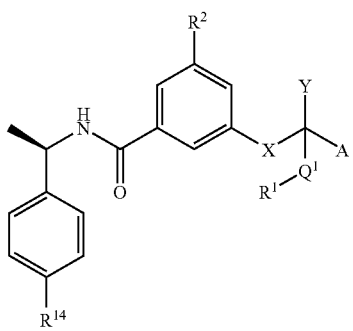
(II)

and pharmaceutically acceptable salts thereof, and individual enantiomers and diastereomers thereof, wherein A, $Q^1$, X, Y, $R^1$ and $R^2$ are as described above, and $R^{14}$ is selected from the group consisting of:
(a) hydrogen,
(b) halogen (preferably fluoro); and
(c) $C_{1-10}$ alkyl.

In one embodiment of the compounds of formula (II), $R^1$ is phenyl and $Q^1$ is $CH_2$.

In another embodiment of the compounds of formula (II) wherein Y is $NH_2$.

In another embodiment of compounds of formula (II), Y is OH.

In another embodiment of the compounds of formula (II), A is $C_{1-10}$ alkyl, preferably $C_{1-6}$ alkyl, more preferably methyl.

In another embodiment of the compounds of formula (II), $R^2$ is —$(R^4)NSO_2R^7$, and $R^4$ and $R^7$ are $C_{1-10}$ alkyl, preferably $C_{1-6}$ alkyl. More preferably, $R^4$ is methyl or isopropyl and $R^7$ is methyl or propyl.

In another embodiment of the compounds of formula (II), X is an oxadiazole selected from the group consisting of

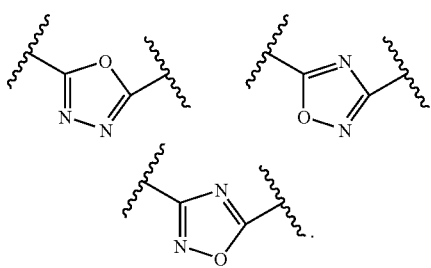

In another embodiment of the compounds of formula (II), X is an oxazole selected from

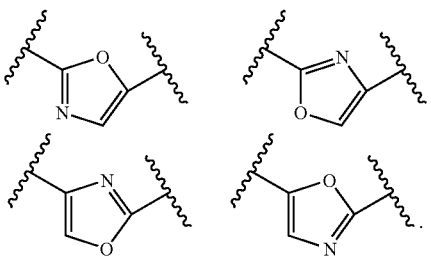

In another embodiment of the compounds of formula (II), X is a furan, as shown below

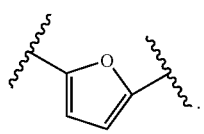

In another embodiment, the invention is directed to compounds of formula (III)

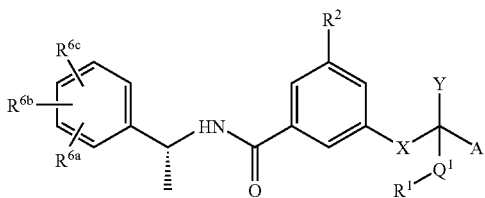
(III)

and pharmaceutically acceptable salts thereof, and individual enantiomers and diastereomers thereof, wherein A, $Q^1$, X, Y, $R^1$, $R^2$, $R^{6a}$, $R^{6b}$ and $R^{6c}$ are as described above.

In one embodiment of the compounds of formula (III), $R^1$ is phenyl and $Q^1$ is $CH_2$.

In another embodiment of the compounds of formula (III), Y is $NH_2$.

In another embodiment of compounds of formula (III), Y is OH.

In another embodiment of the compounds of formula (III), A is $C_{1-10}$ alkyl, preferably $C_{1-6}$ alkyl, more preferably methyl.

In another embodiment of the compounds of formula (III), $R^2$ is selected from the group consisting of
(a) —$(R^4)NSO_2R^7$, and $R^4$ and $R^7$ are $C_{1-10}$ alkyl, preferably $C_{1-6}$ alkyl. More preferably, $R^4$ is methyl or isopropyl and $R^7$ is methyl or propyl;

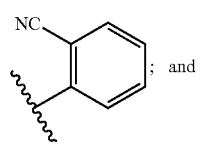
(b)
; and

-continued (c)

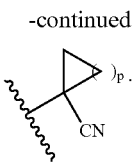

In another embodiment of the compounds of formula (III), X is an oxadiazole selected from the group consisting of

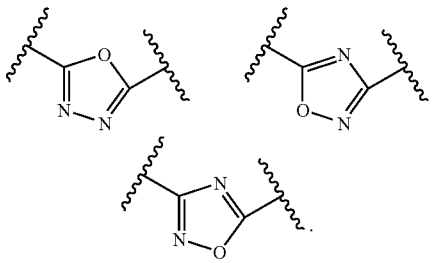

In another embodiment of the compounds of formula (III), X is an oxazole selected from

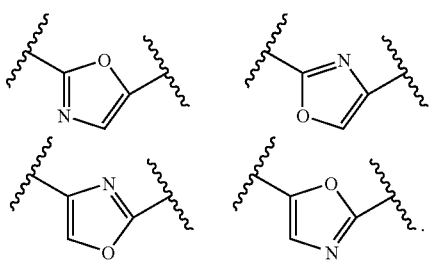

In another embodiment of the compounds of formula (III), X is a furan, as shown below

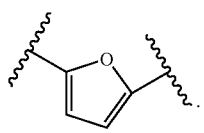

In another embodiment, the invention is directed to compounds of formula (IV)

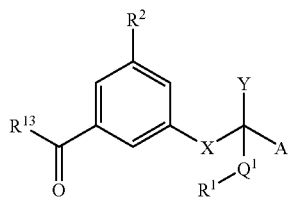

(IV)

and pharmaceutically acceptable salts thereof, and individual enantiomers and diastereomers thereof, wherein A, $Q^1$, X, Y, $R^1$, $R^2$ and $R^{13}$ are as described above.

In one embodiment of the compounds of formula (IV), $R^1$ is phenyl and $Q^1$ is $CH_2$.

In another embodiment of the compounds of formula (IV), Y is $NH_2$.

In another embodiment of compounds of formula (IV), Y is OH.

In another embodiment of the compounds of formula (IV), A is $C_{1-10}$ alkyl, preferably $C_{1-6}$ alkyl, more preferably methyl.

In another embodiment of the compounds of formula (IV), $R^2$ is selected from the group consisting of —$(R^4)NSO_2R^7$, and $R^4$ and $R^7$ are $C_{1-10}$ alkyl, preferably $C_{1-6}$ alkyl. More preferably, $R^4$ is methyl or isopropyl and $R^7$ is methyl or propyl.

In another embodiment of the compounds of formula (IV), $R^{13}$ is selected from the group consisting of
(a) phenyl,
(b) $C_{1-10}$ alkyl, and
(b) $C_{3-10}$ cycloalkyl (preferably $C_{3-6}$ cycloalkyl).

In another embodiment of the compounds of formula (IV), X is an oxadiazole selected from the group consisting of

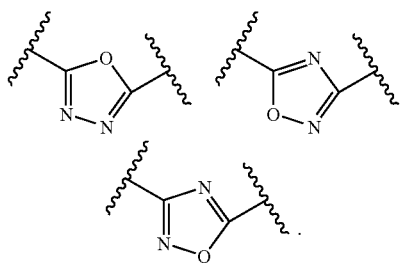

In another embodiment of the compounds of formula (IV), X is an oxazole selected from

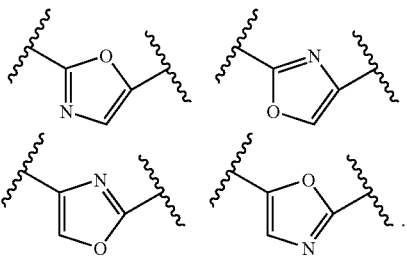

In another embodiment of the compounds of formula (IV), X is a furan, as shown below

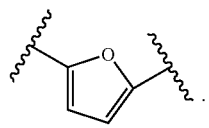

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkenyl groups include ethynyl and propynyl.

As used herein, the term "cycloalkyl," by itself or as part of another substituent, means a saturated cyclic hydrocarbon radical having the number of carbon atoms designated (e.g., $C_{3-8}$ cycloalkyl means a cycloalkyl group having from three to eight carbon atoms). Exemplary cycloalkyl groups include cyclopropyl, cyclobutyl, cyclopentyl, cyclohexyl and the like.

As used herein, the term "aryl," by itself or as part of another substituent, means an aromatic or cyclic radical having the number of carbon atoms designated (e.g., $C_{6-10}$ aryl means an aryl group having from six to ten carbons atoms). Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

In the compounds of formulas (I) to (IV), the carbon atom to which Y, A and $Q^1$ are bonded is typically a chiral carbon. As a result, the compounds of formulas (I)-(IV) may be present as racemates, or in stereochemically pure forms. The isomeric forms for compounds of formula (I) are depicted as (IA) and (IB) below:

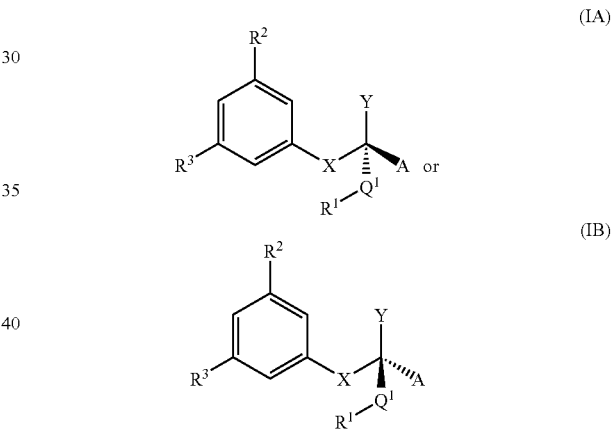

The first configuration depicted above (which is the R configuration when A is methyl, $Q^1$ is $CH_2$ and Y is $NH_2$) is preferred.

Preferred configurations of compounds of formula (II), (III) and (IV) are shown below, as (IIA), (IIIA) and (IVA), respectively:

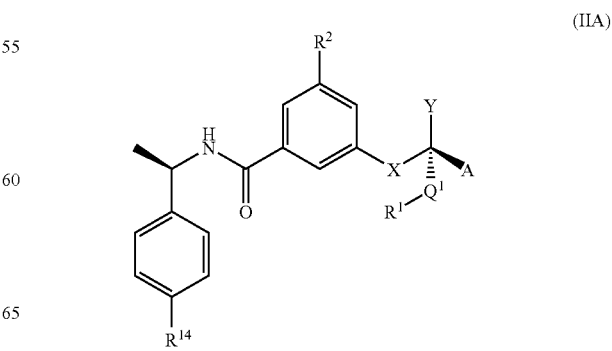

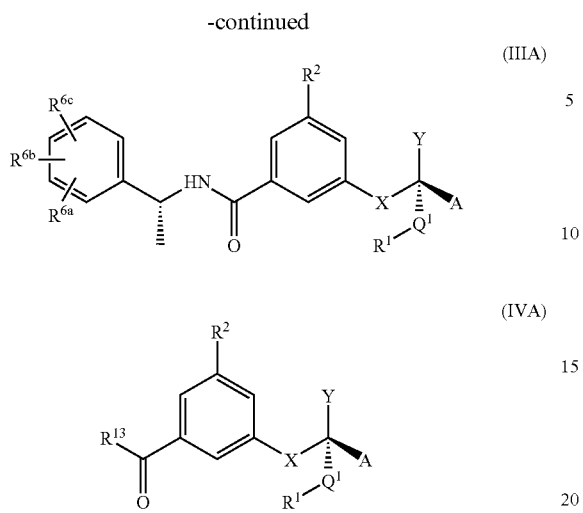

The compounds claimed in this invention can be prepared according to the following general procedure methods, and the specific examples.

In Scheme 1, an amino acid derivative of type 1 is converted to the corresponding hydrazinyl amide 3 via a two step sequence. To access commercially unavailable amino acid derivatives, a two step alkylation of glycine Schiff base 4 can be utilized. Schiff base deprotection, Boc protection and ester hydrolysis provides an alternate route to compound 2. The alkylation of 4 for the synthesis of 5 may be performed in enantioselective manner as described in the literature (see: K. Maruoka et al, *J. Am. Chem. Soc.* 2000, 122, 5228-5229 and M. North et al, *Tetrahedron Lett.* 2003, 44, 2045-2048).

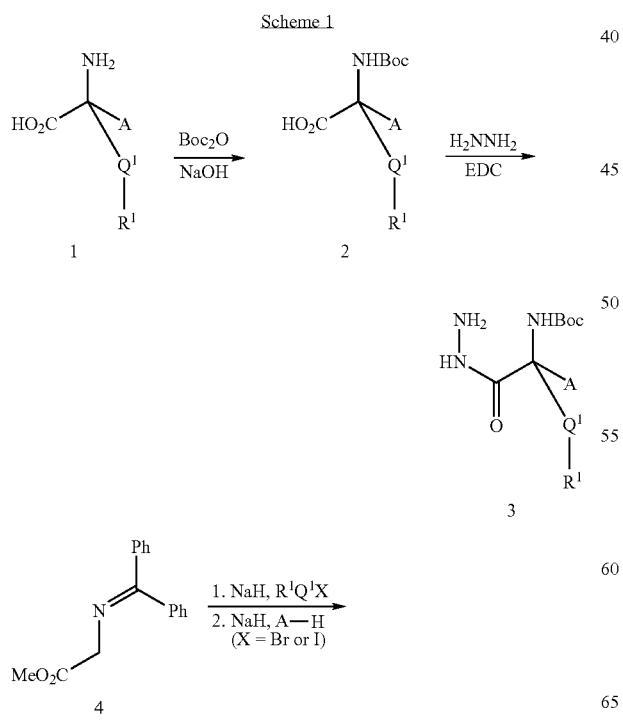

In Scheme 2, N-protected amino acid 2 is converted to carboxamide 6, which can be transformed to thioamide 7 or dehydrated to give nitrile 8. Treatment of 8 with $NH_2OH$—HCl under mildly basic conditions affords hydroxyamidate 9.

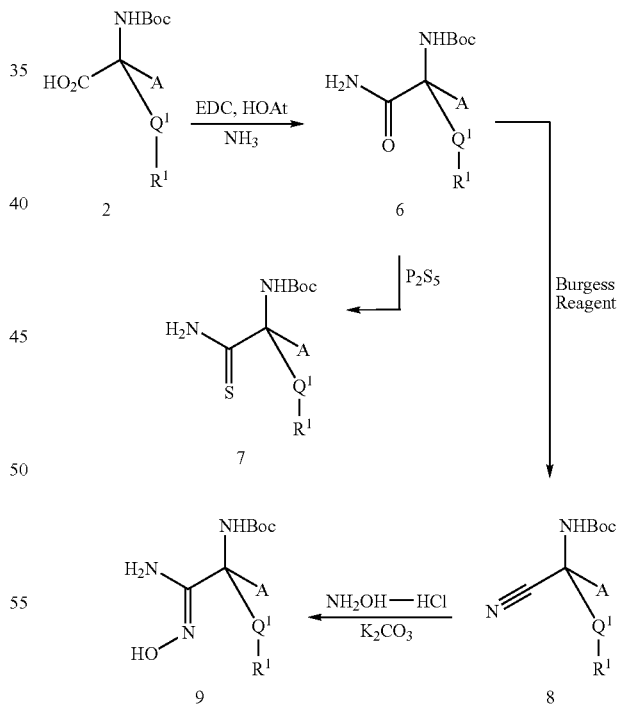

In Scheme 3, reduction of amino acid 1 with in-situ generated $BH_3$ affords the corresponding amino alcohol, which can then be N-protected to afford compound 10. Oxidation of 10 affords aldehyde 11, which can then be transformed to imine 12 under mild conditions.

Scheme 3

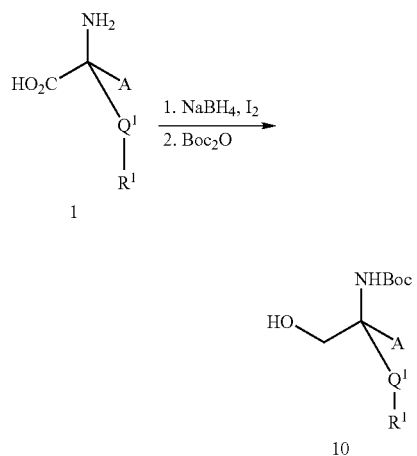

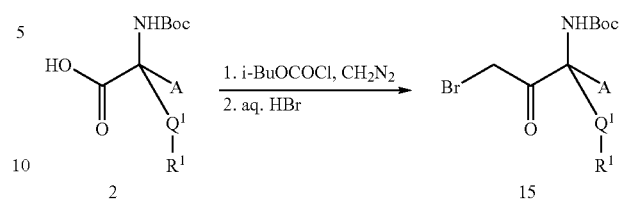

In Scheme 7, below, dimethyl 5-aminoisophthalate 16 is converted to acid 17 via a 3-step sequence involving sulfonylation, alkylation and ester hydrolysis. Further elaboration of 17 via amide bond formation and methyl ester hydrolysis gives access to derivative 18.

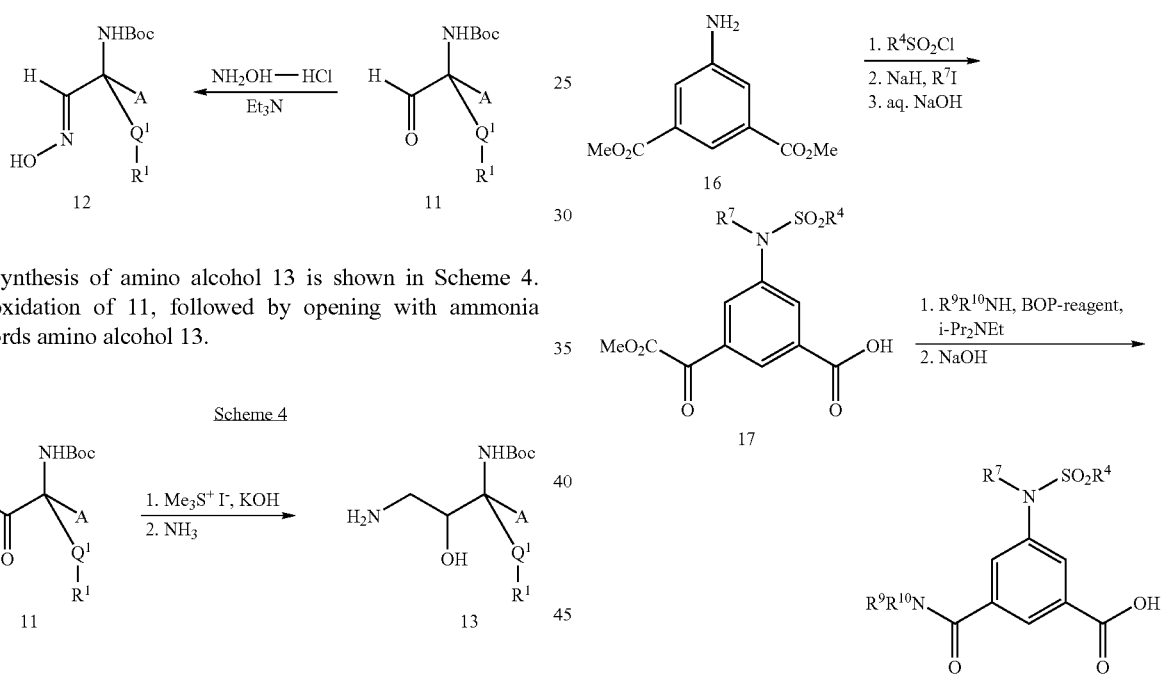

Synthesis of amino alcohol 13 is shown in Scheme 4. Epoxidation of 11, followed by opening with ammonia affords amino alcohol 13.

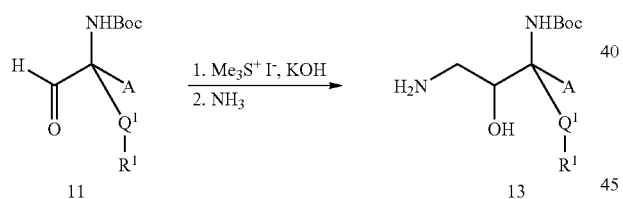

Scheme 5 illustrates the preparation of the regioisomeric amino alcohol 14. Synthesis of the Ellman sulfinyl imine of aldehyde 11, vinyl Grignard addition, olefin ozonolysis under reductive conditions and selective removal of the Ellman chiral auxiliary affords 14.

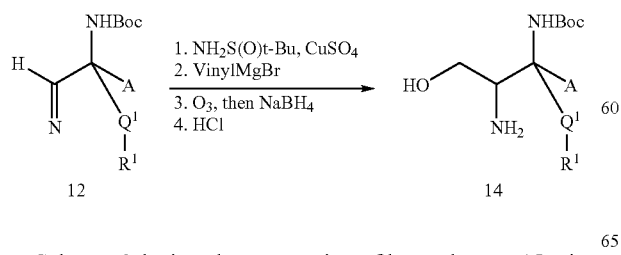

Scheme 6 depicts the preparation of bromoketone 15, via the diazoketone intermediate derived from acid 2.

The synthesis of bromide 20b is shown in Scheme 8. Beginning with acid 19, a 7 step sequence involving esterification, sulfonylation, alkylation, ester hydrolysis, amine coupling, nitro reduction gives aniline 20a. Sandmeyer reaction of 20a affords aryl bromide 20b.

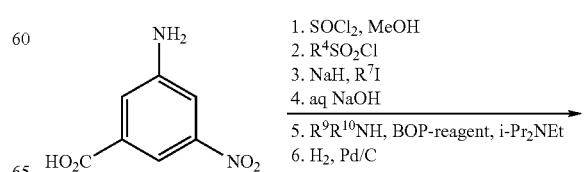

-continued

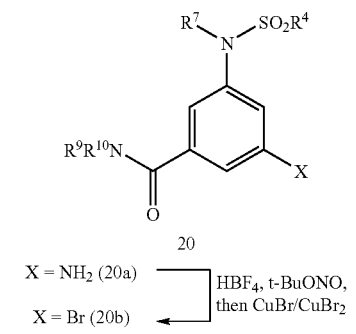
20

X = NH$_2$ (20a)
X = Br (20b)
HBF$_4$, t-BuONO, then CuBr/CuBr$_2$

Scheme 9 illustrates the preparation of acids of type 23 from dimethyl 5-iodoisophthalate 21. Cross coupling and hydrolysis affords acid 22, which can be further elaborated to 23 via amine coupling and ester hydrolysis.

Scheme 9

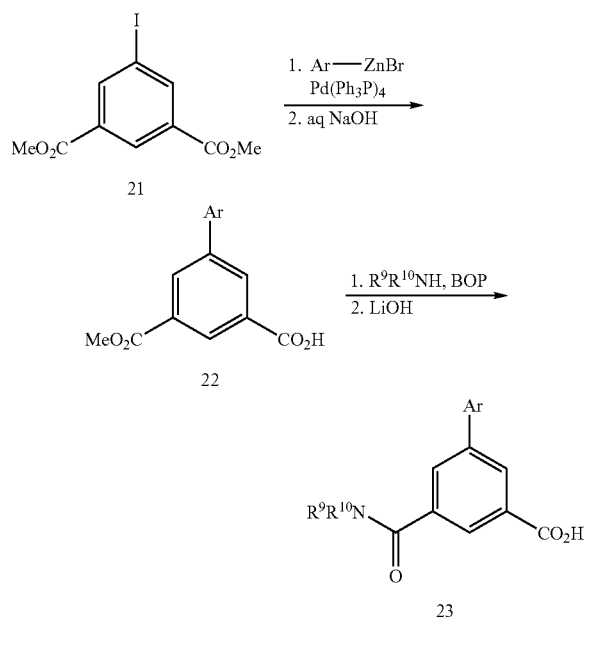

Scheme 10 illustrates the preparation of acids of type 26. Phenol 24 is alkylated and the methyl ester is converted to a bromomethyl functionality giving access to intermediate 25. The cyano-cycloalkyl group is introduced via TMS-CN and the necessary dibromoalkane. Subsequent cyclopropanation and ester hydrolysis provides acid 26.

Scheme 10

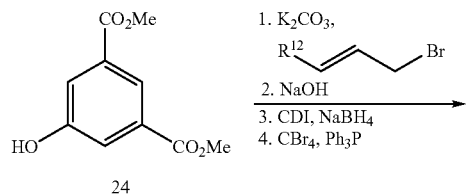

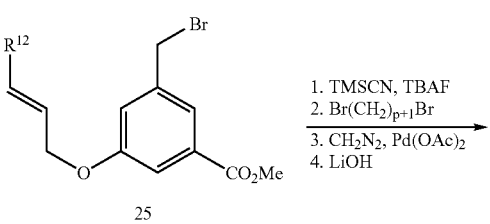

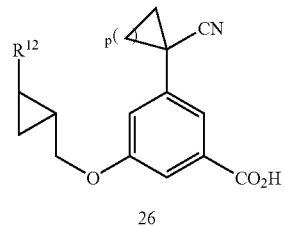

The preparation of acid 29 relies on a reaction sequence similar to that described above for the installation of the R$^{12}$-bearing side chain, and is described in Scheme 11. The R$^2$ sulfonamide is introduced via a Curtius rearrangement, followed by sulfonylation and alkylation.

Scheme 11

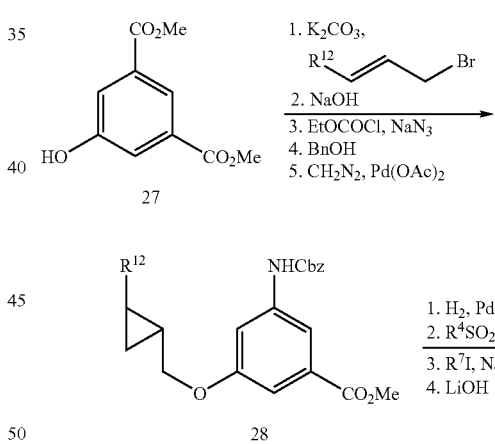

Scheme 12 illustrates two alternative preparations of acids of type 30. The first preparation relies on conversion of the methyl ester to an aldehyde followed by a Wittig coupling to install the R$^{12}$-bearing alkene. The second preparation is based on an indenium/palladium coupling strategy.

Scheme 12

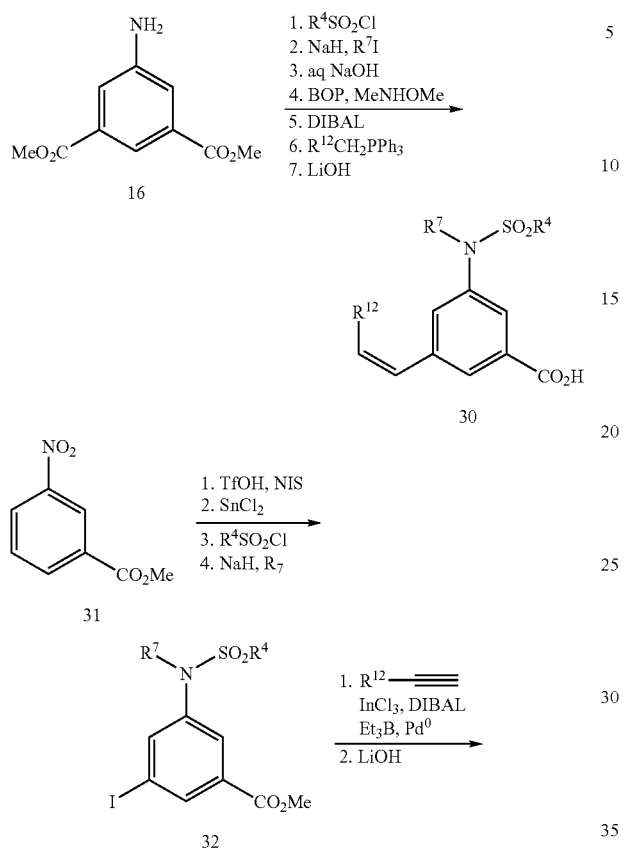

The general preparation of benzoic acids of type 34 and 35 are shown as Scheme 13. Starting with 33, bromination of the benzyl alcohol, cyamide displacement of the resulting benzyl bromide and alkylation with the appropriate dibromoalkane provides the corresponding cyanocarbocycle. Ester monohydrolysis completes the synthesis of acid 34. Amine coupling and hydrolysis of the second ester completes the elaboration of 34 to 35.

Scheme 13

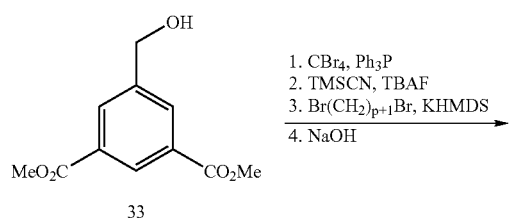

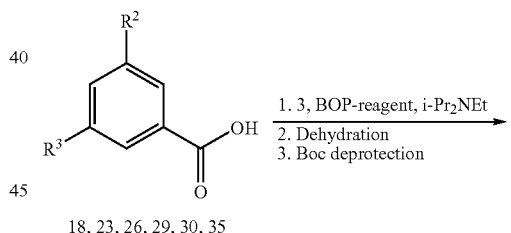

Synthesis of the 1,3,4 oxadiazoles of type 36 could be accomplished by coupling acids 18, 23, 26, 29, 30, or 35 with hydrazinyl amide 3, dehydration with Burgess reagent or Ph$_3$P/CBr$_4$/Im, and Boc deprotection, as shown in Scheme 14. Alternatively, the oxadiazole could be synthesized prior to the formation of the abovementioned amide bond. Coupling acids 17, 22, or 34 with 2, oxadiazole formation and ester hydrolysis affords acid 37. Installation of the amide and Boc deprotection provides an alternate route to compounds of type 36.

Scheme 14

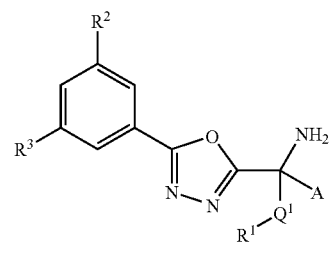

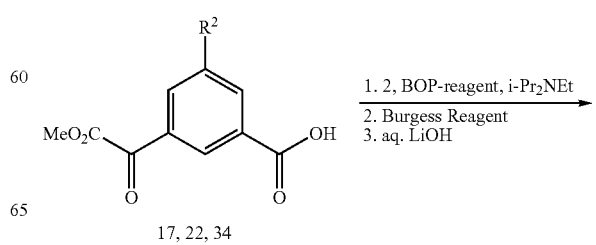

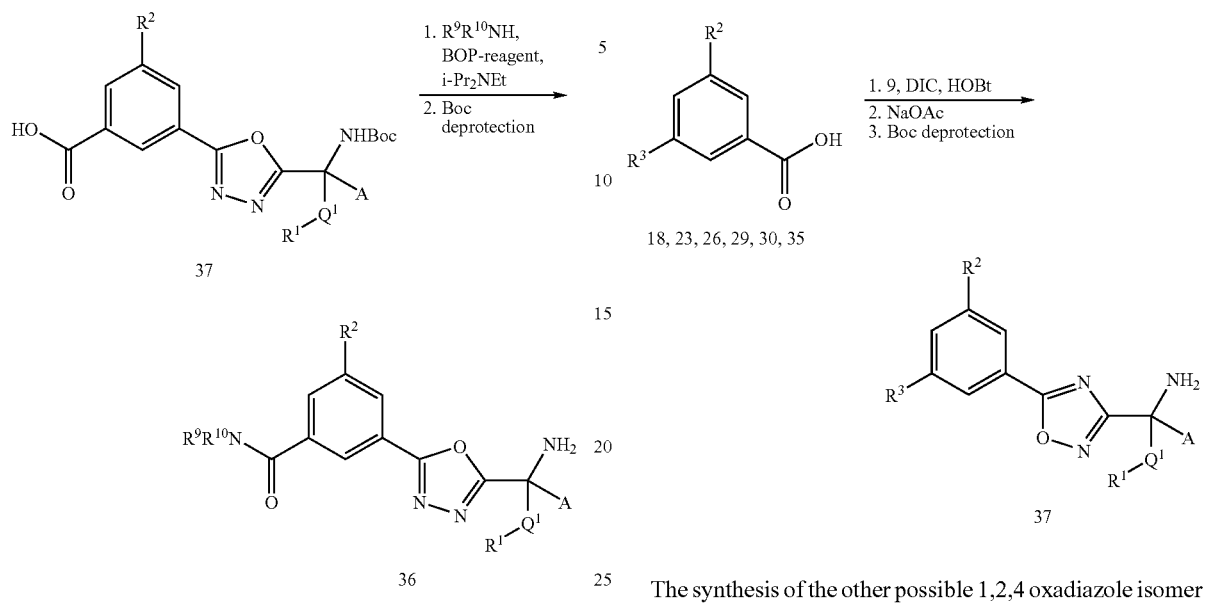

The synthesis of one of the two possible 1,2,4 oxadiazole isomers is shown as Scheme 15. Coupling acids 18, 23, 26, 29, 30, or 35 with hydroxyamidate 9, dehydration under basic conditions, and Boc deprotection affords oxadiazoles of type 37.

The synthesis of the other possible 1,2,4 oxadiazole isomer can be achieved from acids 18, 23, 26, 29, 30, or 35 as shown in Scheme 16. Carboxamide formation and dehydration affords nitriles of type 38a. A sequence similar to that described above for Scheme 15 affords oxadiazole 40. Nitriles of type 38b can also be accessed from the cross coupling reaction of aryl bromide 20b.

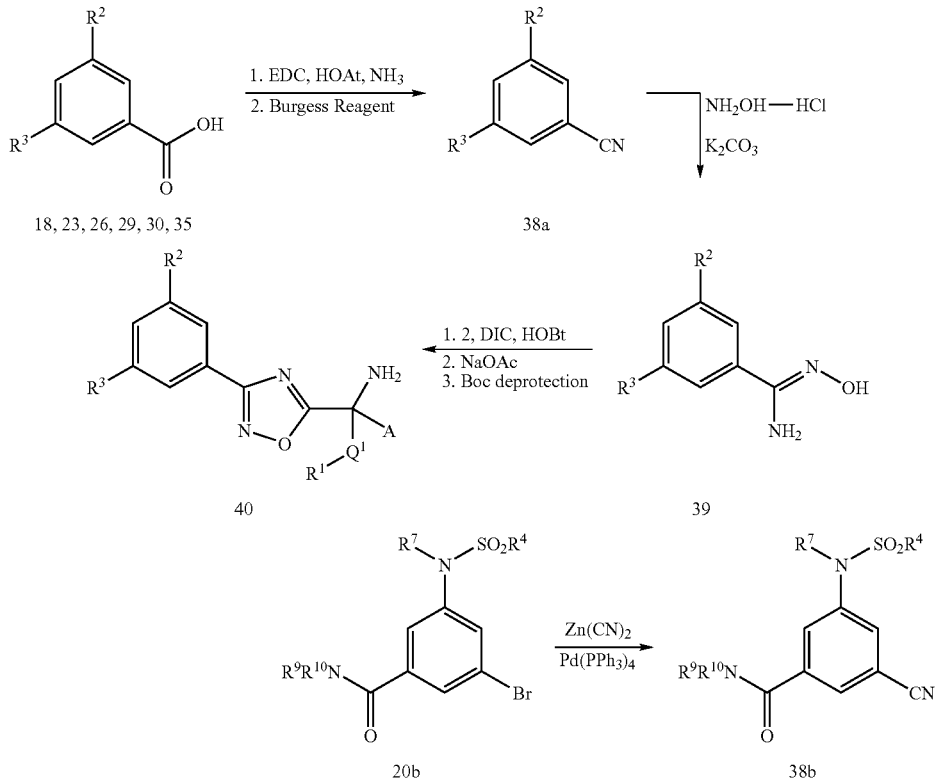

The synthesis of 1,2,4 triazole 42 is described in Scheme 17. Transformation of nitrile 38a or 38b to imidate 41 under basic conditions, followed by refluxing with hydrazinyl amide 3 and Boc deprotection affords the requisite heterocycle.

Scheme 17

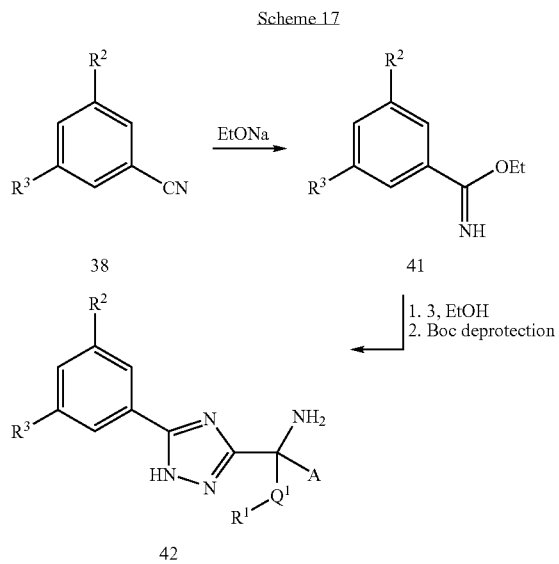

N-aryl imidazole 45 is prepared as described in Scheme 18. Coupling of 13 with formic and, oxidation, followed by ring closure affords imidazole 43. The Hunsdieker reaction with acids 18, 23, 26, 29, 30, or 35 gives access to aryl bromides of type 44. Transformation of 44 to the corresponding boronic acid via lithium halogen exchange, coupling with imidazole 39, and Boc deprotection completes the reaction sequence to compound 45. If an acidic NH (i.e. a secondary amide as in the case of 20b) is present on aryl bromide 44, the corresponding metalloimidate may be formed by adding a Grignard reagent prior to the lithium halogen exchange event to facilitate the success of the latter reaction. This practice has been commonly used in the literature.

Scheme 18

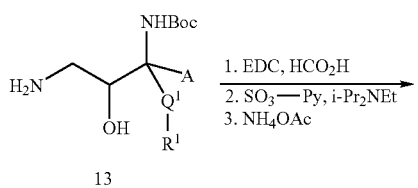

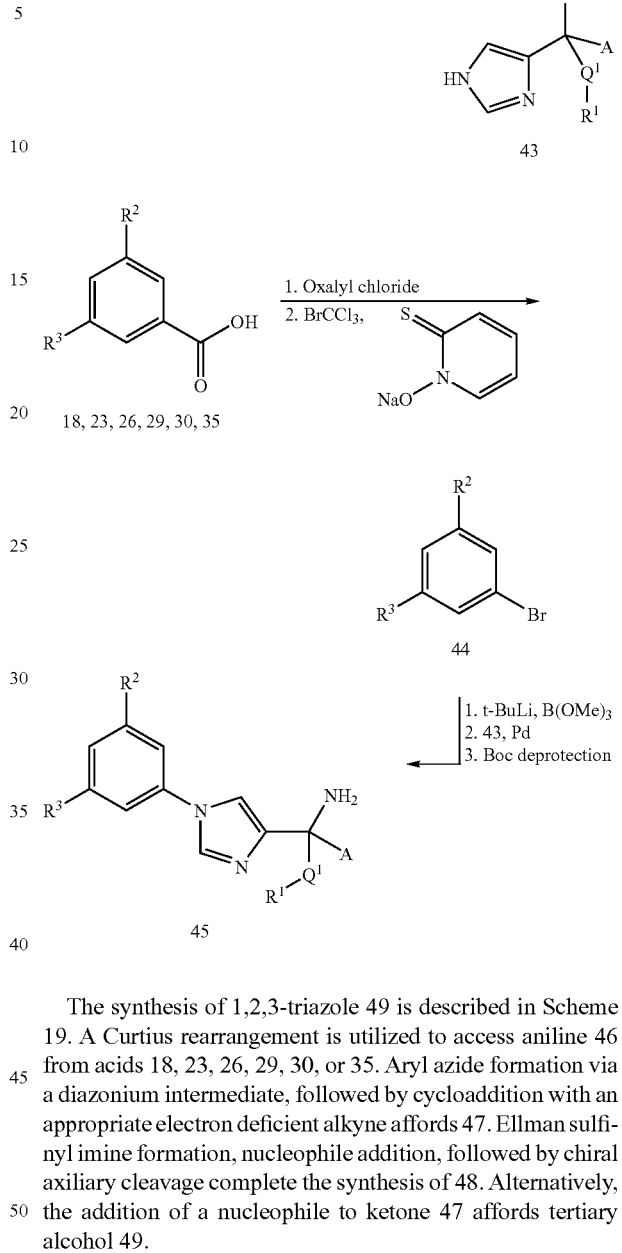

The synthesis of 1,2,3-triazole 49 is described in Scheme 19. A Curtius rearrangement is utilized to access aniline 46 from acids 18, 23, 26, 29, 30, or 35. Aryl azide formation via a diazonium intermediate, followed by cycloaddition with an appropriate electron deficient alkyne affords 47. Ellman sulfinyl imine formation, nucleophile addition, followed by chiral axiliary cleavage complete the synthesis of 48. Alternatively, the addition of a nucleophile to ketone 47 affords tertiary alcohol 49.

Scheme 19

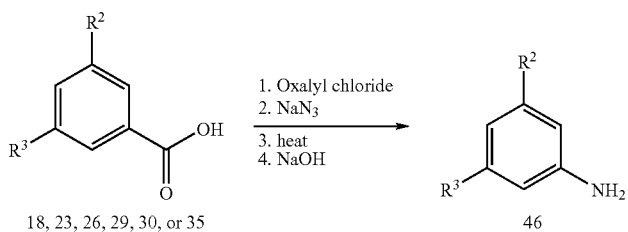

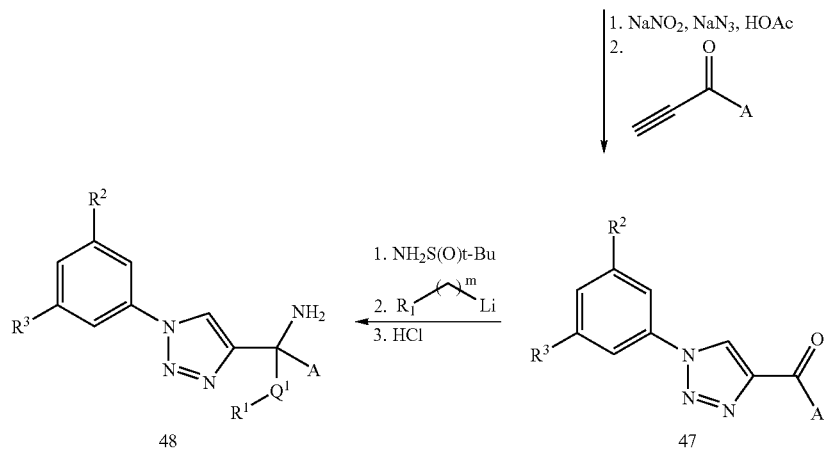

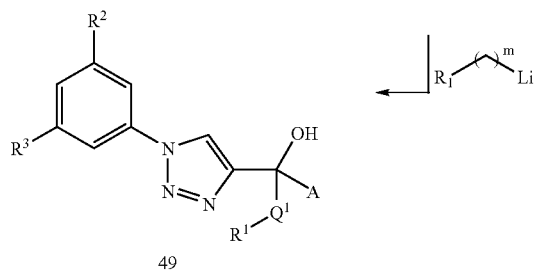

The synthesis of oxazoles 51, thiazoles 52, and imidazoles 53 is shown in Scheme 20. Reduction of acids 18, 23, 26, 29, 30, or 35, oxidation to the aldehyde, epoxidation, expoxide opening with ammonia, followed by coupling the resulting amino alcohol with acid 2 affords the common intermediate 50. Oxidation, dehydrative cyclization under the described conditions and Boc deprotection gives access to 51, 52 or 53.

Scheme 20

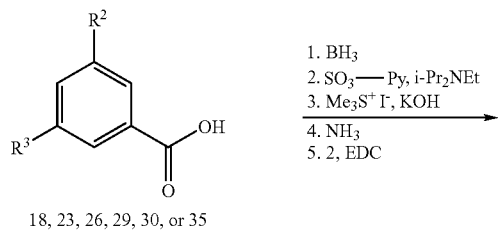

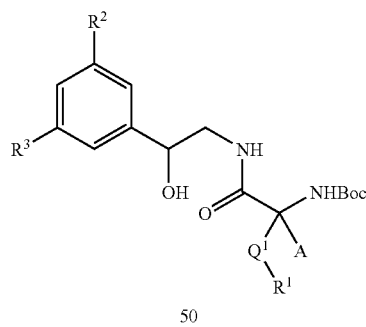

-continued

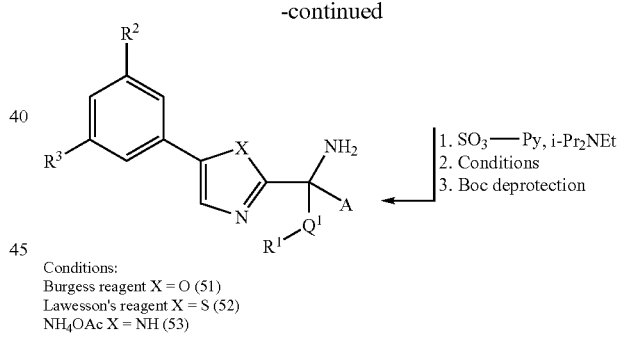

Conditions:
Burgess reagent X = O (51)
Lawesson's reagent X = S (52)
NH₄OAc X = NH (53)

A second series of regioisomeric oxazoles and thiazoles can be synthesized from aryl bromide 44, as described in Scheme 21. Cross coupling, Sharpless asymmetric amination and coupling with acid 2 gives common intermediate 54. Application of conditions described above provides oxazole 55, thiazole 56, as well as an alternate route to imidazole 53.

Scheme 21

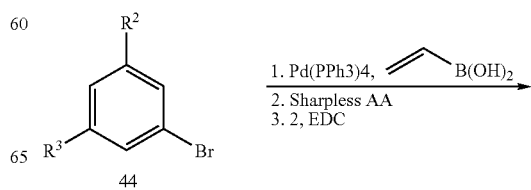

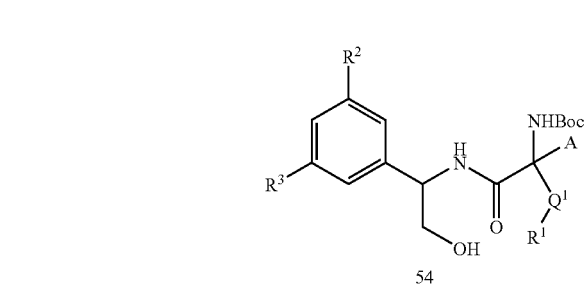

54

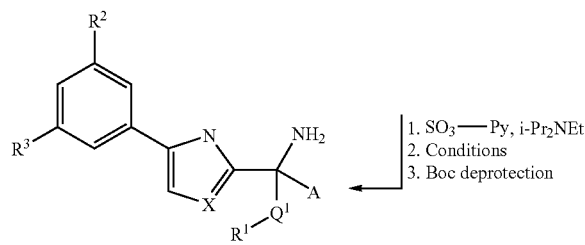

Conditions:
Burgess reagent X = O (55)
Lawesson's reagent X = S (56)
NH₄OAc X = NH (57)

Shown below in Scheme 22 is the synthesis of a third series of regioisomeric oxazoles 58, thiazoles 59 and imidazoles 60. Coupling acids 18, 23, 26, 29, 30, or 35 with amino alcohol 12, oxidation, cyclodehydration under the appropriate conditions followed by Boc deprotection provides the desired compounds.

Scheme 22

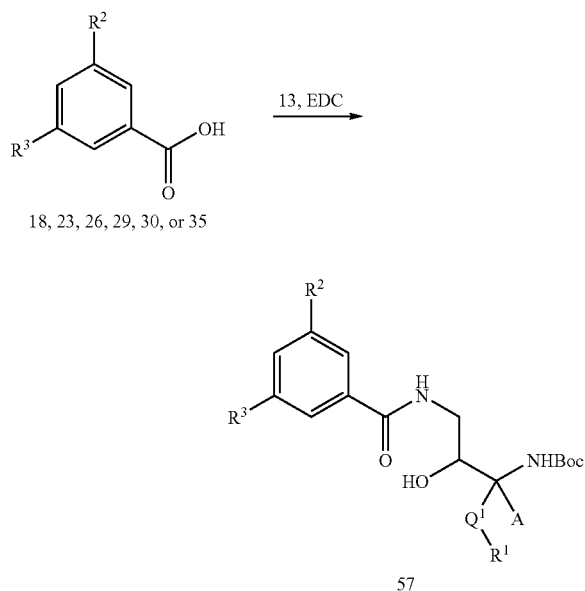

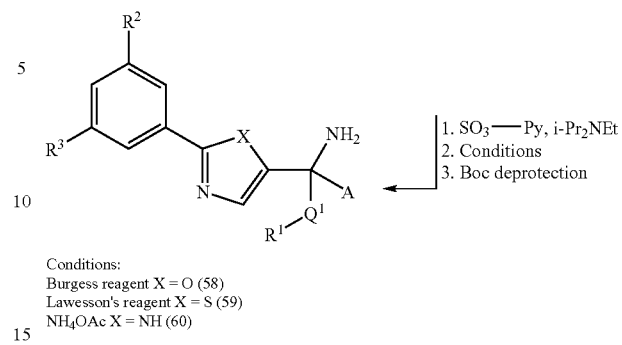

Conditions:
Burgess reagent X = O (58)
Lawesson's reagent X = S (59)
NH₄OAc X = NH (60)

The synthesis of a fourth possible permutation of oxazoles 62, thiazoles 62, and an alternate route to imidazole 63 is shown in Scheme 23. EDC coupling of 14 with acids 18, 23, 26, 29, 30, or 35 provides intermediate 61. Oxidation and cyclodehydration under the appropriate conditions gives the desired five membered heterocycle.

Scheme 23

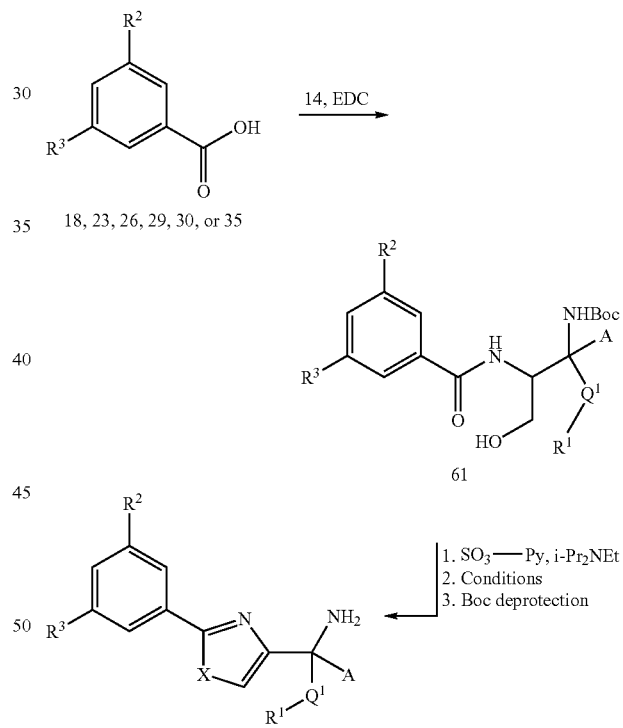

Conditions:
Burgess reagent X = O (62)
Lawesson's reagent X = S (63)
NH₄OAc X = NH (60)

Scheme 24 shows an alternative mode of preparation for heterocycles 60, 62, and 63. Displacement of bromoketone 15 with acids 18, 23, 26, 29, 30, or 35, cyclization in the presence of an amonia source, followed by Boc removal affords imidazole 60. Displacement with carboxamide 64, cyclization, and Boc removal affords oxazole 62. Displacement with thiocarboxamide 65, cyclization, followed by Boc removal affords thiazole 63.

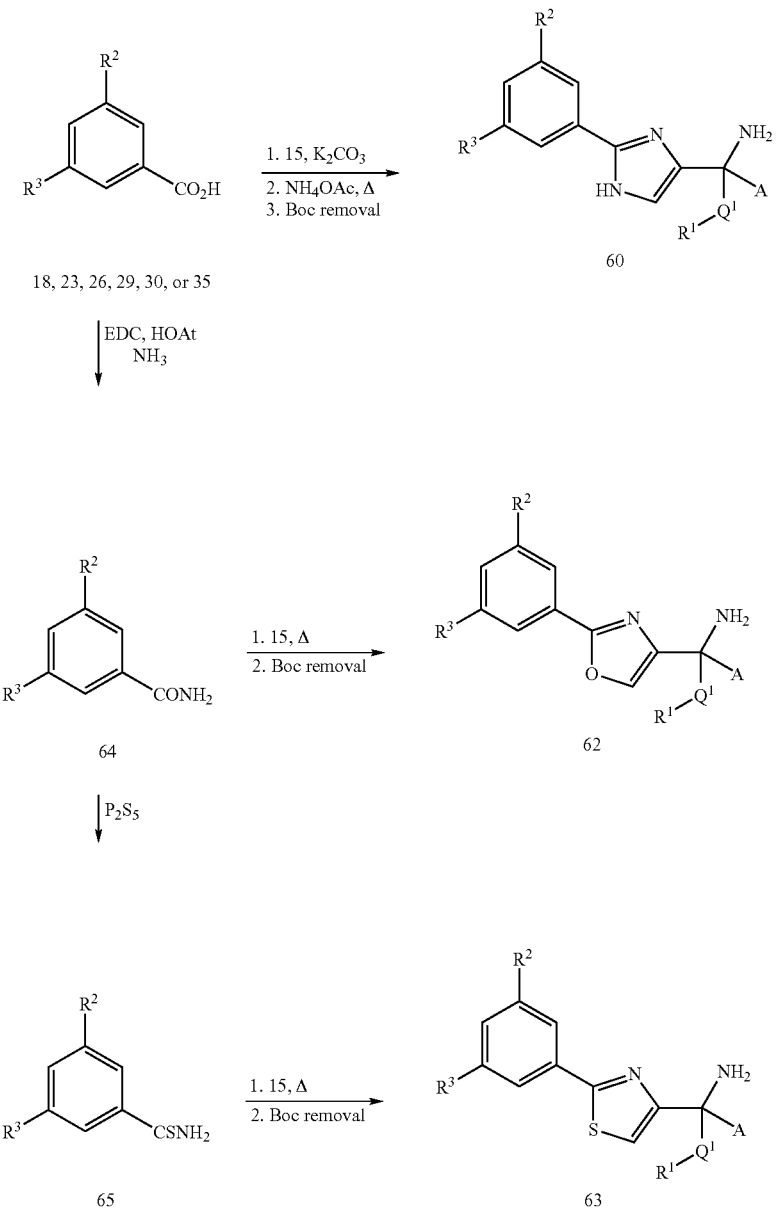
Isoxazoles of type 67 can be prepared as described in Scheme 25. Cross coupling of aryl bromide 44 with TMS acetylene and deprotection gives 66. Cycloaddition with the nitrile oxide derivative prepared from the in-situ oxidation of 12, followed by Boc deprotection provides isoxazole 67.
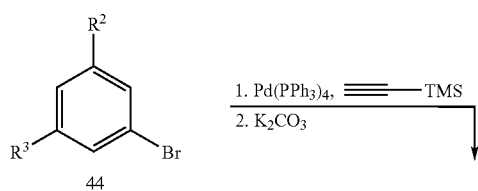

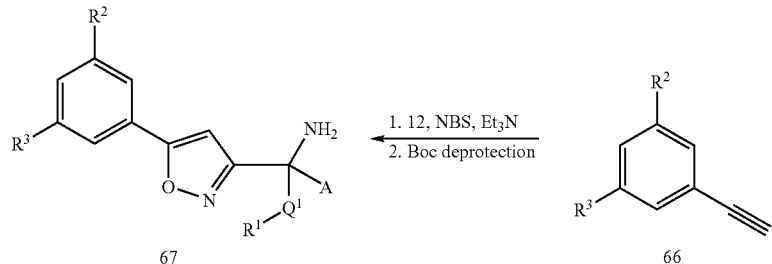

The synthesis of the second isoxazole regioisomer can be accomplished utilizing a sequence as described previously, and this is given as Scheme 26. Aldehyde 11 can be elaborated to alkyne 68 utilizing Corey-Fuchs methodology. Acid reduction, oxidation and hydroxy imidate formation gives 69. In situ nitrile oxide generation and cycloaddition, followed by Boc group removal affords isoxazoles of type 70.

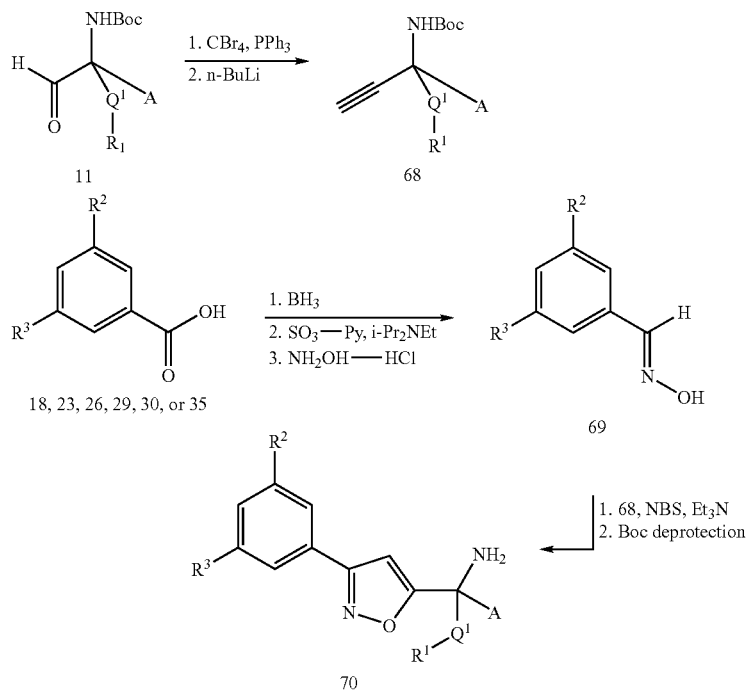

Ketones of type 71 can be accessed from acid 37, as shown in Scheme 27. Weinreb amide formation, Grignard addition and Boc deprotection completes the synthetic sequence.

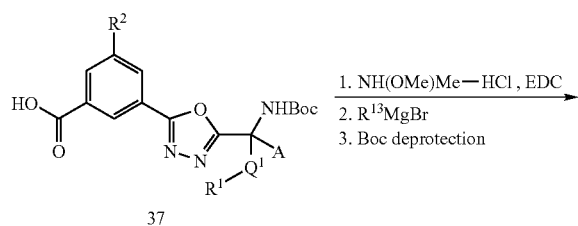

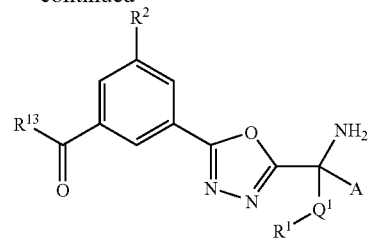

Benzylamines of type 73 and benzyl ethers such as 74 can be accessed from the alkylation of benzyl bromide 72, as described in Scheme 28. Preparation of 72 involves reduction of acid 37, followed by bromination of the corresponding benzyl alcohol.

Scheme 28

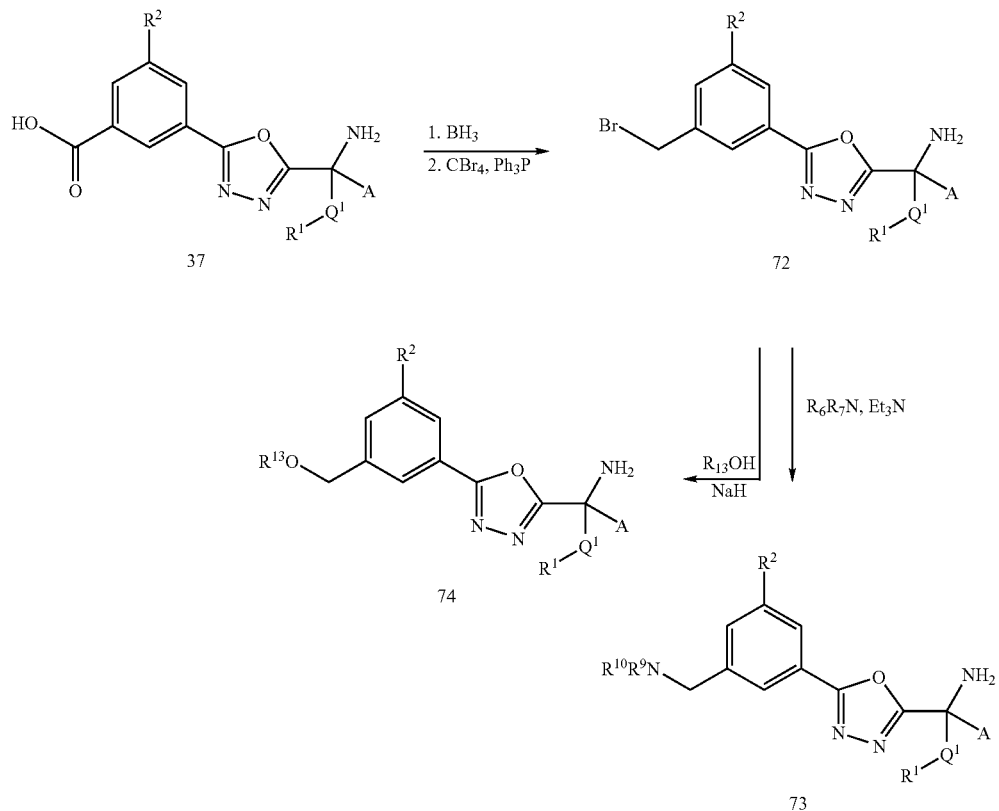

Scheme 29

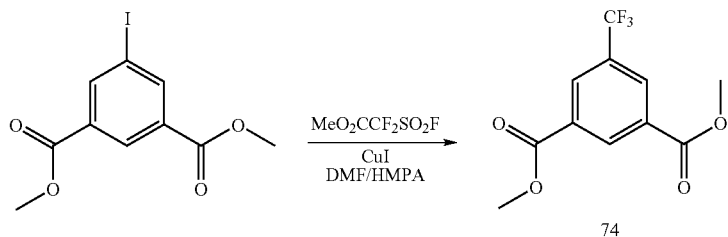

Scheme 29 shows the general preparation of 5-trifluoromethyl substituted isophthalates of type 74. Compound 74 can be elaborated to the desired target compounds as described in Schemes 7 and 14.

Scheme 30

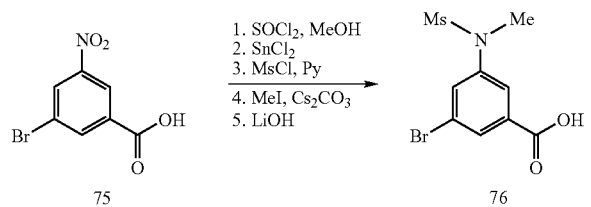

-continued

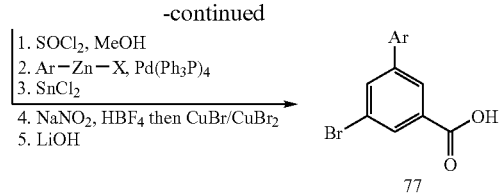

Scheme 30 shows the synthesis of acids of type 76 and 77. Beginning with commercially available 75, esterification, nitro reduction, mesylation, N-methylation and ester hydrolysis provides acid 76. Starting acid 75 is similarly elaborated to 77 through an esterification, cross coupling, nitro reduction, Sandmeyer and saponification sequence.

Scheme 31

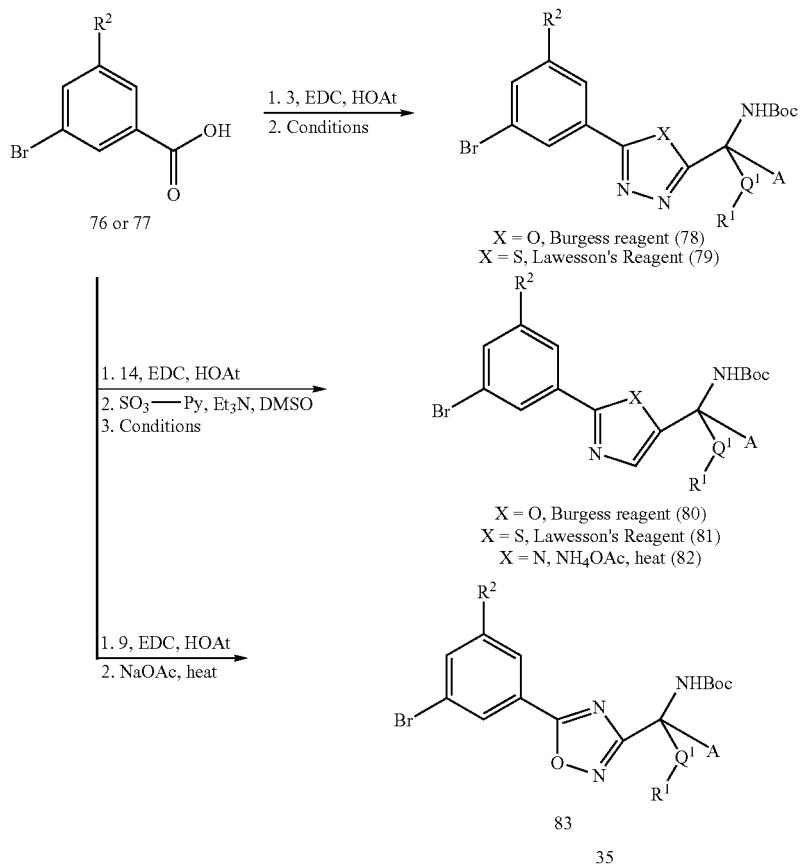

Functionalized aryl bromides 78-83 were synthesized following the sequence described in Scheme 31. Coupling of acids 76 or 77 with acylhydrazide 3, followed by dehydration with Burgess reagent or Lawesson's reagent affords oxadiazole 78 and thaidiazole 79. Similarly, coupling acids 76 or 77 with 14, oxidation and dehydration under various conditions gives oxazole 80, thiazole 81 and imidazole 82. Coupling of 76 or 77 with 9 and dehydration under mildly basic conditions gives the regioisomeric oxadiazole 83.

Scheme 32

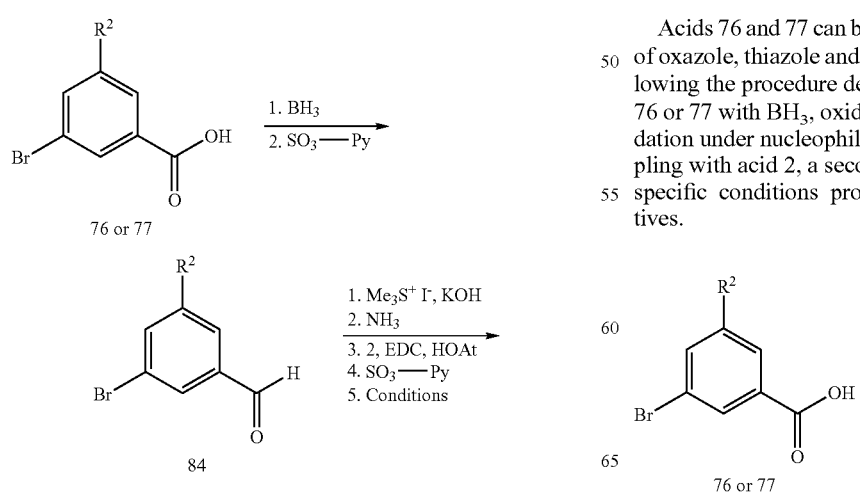

-continued

X = O, Burgess reagent (85)
X = S, Lawesson's Reagent (86)
X = N, NH$_4$OAc, heat (87)

Acids 76 and 77 can be elaborated to a regioisomeric series of oxazole, thiazole and imidazole bearing intermediates following the procedure described in Scheme 32. Reduction of 76 or 77 with BH$_3$, oxidation of the resulting alcohol, epoxidation under nucleophilic conditions, epoxide opening, coupling with acid 2, a second oxidation and dehydration under specific conditions provides the above-referenced derivatives.

Scheme 33

1. EDC, NH$_3$
2. Burgess Reagent
3. NH$_2$OH
4. 2, EDC
5. NaOAc

-continued

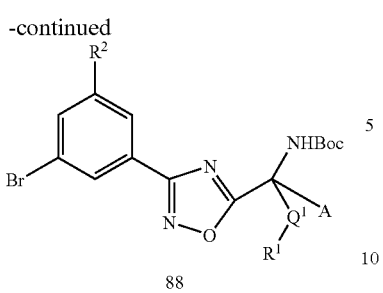
88

Another regioisomeric oxadiazole series can be synthesized from acids 76 or 77 as described in Scheme 33. Carboxamide formation, dehydration to the corresponding nitrile, hydroxyamidine formation, coupling with amino acid 2 and dehydration under mildly basic conditions completes the synthesis of aryl bromides of type 88.

Scheme 34. Negishi type couplings, followed by Boc deprotection affords compounds of type 89. Judicious choice of protecting groups for heteroatoms present in the organometallic reagent allows introduction of polar functionality, and these groups often require separate deprotection steps. The starting aryl bromide may undergo an amination reaction to provide anilines of type 90.

Scheme 34

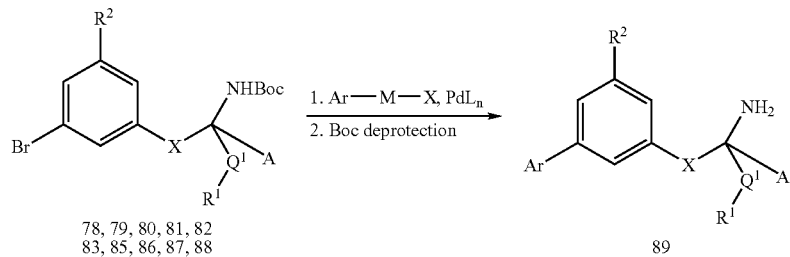

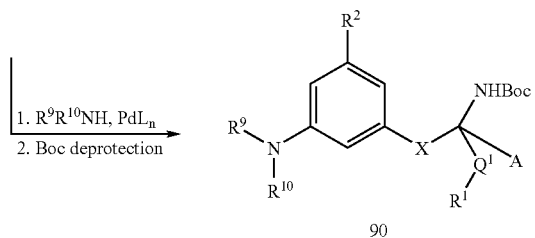
90

Acids 78, 79, 80, 81, 82, 83, 85, 86, 87 and 88 are further elaborated to structures of type 89 and 90 as described in Scheme 35

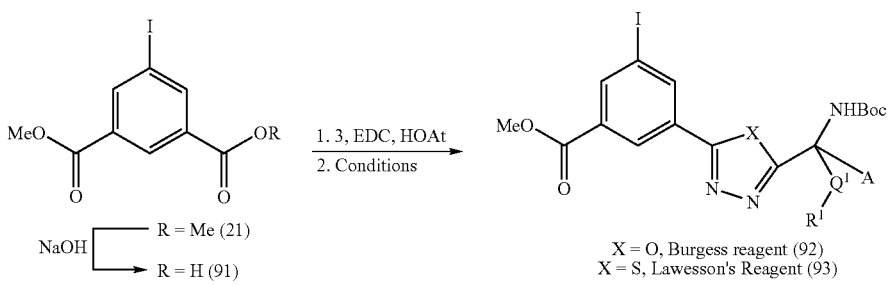

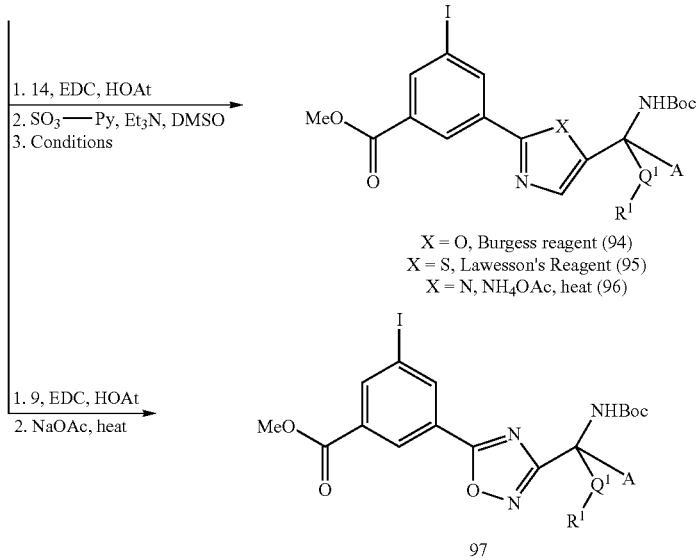

Functionalized aryl bromides 92-97 were synthesized following the sequence described in Scheme 31. Monohydrolysis of 21 and coupling of acid resulting acid 91 with acylhydrazide 3, followed by dehydration with Burgess reagent or Lawesson's reagent affords oxadiazole 92 and thaidiazole 93. Similarly, coupling acid 91 with 14, oxidation and dehydration under various conditions gives oxazole 94, thiazole 95 and imidazole 96. Coupling of 76 or 77 with 9 and dehydration under mildly basic conditions gives the regioisomeric oxadiazole 97.

Acid 91 was elaborated to a regioisomeric series of oxazole, thiazole and imidazole bearing intermediates following the procedure described in Scheme 36. Reduction of 91 with $BH_3$, oxidation of the resulting alcohol, epoxidation under nucleophilic conditions, epoxide opening, coupling with acid 2, a second oxidation and dehydration under specific conditions provides the above-referenced derivatives.

Scheme 36

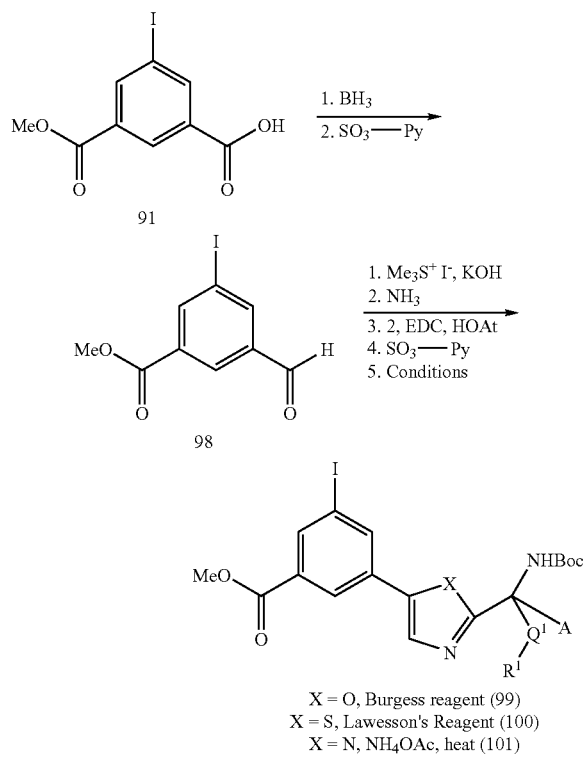

Scheme 37

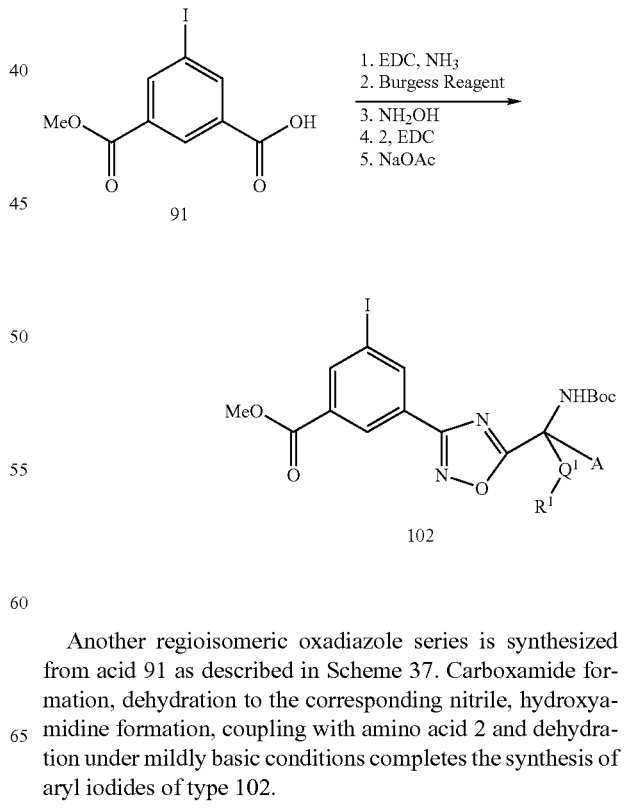

Another regioisomeric oxadiazole series is synthesized from acid 91 as described in Scheme 37. Carboxamide formation, dehydration to the corresponding nitrile, hydroxyamidine formation, coupling with amino acid 2 and dehydration under mildly basic conditions completes the synthesis of aryl iodides of type 102.

Scheme 38

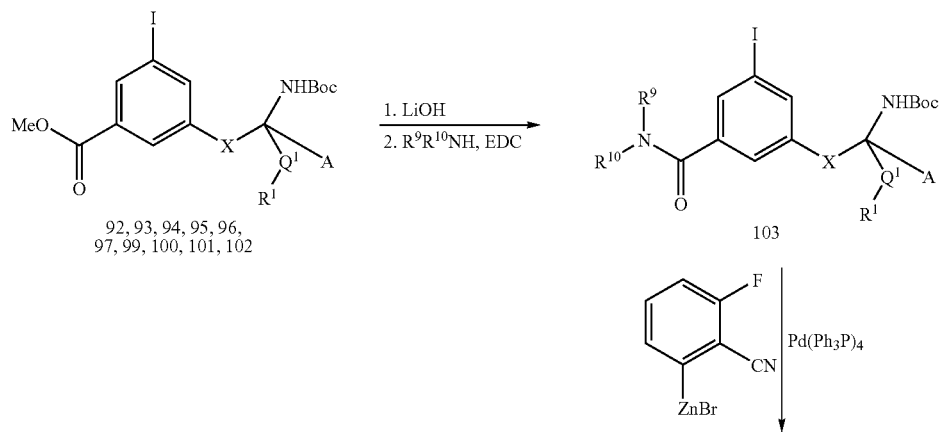

Ester hydrolysis of 92, 93, 95, 95, 96, 97, 99, 100, 101 or 102 followed by amide bond formation affords 103, as described in Scheme 38. Negishi coupling of 103 affords biaryl derivative 104. S$_N$Ar displacement of the orthofluoro substituent, followed by Boc deprotection gives compounds of type 105.

Scheme 39

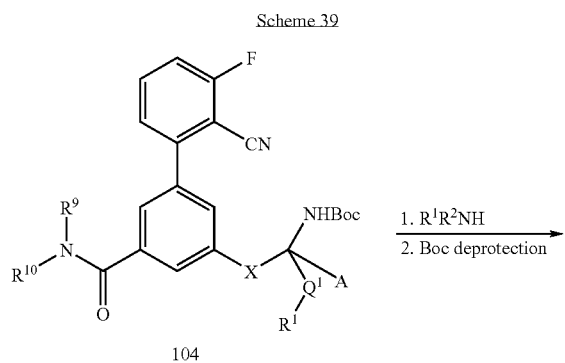

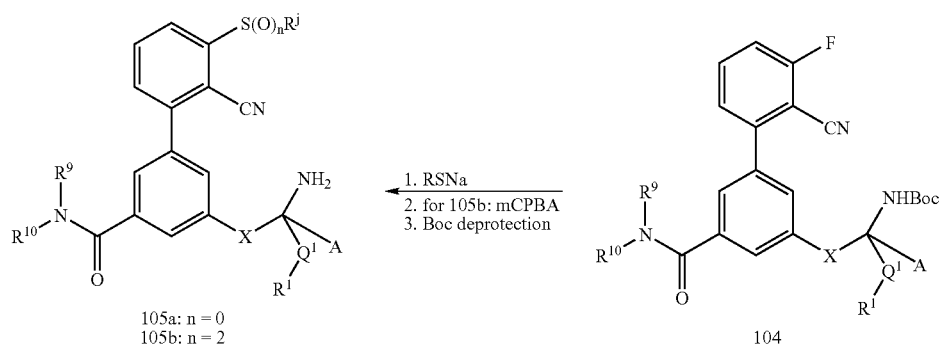

-continued

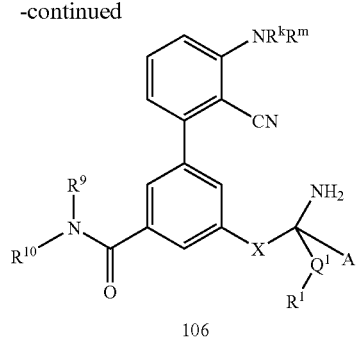

Intermediate 104 is also able to undergo S$_N$Ar substitution with amine nucleophiles, as described in Scheme 39. Removal of the amine protecting group affords compounds of type 106.

Furans of type 107 can be prepared as described in Scheme 40. Cross coupling of aryl halide 44 with a furan derivative and addition of an organometallic agent (A-MgX or A-Li) gives 108. Oxidation and treatment with a second organometallic agent gives the intermediary tertiary carbinol 109 which can undergo a Ritter reaction and deprotection to give the desired amine.

Scheme 40

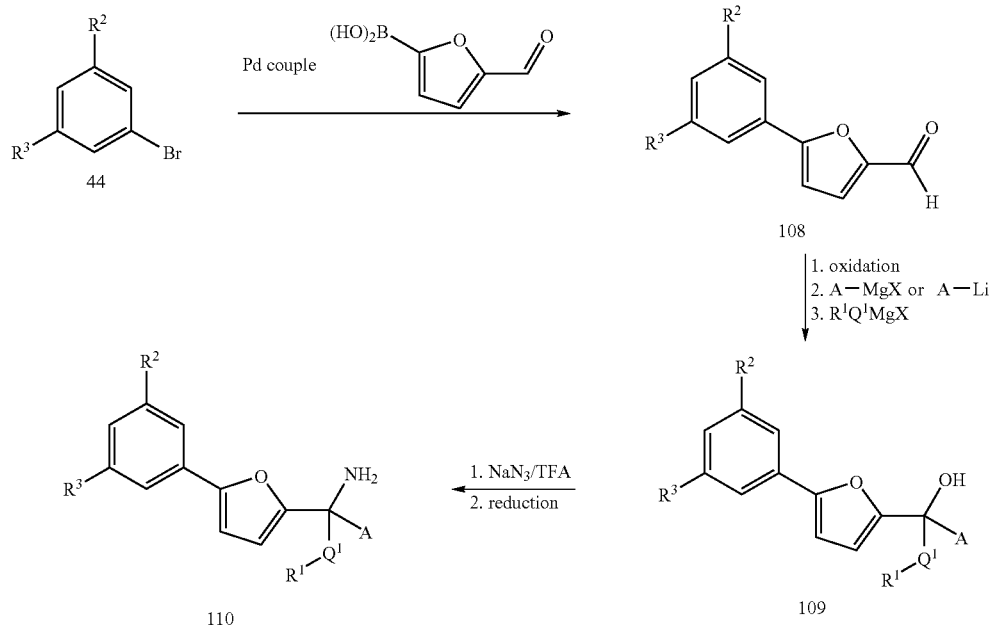

Alternatively, furans 110 (A=H) can be prepared as outlined in scheme 41. Intermediate 108 can be converted to its Ellman sulfonimine and treated with a Grignard reagent which can be deprotected to give the targeted furans.

Scheme 41

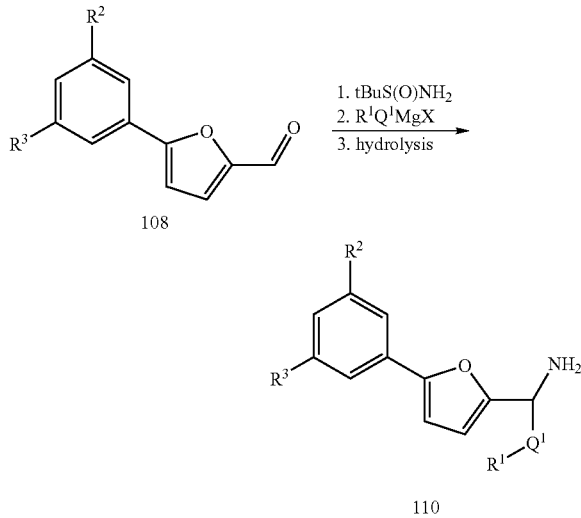

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phosphorylation inhibitors; blockers of Aβ oligomer formation; p25/CDK5 inhibitors; HMG-CoA reductase inhibitors; NK1/NK3 receptor antagonists; NSAID's including ibuprofen; vitamin E; anti-amyloid antibodies; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; neuronal nicotinic agonists; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared starting from 100 μM with three fold series dilution) are included in the reaction mixture (final DMSO concentration is 10%). All experiments are conducted at rt using the standard reaction conditions described above. To determine the IC$_{50}$ of the compound, a four parameter equation is used for curve fitting. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by ECL) are included in the reaction mixture (final DMSO concentration is 10%). All experiments are conducted at rt using the standard reaction conditions described above. To determine the IC$_{50}$ of the compound, four parameters equation is employed for curve fitting. The errors in reproducing the dissociation constants are typically less than two-fold.

In particular, the compounds of the following examples had activity in inhibiting the beta-secretase enzyme in one or both of the aforementioned assays, generally with an IC$_{50}$ from about 1 nM to 100 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate I

N-(tert-butoxycarbonyl)-α-methyl-D-phenylalanine

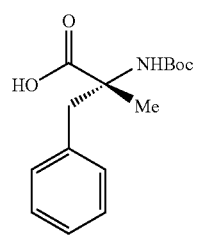

To a slurry of α-methyl-D-phenylalanine (1.00 g, 5.58 mmol) in 20 mL dioxane was added 3N NaOH (7.4 mL, 22.32 mmol) and Boc$_2$O (1.28 g, 5.86 mmol). The reaction was allowed to proceed for 14 h. The pH was lowered to ~1 by adding 1N HCl dropwise, diluted with water, and the aqueous layer was extracted with EtOAc (3×). Dried combined organics over Na$_2$SO$_4$, filtered and concentrated to obtain the desired product as a white foam. This was used without further purification. $^1$H NMR (d$_4$-MeOH, 400 Mhz) δ 7.25-7.17 (m, 3H), 7.12 (d, J=6.6 Hz, 2H), 3.27 (d, J=13.4 Hz, 1H), 3.15 (d, J=13.4 Hz, 1H), 1.45 (s, 9H), 1.39 (s, 3H). LCMS [(M-Boc)+H]$^+$=180

Intermediate II

N-(tert-butoxycarbonyl)-α-methyl-D-phenylalanine hydrazide

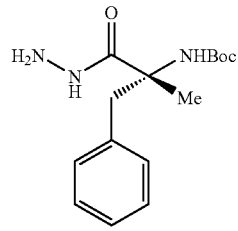

To a solution of N-Boc-α-methyl-D-phenylalanine (1.50 g, 5.37 mmol) in 25 mL CH$_3$CN was added EDC (1.75 g, 9.13 mmol), followed by hydrazine (0.421 mL, 13.43 mmol). A white precipitate formed immediately, and the solution gradually turned clear over 1 h. The reaction was allowed to proceed at rt overnight, when it was quenched by the addition of saturated aqueous NaHCO$_3$ solution, and diluted with EtOAc. The layers were separated, and the aqueous layer washed with fresh EtOAc (3×). The combined organic layers were dried over Na$_2$SO$_4$, filtered and concentrated to afford a white foam, which was used without further purification. $^1$H NMR (d$_4$-MeOH, 400 MHz) δ 7.27-7.20 (m, 3H), 7.11 (d, J=7.7 Hz, 2H), 3.30 (d, J=13.5 Hz, 1H), 3.02 (d, J=13.5 Hz, 1H), 1.46 (s, 9H), 1.31 (s, 3H). LCMS [[(M-Boc)+H]$^+$=194

Intermediate III 3-(methoxycarbonyl)-5-[methyl(methylsulfonyl)amino]benzoic acid

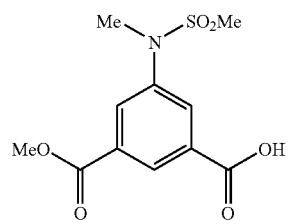

Step A: Sulfonylation

To a stirred slurry of dimethyl 5-aminoisophthalate (5.0 g, 23.90 mmol) in 100 mL CH$_2$Cl$_2$/pyridine (3:1) at 0° C. was added methanesulfonyl chloride (1.85 mL, 23.90 mmol). The resulting mixture was stirred for 4 h at rt. The solvent was removed in vacuo and ethyl acetate (100 mL) was added resulting in precipitate formation. The product was collected by filtration to give the sulfonamide as a white solid. 1H NMR (DMSO$_{d6}$, 400 MHz) δ 8.15 (s, 1H), 8.02 (s, 2H), 3.89 (s, 6H), 3.02 (s, 3H) LCMS [M-OCH$_3$]$^+$=256.16.

Step B: Methylation

To a solution of sodium hydride (0.153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with H$_2$O (100 mL) and extracted with EtOAc (3×50 mL). The organic extracts were dried over MgSO$_4$ and evaporated to give the product. $^1$H NMR (DMSO$_{d6}$, 400 MHz) δ 8.40 (s, 1H), 8.19 (s, 2H), 3.91 (s, 6H), 3.34 (s, 3H), 3.01 (s, 3H). LCMS [M+H]=302.15.

Step C: Hydrolysis

Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to RT over 8 hours. The solution was acidified with 1N HCl (30 mL) and extracted with EtOAc (3×50 mL). The combined organic extracts were washed with brine and dried over MgSO$_4$, filtered and concentrated in vacuo. Purification by silica gel chromatography (5% MeOH/CHCl$_3$ containing 1% HOAc) gave the mono acid. $^1$H NMR (DMSO$_{d6}$, 400 MHz) δ 8.30 (s, 1H), 8.10 (s, 2H), 3.84 (s, 3H), 3.27 (s, 3H), 2.94 (s, 3H). LCMS (M+H)=288.16.

Intermediate IV (R)-Methyl-3-({2-[2-(tert-butylcarbamate)-2-methyl-3-phenylpropanoyl]hydrazino}carbonyl)-5-[methyl (methylsulfonyl)amino]benzoate

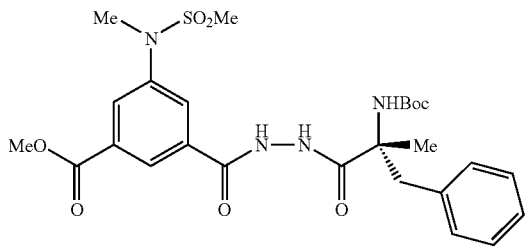

To a slurry of Intermediate II (1.95 g, 6.65 mmol) and Intermediate III (1.91 g, 6.65 mmol) in 24 mL CH$_2$Cl$_2$ was added diisopropylethylamine (3.50 mL, 19.94 mmol), followed by BOP-reagent (3.53 g, 7.98 mmol). After 90 min. at rt, the reaction was loaded directly onto a silica gel column equilibrated with 40% EtOAc/hexanes, and purified using normal phase chromatography (40->90% EtOAc/hexanes). The desired product was obtained as a white foam. $^1$H NMR (CDCl$_3$, 400 MHz) δ 9.41 (br s, 1H), 9.09 (br s, 1H), 8.34 (s, 1H), 8.26 (app. t, J=1.5 Hz, 1H), 8.06 (app t, J=1.7 Hz), 7.29-7.23 (m, 3H), 7.16 (d, J=6.4 Hz, 2H), 3.94 (s, 3H), 3.54 (d, J=8.0 Hz, 1H), 3.36 (s, 3H), 3.07 (d, J=8.0 Hz, 1H), 2.87 (s, 3H), 1.48 (s, 9H), 1.45 (s, 3H). LCMS [(M-Boc)+H]$^+$=463.

Intermediate V 3-(5-{(1R)-1-[(tert-butoxycarbonyl)amino]-1-methyl-2-phenylethyl}-1,3,4-oxadiazol-2-yl)-5-[methyl (methylsulfonyl)amino]benzoic acid methyl ester

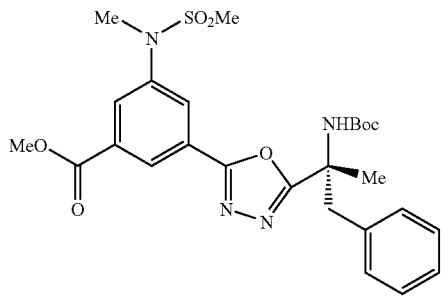

To a solution of Intermediate IV (0.520 g, 0.924 mmol) in 4 mL 1,2-dichloroethane was added Burgess reagent (0.661 g, 2.77 mmol). The slurry was microwaved at 120° C. for 8 minutes. The reaction mixture was loaded directly onto a silica gel column equilibrated with 20% EtOAc/hexanes, and purified using normal phase chromatography (20->70% EtOAc/hexanes) to afford the desired oxadiazole as a white foam. $^1$H NMR (CDCl$_3$, 400 MHz) δ 8.53 (app. t, J=1.5 Hz, 1H), 8.24 (app. t, J=0.6 Hz, 1H), 8.06 (m, 1H), 7.30-7.22 (m, 3H), 7.14-7.05 (m, 2H), 3.97 (s, 3H), 3.59 (d, J=13.5 Hz, 1H), 3.42 (d, J=13.5 Hz, 1H), 3.40 (s, 3H), 2.91 (s, 3H), 1.71 (s, 3H), 1.41 (s, 9H). LCMS [M+H]$^+$=545.

Intermediate VI 3-(5-{(1R)1-[(tert-butoxycarbonyl)amino]-1-methyl-2-phenylethyl}-1,3,4-oxadiazol-2-yl)-5-[methyl(methylsulfonyl)amino]benzoic acid

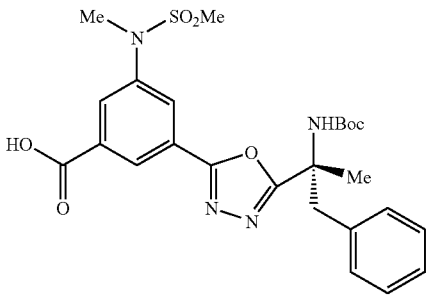

To a solution of Intermediate V (0.114 g, 0.209 mmol) from Step A in 2.5 mL THF was added 1N LiOH (0.63 mL, 0.630 mmol). After 2 h at rt, the reaction was quenched by the addition of 1N HCl (0.840 mL, 0.840 mmol) and diluted with EtOAc and H$_2$O. The layers were separated, and the aqueous layer was extracted with EtOAc (3×). The combined organics were dried over Na$_2$SO$_4$, filtered and concentrated to afford the desired acid as a white foam. The acid was used without further purification. $^1$H NMR (CDCl$_3$, 400 MHz) δ 8.56 (s, 1H), 8.28 (app. d, J=1.2 Hz, 1H), 8.06 (app. t, J=1.8 Hz, 1H), 7.29-7.25 (m, 3H), 7.07 (d, J=6.0 Hz, 2H), 3.60 (d, J=13.3 Hz, 1H), 3.40 (d, J=13.3 Hz, 1H), 3.40 (s, 3H), 2.92 (s, 3H), 1.70 (s, 3H), 1.39 (s, 9H). LCMS [M+H]$^+$=531.

Intermediate VII 3-({[(1R)-1-(4-fluorophenyl)ethyl]amino}carbonyl)-5-[methyl(methylsulfonyl)amino]benzoic acid

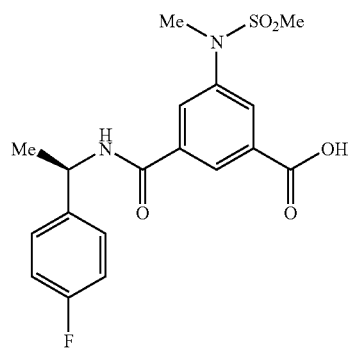

Step A: Amine Coupling

To a slurry of Intermediate III (8.00 g, 27.85 mmol) in 50 mL CH$_2$Cl$_2$ was added EDC (6.94 g, 36.2 mmol), HOAt (0.758 g, 5.57 mmol) and (R)-1-(4-fluorophenyl)ethanamine (4.51 mL, 33.42 mmol). The reaction was allowed to proceed at rt for 50 h, then diluted with H$_2$O and EtOAc. The layers were separated, and the aqueous washed with EtOAc (3×). The combined organics were washed with brine, dried over Na$_2$SO$_4$, filtered and concentrated. The residue was purified by chromatography on silica gel (90->100% EtOAc/Hexanes) to afford the benzyl amide as a white solid. $^1$H NMR (CDCl$_3$, 400 MHz) δ 8.26 (s, 1H), 8.17 (s, 1H), 8.06 (s, 1H), 7.31 (m, 5H), 6.50 (d, J=7.1 Hz, 1H), 5.33 (q, J=7.1 Hz, 1H), 3.96 (s, 3H), 3.37 (s, 3H), 2.88 (s, 3H), 1.64 (d, J=7.0 Hz, 3H). LCMS [M+H]$^+$=409.

Step B: Ester Hydrolysis

To a solution of ester (10.0 g, 24.48 mmol) from step A in 200 mL THF was added LiOH (1.76 g, 73.44 mmol) in 70 mL H$_2$O. After 5 h at rt, the reaction was concentrated, and the residue was partitioned between H$_2$O and CH$_2$Cl$_2$. The layers were separated, and 100 mL 1N HCl was added to the aqueous layer, resulting in the formation of a white suspension. The aqueous layer was extracted with ~4:1 CH$_2$Cl$_2$/THF (3×). The combined organics were dried over Na$_2$SO$_4$, filtered and concentrated to afford 3-({[(1R)-1-(4-fluorophenyl)ethyl]amino}carbonyl)-5[methyl(methylsulfonyl)amino]benzoic acid as a white solid, which was used without further purification. $^1$H NMR (d$_4$-MeOH, 400 MHz) δ 9.02 (d, J=7.3 Hz, 1H), 8.39 (s, 1H), 8.24 (t, J=1.4 Hz, 1H), 8.06 (t, J=2.0 Hz, 1H), 7.43-7.39 (m, 2H), 7.07-7.02 (m, 2H), 5.24 (q, J=7.1 Hz, 1H), 3.37 (s, 3H), 2.94 (s, 3H), 1.56 (d, J=7.1 Hz, 3H). LCMS [M+H]$^+$=395.

Intermediate VIII tert-butyl[(1R)-2-amino-1-benzyl-2-(hydroxyimino)-1-methylethyl]carbamate

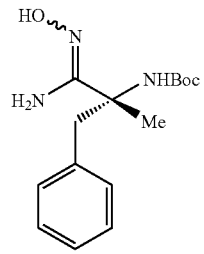

Step A: Carboxamide Formation

To a solution of N-Boc-α-methyl-D-phenylalanine (2.04 g, 7.30 mmol) in 26 mL CH$_2$Cl$_2$ was added EDC (1.54 g, 8.03 mmol), followed by HOAt (0.845 g, 6.21 mmol). After 30 min at rt, 15 mL DMF was added; the reaction was cooled to −10° C., and gaseous ammonia was bubbled through the reaction for 50 min. The reaction was quenched by the addition of satd. aqueous NaHCO$_3$ and diluted with EtOAc. The layers were separated, and the aqueous layer washed with fresh EtOAc (2×). The combined organics were washed with aqueous 3M LiCl and brine, dried over Na$_2$SO$_4$, filtered and concentrated. The residue was purified by normal phase chromatography (0->6% MeOH/CH$_2$Cl$_2$) to afford the desired carboxamide as a white solid. $^1$H NMR (d$_4$-MeOH, 400 MHz) δ 7.96 (br s, 1H), 7.28-7.13 (m, 3H), 7.12 (d, J=7.4 Hz, 2H), 6.39 (br s, 1H), 5.81 (br s, 1H), 3.32 (d, J=13.7 Hz, 1H), 3.10 (d, J=13.7 Hz, 1H), 1.44 (s, 9H), 1.40 (s, 3H). LCMS [(M-Boc)+H]$^+$=179.

Step B: Dehydration

To a slurry of carboxamide (0.311 g, 1.12 mmol) from Step A in 3 mL 1,2-dichloro ethane was added Burgess reagent (0.533 g, 2.23 mmol), and the heterogeneous reaction medium was microwaved at 100° C. for 5 min. The reaction was loaded directly onto a silica gel column equilibrated with 100% hexanes, and purification by normal phase chromatography (0->25% EtOAc/hexanes) afforded the desired nitrile as a white foam. $^1$H NMR (CDCl$_3$, 400 MHz) δ 7.36-7.31 (m, 3H), 7.25-7.24 (m, 2H), 4.56 (br s, 1H), 3.29 (d, J=13.5 Hz, 1H), 3.15 (d, J=13.5 Hz, 1H), 1.58 (s, 3H), 1.53 (s, 9H). LCMS [M+H]$^+$=260.

Step C: Hydroxy Amidate Formation

To a solution of nitrile (0.069 g, 0.265 mmol) in 1.50 mL i-PrOH and 0.40 mL H$_2$O was added hydroxylamine hydrochloride (0.184 g, 2.65 mmol) and K$_2$CO$_3$ (0.183 g, 1.325 mmol). The sealed vessel was microwaved at 130° C. for 6 min. The reaction was concentrated, the residue was redissolved in 0.85 mL DMF and filtered through a pad of cotton wool to remove insoluble residue, and the filtrate was purified by preparative HPLC (5->95% CH$_3$CN/H$_2$O, 0.1% added TFA, C18 PRO YMC 20×150 mm) to afford tert-butyl[(1R)-2-amino-1-benzyl-2-(hydroxyimino)-1-methylethyl]carbamate as a viscous oil and one geometrical isomer by $^1$H NMR. $^1$H NMR (d$_4$-MeOH, 400 MHz) δ 7.34-7.29 (m, 3H), 7.26-7.14 (m, 2H), 3.32-3.28 (m, 2H), 3.15 (d, J=13.0 Hz, 1H), 1.46 (s, 9H), 1.43 (s, 3H). LCMS [M+H]$^+$=294.

Intermediate IX 3-amino-N-[(1R)-1-(4-fluorophenyl)ethyl]-5-[methyl(methylsulfonyl)amino]benzamide

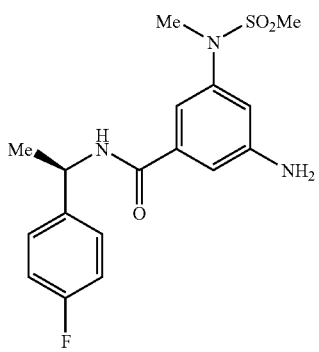

Step A: Methyl Ester Formation

To 3-amino-5-nitro benzoic acid (3.60 g, 19.78 mmol) in 100 mL MeOH was added thionyl chloride (2.59 g, 21.76 mmol). The solution was heated to 65° C. for 12 h. Concentration in vacuo afforded the methyl ester hydrochloride salt. $^1$H NMR (d$_4$-MeOH, 400 MHz) δ 8.62 (s, 1H), 8.28 (s, 1H), 8.19 (s, 1H), 3.99 (s, 3H).

Step B: Mesylation

To a solution of 3.53 g (18.0 mmol) amino ester from step A in 100 mL CH$_2$Cl$_2$/pyridine (3:1) was added methanesulfonyl chloride (2.07 g, 18.0 mmol). The reaction was stirred at ambient temperature for 1 h followed by evaporation of the solvent. The gummy residue was taken up in EtOAc (100 mL), acidified with 1N HCl (100 mL), and extracted with EtOAc (3×100 mL). The combined organic extracts were dried over MgSO$_4$, filtered, and concentrated in vacuo to give the sulfonamide as an off-white solid. $^1$H NMR (d$_4$-MeOH, 400 MHz) δ 8.46 (s, 1H), 8.30 (s, 1H), 8.18 (s, 1H), 3.97 (s, 3H), 3.09 (s, 3H).

Step C: Methylation

Sodium hydride (0.26 g, 6.55 mmol, 60% oil dispersion) was suspended in 10 mL DMF to which 1.5 g (5.45 mmol) of the sulfonamide from step B (in 10 mL DMF) was added followed by 0.93 g (6.55 mL) methyl iodide. The solution was stirred at ambient temperature for 3 h. The reaction was quenched with H$_2$O (250 mL), extracted with EtOAc (3×200 mL), dried over MgSO$_4$, filtered and concentrated in vacuo. Purification by silica gel chromatography provided the N-methyl sulfonamide. LCMS (M–H$_2$0)=272.2.

Step D: Ester Hydrolysis

To a solution of methyl ester (6.47 g, 22.44 mmol) obtained from Step C in 20 mL THF and 20 mL MeOH was added 2N NaOH (13.74 mL, 27.49 mmol). After 1.5 h at rt, the reaction was acidified with 1N HCl until the pH was below 1, then diluted with EtOAc and H$_2$O. The layers were separated, the aqueous layer washed with fresh EtOAc (1×), the combined organics were dried over MgSO$_4$, filtered and concentrated to obtain the desired acid as a yellowish foam. This was used without further purification. $^1$H NMR (CDCl$_3$, 400 MHz) δ 8.80 (t, J=1.4 Hz, 1H), 8.47 (t, J=2.2 Hz, 1H), 8.40 (t, J=1.3 Hz, 1H), 3.44 (s, 3H), 2.95 (s, 3H).

Step E: Amine Coupling

To a slurry of acid (1.70 g, 6.20 mmol) in 18 mL CH$_2$Cl$_2$ was added EDC (1.78 g, 9.30 mmol), HOAt (0.478 g, 3.10 mmol) and (R)-1-(4-fluorophenyl)ethanamine (1.0 mL, 7.44 mmol). The reaction was allowed to proceed at rt for 65 h, then diluted with brine and EtOAc. The layers were separated, and the aqueous washed with EtOAc. The combined organics were dried over MgSO$_4$, filtered and concentrated. The residue was purified by chromatography on silica gel (20->55% EtOAc/Hexanes) afforded the benzyl amide as a yellow foam. $^1$H NMR (CDCl$_3$, 400 MHz) δ 8.42 (t, J=1.6 Hz, 1H), 8.33 (t, J=2.0 Hz, 1H), 8.15 (t, J=1.9 Hz, 1H), 7.38-7.34 (m, 2H), 7.07-7.04 (m, 2H), 6.52 (d, J=7.3 Hz, 1H), 5.29 (q, J=7.0 Hz, 1H), 3.39 (s, 3H), 2.90 (s, 3H), 1.62 (d, J=7.0 Hz, 3H). LCMS [M+H]=396.

Step F: Nitro Reduction

To a solution of nitrobenzene (2.07 g, 5.24 mmol) obtained from Step E in 30 mL EtOH was added 10% Pd/C (0.557 g, 0.524 mmol). The reaction vessel was evacuated, and opened to a balloon of hydrogen (3×), and the reaction was allowed to proceed under an atmosphere of hydrogen for 16 h. The flask was then evacuated, and opened to argon (3×), the palladium was removed via filtration through celite, and the filtrate was concentrated to yield 3-amino-N-[(1R)-1-(4-fluorophenyl)ethyl]-5-[methyl(methylsulfonyl)amino]benzamide as a white foam, which was used without further purification. $^1$H NMR (CDCl$_3$, 400 MHz) δ 7.34-7.31 (m, 2H), 7.07 (s, 1H), 7.07-7.02 (m, 2H), 7.93 (s, 1H), 6.81 (t, J=1.8 Hz, 1H), 6.27 (d, J=7.5 Hz, 1H), 5.25 (q, J=7.1 Hz, 1H), 3.27 (s, 3H), 2.82 (s, 3H), 1.56 (d, J=7.0 Hz, 3H). LCMS [M+H]=366.

Intermediate X 3-bromo-N-[(1R)-1-(4-fluorophenyl)ethyl]-5-[methyl(methylsulfonyl)amino]benzamide

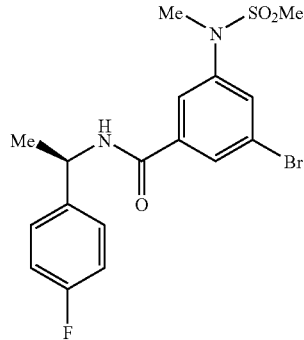

To a solution of 3-amino-N-[(1R)-1-(4-fluorophenyl)ethyl]-5-[methyl(methylsulfonyl)amino]benzamide (Intermediate IX) (0.510 g, 1.40 mmol) from Step F in 10 mL CH$_3$CN at 0° C. was added 48% (wt/wt) HBF$_4$ (0.236 mL, 1.814 mmol) After 10 min, the reaction was warmed to rt for 30 min. The reaction was cooled back to 0° C., tert-butyl nitrite (0.234 mL, 1.95 mmol) was added, and the reaction vessel was wrapped in aluminum foil and stirred at 0° C. for 1 h. The reaction was added via pipette into a rapidly stirring slurry of CuBr (2.00 g, 13.96 mmol) and CuBr$_2$ (3.90 g, 17.45 mmol) in 10 mL H$_2$O, rinsing with 4 mL CH$_3$CN. After 45 min, the reaction was quenched by the addition of satd. aqueous NaHCO$_3$ and diluted with H$_2$O and EtOAc. The layers were separated, and the aqueous layer washed with fresh EtOAc (2×). The combined organics were washed with brine (2×), and dried over Na$_2$SO$_4$ for 16 h to precipitate out remaining copper salts. The organic layers were filtered, concentrated, and the resulting residue was purified by silica gel chromatography (20->60% EtOAc/hexanes) to obtain 3-bromo-N-[(1R)-1-(4-fluorophenyl)ethyl]-5-[methyl(methylsulfonyl)amino]benzamide as a white foam. ¹H NMR (CDCl₃, 400 MHz) δ 7.73-7.70 (m, 2H), 7.59 (t, J=1.8 Hz, 1H), 7.35-7.32 (m, 2H), 7.04-6.98 (m, 2H), 6.56 (d, J=7.5 Hz, 1H), 5.25 (q, J=7.0 Hz, 1H), 3.28 (s, 3H), 2.86 (s, 3H), 1.57 (d, J=7.0 Hz, 3H). LCMS [M+H]=429 and 431.

Intermediate XI 3-cyano-N-[(1R)-1-(4-fluorophenyl)ethyl]-5-[methyl(methylsulfonyl)amino]benzamide

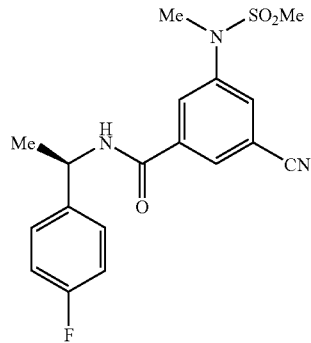

To a solution of 3-bromo-N-[(1R)-1-(4-fluorophenyl)ethyl]-5-[methyl(methylsulfonyl)amino]benzamide (Intermediate X) (0.033 g, 0.077 mmol) in 0.80 mL degassed DMF (degassed by bubbling a stream of argon through solvent for 5 min) was added Zn(CN)₂ (0.011 g, 0.092 mmol) and Pd(PPh₃)₄ (0.009 g, 0.008 mmol). The reaction vessel was purged thoroughly with argon, then sealed and microwaved at 180° C. for 30 min. The reaction was diluted with EtOAc, and the organics were washed with 3M aqueous LiCl. The aqueous washed with fresh EtOAc (2×), the combined organics were washed with brine, dried over Na₂SO₄, filtered and concentrated. The residue was purified by silica gel chromatography (5->75% EtOAc/hexanes) to afford 3-cyano-N-[(1R)-1-(4-fluorophenyl)ethyl]-5-[methyl(methylsulfonyl)amino]benzamide as a white foam. ¹H NMR (CDCl₃, 400 MHz) δ 8.04 (t, J=2.0 Hz, 1H), 7.91 (t, J=1.3 Hz, 1H), 7.78 (t, J=1.5 Hz, 1H), 7.36-7.7.31 (m, 2H), 7.05-7.00 (m, 2H), 6.67 (d, J=7.5 Hz, 1H), 5.25 (q, J=7.1 Hz, 1H), 3.34 (s, 3H), 2.87 (s, 3H), 1.59 (d, J=7.0 Hz, 3H). LCMS [M+H]⁺=376.

Intermediate XII

3-[-amino(hydroxyimino)methyl]-N-[(1R)-1-(4-fluorophenyl)ethyl]-5-[methyl(methylsulfonyl)amino]benzamide

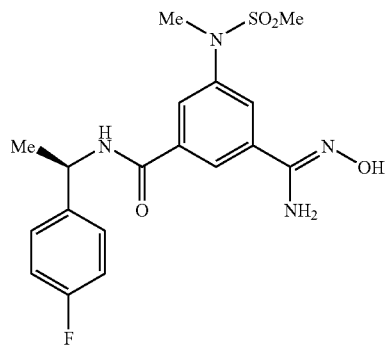

To a solution of 3-cyano-N-[(1R)-1-(4-fluorophenyl)ethyl]-5-[methyl(methylsulfonyl)amino]benzamide (Intermediate XI) (0.033 g, 0.088 mmol) in 0.80 mL i-PrOH and 0.10 mL H₂O was added K₂CO₃ (0.007 g, 0.053 mmol). The vessel was sealed and microwaved at 130° C. for 5 min. The reaction was concentrated, the residue was redissolved in DMF and purified by preparative HPLC (5->95% CH₃CN/H₂O, 0.1% added TFA, C18 PRO YMC 20×150 mm) to afford 3-[-amino(hydroxyimino)methyl]-N-[(1R)-1-(4-fluorophenyl)ethyl]-5-[methyl(methylsulfonyl)amino]benzamide as a viscous oil. ¹H NMR (d₄-MeOH, 400 MHz) δ 8.98 (d, J=7.5 Hz), 8.19 (t, J=1.7 Hz, 1H), 8.07 (t, J=1.4 Hz, 1H), 7.90 (t, J=1.8 Hz, 1H), 7.43-7.39 (m, 2H), 7.07-7.01 (m, 2H), 5.25 (m, 1H), 3.38 (s, 3H), 2.98 (s, 3H), 1.56 (d, J=7.1 Hz, 3H). LCMS [M+H]⁺=409.

Intermediate XIII ethyl-3-({[(1R)-1-(4-fluorophenyl)ethyl]amino}carbonyl)-5-[methyl(methylsulfonyl)amino]benzenecarboximidoate

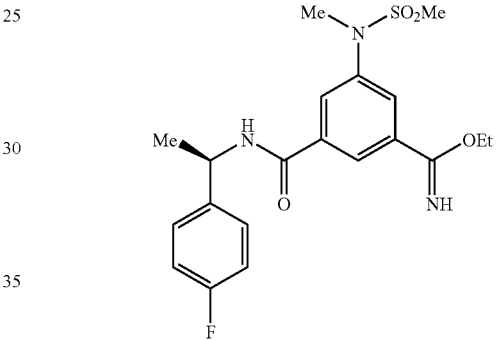

Gaseous HCl was bubbled through a solution of 3-[-amino(hydroxyimino)methyl]-N-[(1R)-1-(4-fluorophenyl)ethyl]-5-[methyl(methylsulfonyl)amino]benzamide (0.038 g, 0.090 mmol) (Intermediate XI) in 1 mL CH₂Cl₂ and 1 mL EtOH at 0° C. for 2 min. After stirring at 0° C. for 2.5 h, the reaction was warmed to rt for 18 h. Concentrated, redissolved residue in 4 mL Et₂O, cooled to 0° C. and bubbled ammonia through reaction for 1 min. Concentrated and used without further purification for next step.

Intermediate XIV

3-[(Z)-2-(2-methylcyclopropyl)vinyl]-5-[methyl(methylsulfonyl)amino]benzoic acid

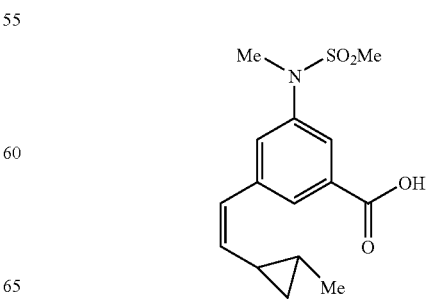

Step A: Iodination

3-Nitrobenzoate (35.3 g, 195 mmol) in triflic acid (100 mL) at 0° C. was added NIS (43.8 g, 195 mmol) in ten portions. Remove ice bath and stir for 48 hrs. The reaction typically goes to 50% completion. At this time more NIS could be added or cool to 0° C. and quench with careful dropwise addition of water. The mixture was extracted three times with EtOAc (250 mL) and the combined extracts were washed with a 10% NaHSO$_3$ solution, followed by water. The organics were dried over Na$_2$SO$_4$, concentrated, and purified on silica gel (10% EtOAc in Hex) affording 24.1 g.

Step B: Nitro Reduction

Tin chloride (88.6 g, 392 mmol) in EtOH (50 mL) was refluxed and the nitrobenzoate from step A (24.1 g, 78.4 mmol) in 1:1 THF:EtOH (100 mL), was added dropwise. The reaction mixture was refluxed for 30 minutes then cooled to 0° C. The resulting solution was basified to pH 8-9 with aq. Na$_2$CO$_3$. The aqueous layer was extracted three times with EtOAc (700 mL) and the combined extracts were washed with saturated NaHCO$_3$ then brine. The organics were dried over Na$_2$SO$_4$ and concentrated to afford 21.7 g of the crude aniline which was used without further purification.

Step C: Mesylation

To a 0° C. solution of aniline from step B (21.7 g, 78.3 mmol) in 3:1 CH$_2$Cl$_2$:pyridine (75 mL) was added methanesulfonyl chloride (6.36 mL, 82.2 mmol). The ice bath was removed after 15 min and the solution was stirred overnight at rt. The reaction mixture was extracted several times with 1N HCl. The organic phase was dried, concentrated, and chromatographed (1:1 EtOAc:Hex) to afford 25.2 g of the desired sulfonamide as a white solid.

Step D: Methylation

The sulfonamide from step C (23.6 g, 66.5 mmol) in DMF (75 mL) at 0° C. was treated with 60% NaH (2.92 g, 73.1 mmol). The solution stirred for 30 minutes before MeI (4.55 mL, 73.1 mmol) was added. The ice bath was removed and the solution was stirred at rt for twelve hours. The reaction was quenched with saturated NH$_4$Cl solution and extracted three times with EtOAc (150 mL). The combined organic were washed with water (5×50 mL), dried, concentrated to afford 25.3 g of the desired methylated anilide which was used without further purification.

Step E: Oxidation

Trans-2-methylcyclopropanemethanol (7.0 g, 81 mmol) was added to a solution of PCC (28 g, 130 mmol) in CH$_2$Cl$_2$ (225 mL). The solution became black and was stirred for three hours at rt. The reaction mixture was diluted with ether (250 mL) and decanted. The liquid solution was filtered through a 4 inch plug of Florisil and the solvent was removed by distillation through a Vigreux column to afford 10 g of the desired aldehyde.

Step F: Corey-Fuchs Reaction

To a solution of PPh$_3$ (12.4 g, 47.5 mmol) in CH$_2$Cl$_2$ (100 mL) at 0 C was added CBr$_4$ (7.88 g, 23.7 mmol). The reaction mixture was stirred for 10 minutes then treated with the carboxaldehyde from step E (1.0 g, 12 mmol). The solution was stirred for 30 min at 0° C. then 1 hr at rt. Hexane was added and the solids were filtered, and the filtrate was concentrated to afford 4.4 g of the dibromide.

Step G: Alkyne Formation

The dibromide from step F (15.4 g, 64.1 mmol) in 60 mL of cyclohexane at −78° C. was treated with 2.0 M n-BuLi in cyclohexane (64.1 mL, 128 mmol). The resulting reaction mixture was stirred at −78° C. for 1 hr then warmed to rt where it was stirred for 2 hr. The reaction was quenched with water and extract with cyclohexane (3×25 mL). The product was purified by distillation (bp=69-72 C).

Step H: Coupling

A 100 mL 3-neck round bottom flask was charged with InCl$_3$ (0.829 g, 10.4 mmol) and dried under vacuum with a heat gun for 2 min. THF (16 mL) was added under nitrogen and the flask was immersed in a −78° C. ice bath. DIBAL-H (12.4 mL, 1M in hexanes) was then added dropwise and the resulting solution was stirred for 30 min at −78° C. After this time, the acetylene from step G (10.4 mmol) was added followed by 1.0 M Et$_3$B (1.6 mL, 1M in hexanes). This reaction mixture was stirred at −78° C. for 2.5 hr then warmed to rt. DMI (12 mL) and aryliodide from step D (1.47 g, 4.0 mmol) was added followed by a palladium trifurylphosphine complex [prepared from Pd$_2$(DBA)$_3$.CHCl$_3$ (20 mg) and trifurylphosphine (28 mg) in THF (6 mL)]. The resulting reaction mixture was heated at 60 C for 2 hr, quenched with water and extracted with ether (3×50 mL). The combined organic extracts were dried, and concentrated and the product was purified on a chiral OJ column (60:40 Hexane w/0.1% TFA: EtOH). Collection of the first peak afforded 276 mg of the desired diastereomer.

Step I: Ester Hydrolysis

To 276 mg (0.853 mmol) of the ester from step H in 10 mL THF:MeOH:water (3:1:1) was added 2 N NaOH (0.64 mL, 1.28 mmol). The solution was stirred at rt for 2 h. The reaction mixture was concentrated and acidified with 2 N HCl (10 mL) and extracted with CHCl$_3$ (3×20 mL). The combined organic extracts were dried over MgSO$_4$, filtered, and concentrated to yield 253 mg of the desired carboxylic acid. LCMS (M+H)=310.12

Intermediate XV

3-[(Z)-2-(2-methylcyclopropyl)vinyl]-5-[propyl(methylsulfonyl)amino]benzoic acid

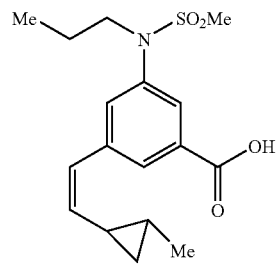

This compound was prepared analogously to Intermediate XIII, the only difference being the substitution of methyl iodide with propyl iodide in Step D.

Intermediate XVI 3-(5-((1R)-2-tert-Butoxycarbonylamino-1-phenyl-propan-2-yl)-1,3,4-oxadiazol-2-yl)-5-(1-cyanocyclopentyl)benzoic acid

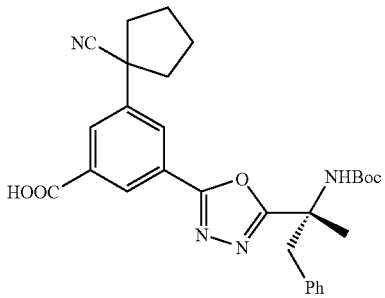

Step A: Bromination

To a solution of diethyl 5-(hydroxymethyl)benzene-1,3-dioate (3.5 g, 0.014 mol) and carbon tetrabromide (5.0 g, 0.015 mol) in 30 mL CH$_2$Cl$_2$, cooled to 0° C., was added dropwise a solution of triphenylphosphine (3.9 g, 0.015 mol) in 20 mL CH$_2$Cl$_2$. The reaction was stirred at 0° C. for 1.5 h, diluted with CHCl$_3$, and washed with water and brine. Drying, solvent evaporation and flash chromatography (silica gel, 0-30% EtOAc/hexanes) gave diethyl-5-(bromomethyl)benzene-1,3-dioate. $^1$H NMR (400 MHz, CDCl$_3$) δ 8.61 (s, 1H), 8.25 (app d, J=1.6 Hz, 2H), 4.55 (s, 2H), 4.42 (q, J=7.1 Hz, 4H), 1.42 (t, J=7.1 Hz, 6H).

Step B: Cyanation

To a solution of diethyl-5-(bromomethyl)benzene-1,3-dioate (1.9 g, 6.0 mmol) in 69 mL MeCN was added trimethylsilyl cyamide (1.2 mL, 9.0 mmol) and tetrabutylammonium fluoride (1M in THF, 9.0 mL, 9.0 mmol). The reaction was stirred for 0.5 h and concentrated. Flash chromatography (silica gel, 0-30% EtOAc/hexanes) gave diethyl 5-(cyanomethyl)benzene-1,3-dioate. $^1$H NMR (400 MHz, CDCl$_3$) δ 8.65 (s, 1H), 8.20 (app t, J=0.7 Hz, 2H), 4.43 (q, J=7.1 Hz, 4H), 3.86 (s, 2H), 1.43 (t, J=7.1 Hz, 6H).

Step C: Alkylation

To a solution of diethyl 5-(cyanomethyl)benzene-1,3-dioate (500 mg, 1.9 mmol) in 18.6 mL THF was added potassium bis(trimethylsilyl)amide (1.1 g, 5.7 mmol) and the reaction was stirred at rt for 5 min. 1,4-Dibromobutane (0.25 mL, 2.1 mmol) was added, the mixture was stirred for 45 min and then quenched with 1N HCl. Ethyl acetate was added, the layers separated and the organic layer washed with water and brine. Drying, solvent evaporation and flash chromatography (silica gel, 0->15% EtOAc/hexanes) gave diethyl 5-(1-cyanocyclopentyl)benzene-1,3-dioate. $^1$H NMR (400 MHz, CDCl$_3$) δ 8.63 (m, 1H), 8.31 (m, 2H), 4.43 (q, J=7.1 Hz, 4H), 2.56 (m, 2H), 2.14-1.99 (m, 6H), 1.43 (t, J=7.1 Hz, 6H).

Step D: Ester Hydrolysis

A solution of diethyl 5-(1-cyanocyclopentyl)benzene-1,3-dioate (0.33 g, 1.05 mmol) and NaOH (1N in H$_2$O, 0.945 mL, 0.945 mmol) in 5 mL THF and 5 mL EtOH was stirred at rt overnight. The reaction mixture was concentrated, diluted with H$_2$O and extracted with ether. The aqueous phase was made acidic with 1N HCl, extracted with EtOAc and the combined organic layers were washed with brine. Drying and solvent evaporation gave 3-(ethoxycarbonyl)-5-(1-cyanocyclopentyl)benzoic acid. $^1$H NMR (400 MHz, CD$_3$OD) δ 8.58 (m, 1H), 8.35 (m, 2H), 4.43 (q, J=7.1 Hz, 2H), 2.51 (m, 2H), 2.18 (m, 2H), 2.05 (m, 4H), 1.42 (t, J=7.1 Hz, 3H).

Step E: Coupling

A solution of 3-(ethoxycarbonyl)-5-(1-cyanocyclopentyl)benzoic acid (0.25 g, 0.87 mmol), N-(tert-butoxycarbonyl)-α-methyl-D-phenylalanine hydrazide (0.29 g, 1.0 mmol) (Intermediate II), benzotriazol-1-yloxy-tris(dimethylamino)-phosphonium hexafluorophosphate (0.57 g, 1.3 mmol) and diisopropylethylamine (0.46 mL, 2.6 mmol) in 8 mL CH$_2$Cl$_2$ was stirred at rt for 1 h. Flash chromatography (silica gel, 5-60% EtOAc/hexanes) gave ethyl 3-({2-[(R)-2-tert-butoxycarbonylamino-2-methyl-3-phenylpropanoyl]hydrazino}carbonyl)-5-(1-cyanocyclopentyl)benzoate. $^1$H NMR (400 MHz, CDCl$_3$) δ 9.45 (bs, 1H), 9.00 (d, J=4.6 Hz, 1H), 8.36 (m, 1H), 8.31 (m, 1H), 8.15 (s, 1H), 7.35-7.28 (m, 3H), 7.18 (d, J=6.6 Hz, 2H), 4.72 (s, 1H), 4.43 (q, J=7.1 Hz, 2H), 3.57 (d, J=13.6 Hz, 1H), 3.09 (d, J=13.7 Hz, 1H), 2.56 (m, 2H), 2.15-1.97 (m, 6H), 1.50 (s, 9H), 1.47 (s, 3H), 1.43 (t, J=7.1 Hz, 3H).

Step F: Dehydrative Cyclization

A solution of ethyl 3-({2-[(R)-2-tert-butoxycarbonylamino-2-methyl-3-phenylpropanoyl]hydrazino}carbonyl)-5-(1-cyanocyclopentyl)benzoate (0.10 g, 0.18 mmol) and (methoxycarbonylsulfamoyl)triethylammonium hydroxide, inner salt (0.13 g, 0.54 mmol) in 1.5 mL dichloroethane was heated in the microwave at 120° C. for 8 min. Concentration and flash chromatography (silica gel, 0-45% EtOAc/hexanes) gave ethyl 3-(5-((R)-2-tert-butoxycarbonylamino-1-phenyl-propan-2-yl)-1,3,4-oxadiazol-2-yl)-5-(1-cyanocyclopentyl)benzoate. $^1$H NMR (400 MHz, CDCl$_3$) δ 8.57 (app t, J=1.5 Hz, 1H), 8.30 (d, J=1.5 Hz, 2H), 7.29 (m, 3H), 7.08 (m, 2H), 5.11 (br s, 1H), 4.46 (q, J=7.1 Hz, 2H), 3.60 (d, J=13.6 Hz, 1H), 3.44 (d, J=13.6 Hz, 1H), 2.59 (m, 2H), 2.19-1.99 (m, 6H), 1.74 (s, 3H), 1.45 (t, J=7.1 Hz, 3H), 1.43 (s, 9H).

A solution of ethyl 3-(5-((R)-2-tert-butoxycarbonylamino-1-phenylpropan-2-yl)-1,3,4-oxadiazol-2-yl)-5-(1-cyanocyclopentyl)benzoate (0.17 g, 0.31 mmol) and LiOH.H$_2$O (65 mg, 1.55 mmol) in 8.1 mL THF and 3.1 mL H$_2$O was stirred at rt overnight. The reaction was concentrated, diluted with H$_2$O, made acidic with 10% citric acid solution and extracted with EtOAc. The combined organic layers were washed with brine. Drying and solvent evaporation gave 3-(5-((R)-2-tert-butoxycarbonylamino-1-phenylpropan-2-yl)-1,3,4-oxadiazol-2-yl)-5-(1-cyanocyclopentyl)benzoic acid. $^1$H NMR (400 MHz, CDCl$_3$) δ 8.62 (bs, 1H), 8.36 (d, J=1.4 Hz, 2H), 7.28 (m, 3H), 7.09 (d, J=5.7 Hz, 2H), 5.22 (bs, 1H), 3.61 (d, J=13.4 Hz, 1H), 3.43 (m, 1H), 2.60 (m, 2H), 2.20-2.01 (m, 6H), 1.75 (s, 3H), 1.42 (s, 9H).

Intermediate XVII

2'-Cyano-5-(methoxycarbonyl)-1,1'-biphenyl-3-carboxylic acid

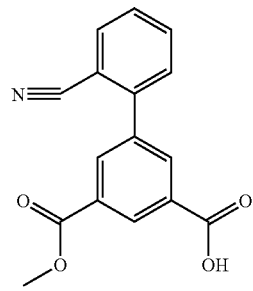

Step A: Arylation

To a solution of dimethyl 5-iodoisophthalate (13 g, 40.6 mmol) in 100 mL THF was added 2-cyanophenyl zinc bromide (97.5 mL, 48.7 mmol, 0.5 M THF) and tetrakis(triphenylphosphine) palladium (214 mg, 0.2 mmol) and the reaction mixture was stirred at rt for 2 h. The precipitated solid was filtered, the filtrate was diluted with MeOH to provide after filtration a second crop of dimethyl 5-(2-cyanophenyl) isophthalate: $^1$H NMR (400 MHz, CDCl$_3$) δ 8.78 (s, 1H), 8.42 (s, 2H), 7.81 (d, J=7.7 Hz, 1H), 7.70 (d, J=7.5 Hz, 1H), 7.57-7.50 (m, 2H), 3.98 (s, 6H). LCMS [(M)+H]$^+$=296

Step B: Ester Hydrolysis

To a solution of dimethyl 5-(2-cyanophenyl)isophthalate (4.5 g, 15.23 mmole) in THF/MeOH (500 mL of 5:1 THF/MeOH) was added a solution of sodium hydroxide (3.05 mL of 5 N NaOH, 15.25 mmole) and the reaction allowed to stir overnight at ambient temperature. The reaction was then concentrated at reduced pressure to one quarter volume and poured into water (1 L) and saturated sodium bicarbonate (250 mL) The mixture was extracted once with ethyl acetate (200 mL) and then acidified with aqueous HCl to pH 2. The mixture was extracted with ethyl acetate (2×300 mL) and the combined organics were washed with brine (50 mL), dried over anhydrous sodium sulfate, filtered and concentrated at reduced pressure to give an off white solid which was then swished with ethyl ether and filtered to give the title compound: $^1$H NMR (400 MHz, d$_6$-DMSO) δ 13.55 (br s, 1H), 8.60-8.55 (m, 1H), 8.38-8.31 (m, 2H), 8.02 (d, J=8.3 Hz, 1H), 7.85 (td, J=8.3 Hz, 1.5 Hz, 1H), 7.75 (d, J=8.3 Hz, 1H), 7.66 (td, J=8.3 Hz, 1.5 Hz, 1H), 3.93 (s, 3H).

Intermediate XVIII 5-(5-{(1R)-1-[(tert-butoxycarbonyl)amino]-1-methyl-2-phenylethyl}-1,3,4-oxadiazol-2-yl)-2'-cyanobiphenyl-3-carboxylic acid

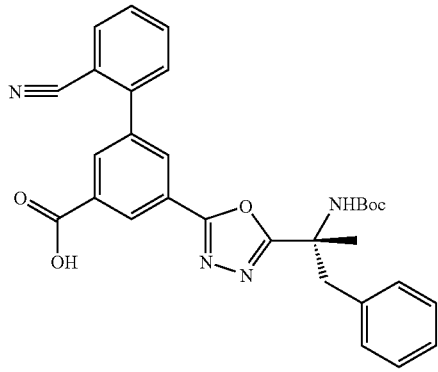

Step A: Coupling/Dehydration

To a stirring solution of 2'-cyano-5-(methoxycarbonyl)biphenyl-3-carboxylic acid (Intermediate XVII, 0.72 g, 2.56 mmol) and N-(tert-butoxycarbonyl)-α-methyl-D-phenylalanine hydrazide (Intermediate II) (0.75, 2.56 mmol) in DMF (10 mL) was added BOP reagent (1.18 g, 2.68 mmol) and diisopropyl ethyl amine (1.32 mL, 7.67 mmol). The reaction was allowed to proceed for 1 h, and then poured into water (200 mL). The aqueous was extracted with EtOAc (3×100 mL). The combined organics were washed with brine, dried over Na$_2$SO$_4$, filtered and concentrated to obtain the crude bis amide which was used without further purification as an off-white foam. The material thus obtained was dissolved in dichlorethane (10 mL) and was treated with methoxycarbonyl aminosulfamoyl triethylammonium hydroxide inner salt (Burgess reagent, 1.25 g, 5.0 mmole) the resulting solution was then heated in a microwave reactor for 5 min at 120° C. After cooling the product was purified directly by flash chromatography on silica gel eluting with 25% to 75% Ethyl acetate/hexane to give 780 mg of the product. $^1$H NMR (400 MHz, CDCL$_3$) δ 8.71 (br s, 1H), 8.4 (m, 2H), 7.84 (d, J=7.5 Hz, 1H), 7.72 (t, J=7.5 Hz, 1H), 7.61-7.52 (m, 2H), 7.32-7.24 (m, 3H), 7.10-7.04 (2H, m), 5.10 (br s, 1H), 4.0 (s, 3H), 3.60 (d, J=13 Hz, 1H), 3.47 (d, J=13 Hz, 1H), 1.75 (s, 3H), 1.42 (s, 9H). LCMS [(M)+H]$^+$=539.

Step B: Ester Hydrolysis

To a stirring solution of methyl 5-(5-{(1R)-1-[(tert-butoxycarbonyl)amino]-1-methyl-2-phenylethyl}-1,3,4-oxadiazol-2-yl)-2'-cyanobiphenyl-3-carboxylate from Step A (780 mg, 1.45 mmole) in methanol (20 mL) at rt was added 0.43 mL of 5 N NaOH aq. The reaction was allowed to stir at rt overnight. The solution was poured into water (100 mL) and acidified by adding 1N HCl (10 mL). The resulting mixture was extracted with ethyl acetate (2×100 mL). The combined organics were washed with brine (50 mL), dried over anhydrous sodium sulfate, filtered and concentrated at reduced pressure to give 5-(5-{1-[(tert-butoxycarbonyl)amino]-1-methyl-2-phenylethyl}-1,3,4-oxadiazol-2-yl)-2'-cyanobiphenyl-3-carboxylic acid (Intermediate XVII). $^1$H NMR (400 MHz, CDCl$_3$) δ 8.77 (br s, 1H), 8.47 (m, 2H), 7.84 (d, J=7.7 Hz, 1H), 7.72 (t, J=7.7 Hz, 1H), 7.65-7.55 (m, 2H), 7.33-7.25 (m, 3H), 7.13-7.05 (2H, m) 5.25 (br s, 1H), 3.61 (d, J=13.5 Hz, 1H), 3.46 (d, J=13.5 Hz, 1H), 1.76 (s, 3H), 1.42 (s, 9H). LCMS [(M)+H]$^+$=525

Intermediate XIX

5-[5-((1R)-1-amino-1-methyl-2-phenylethyl)-1,3,4-oxadiazol-2-yl]-2'-cyanobiphenyl-3-carboxylic acid

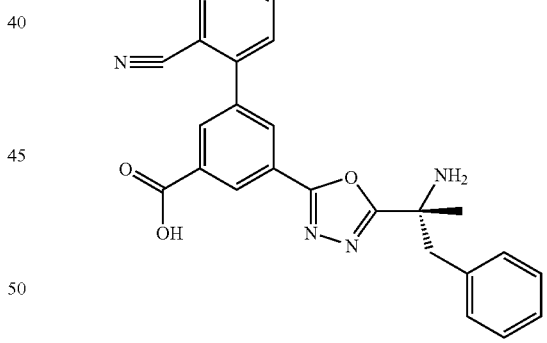

To a solution of 5-(5-{(1R)-1-[(tert-butoxycarbonyl)amino]-1-methyl-2-phenylethyl}-1,3,4-oxadiazol-2-yl)-2'-cyanobiphenyl-3-carboxylic acid (Intermediate XVIII, 500 mg. 0.95 mmol) in dioxane (5 mL) at rt was added a solution of HCl in dioxane (7 mL of 4N HCl in dioxane, 28 mmol) and the solution allowed to stand for 1 hour at rt. The solvent was then evaporated at reduced pressure to give 5-[5-(1-amino-1-methyl-2-phenylethyl)-1,3,4-oxadiazol-2-yl]-2'-cyanobiphenyl-3-carboxylic acid (Intermediate XIX) as the derived hydrochloride salt. $^1$H NMR (400 MHz, CD$_3$OD) δ 8.71 (t, J=1.5 Hz, 1H), 8.45-8.42 (m, 2H), 7.94 (dd, J=7.8, 1 Hz, 1H), 7.85 (dt, J=7.8, 1Hz, 1H), 7.72 (d, J=7.6 Hz, 1H), 7.66 (dt, J=7.6, 1.1 Hz), 7.34-7.28 (m, 3H), 7.15-7.09 (m, 2H), 3.47 (s, 2H), 1.90 (s, 3H). LCMS [(M)+H]$^+$=425.

Intermediate XX (1R)-2-(1-methylbut-2-yn-1-yl)amine hydrochloride

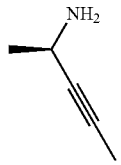

Step A: Ellman Sulfinyl Imine Formation

To a solution of acetaldehyde (2.8 g, 64.36 mmol) and (S)-2-Methyl-2-propane sulfinamide (3.9 g, 32.18 mmol) in methylene chloride (20 mL) at rt was added powdered anhydrous magnesium sulfate (19 g, 160 mmol). The resultant slurry was stirred overnight at ambient temperature. The reaction was diluted with methylene chloride (200 mL) and filtered and the solids washed with another 100 mL portion of methylene chloride. The filtrate was concentrated at reduced pressure to give the product as an oil. $^1$H NMR (400 MHz, CDCl$_3$) δ 8.08 (q, J=5.1 Hz, 1H), 2.24 (d, J=5.1 Hz, 3H), 1.19 (s, 9H). LCMS [(M)+H]$^+$=150.

Step B: Grignard Addition

To a solution of the product of Step A above (400 mg, 2.72 mmol) in methylene chloride at 0° C. was added a solution of 1-propynyl magnesium bromide (6 mL of 0.5 N in THF) The reaction was warmed to rt and poured into water (100 mL) and extracted with ethyl acetate (2×100 mL). The combined organics were washed with brine (50 mL), dried over anhydrous sodium sulfate, filtered and concentrated at reduced pressure. The residue was chromatographed on silica gel eluting with a gradient of 50% to 75% Ethyl acetate/hexanes to give the product as a gummy solid. $^1$H NMR (400 MHz, CDCl$_3$) δ 4.13 (m, 1H), 3.33 (m, 1H), 1.82 (s, 3H), 1.40 (d, J=6.7 Hz, 3H), 1.21, (s, 9H). LCMS [(M)+H]$^+$=188.

Step C: Chiral Auxiliary Removal

To a solution of (310 mg. 1.65 mmol) in methanol (5 mL) at rt was added a solution of HCl in dioxane (8 mL of 4N HCl in dioxane, 32 mmol) and the solution allowed to stand for 1 h at rt. The solvent was then evaporated at reduced pressure to give -(1-methylbut-2-yn-1-yl)amine hydrochloride as its derived hydrochloride salt. $^1$H NMR (400 MHz, CD$_3$OD) δ 4.15-4.17 (m, 1H), 1.86 (d, J=2.3 Hz, 3H), 1.49, (d, J=6.8 Hz, 3H). LCMS [(M)+H]$^+$=84.

Intermediate XXI 3-amino-N-[(1R)-1-(4-fluorophenyl)ethyl]-5-[propyl (methylsulfonyl)amino]benzamide

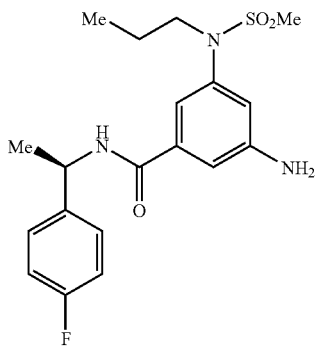

This compound was synthesized analogously to Intermediate IX, with the only difference being the substitution of propyl iodide for methyl iodide in Step C.

Intermediate XXII 3-(4-acetyl-1H-1,2,3-triazol-1-yl)-N-[(1R)-1-(4-fluorophenyl)ethyl]-5-[(methylsulfonyl)(propyl)amino]benzamide

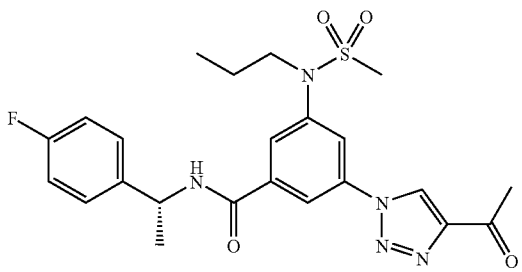

Step A: Aryl Azide Formation

To a solution of 0.2 g (0.5 mmol) 3-amino-N-[(1R)-1-(4-fluorophenyl)ethyl]-5-[(methylsulfonyl)(propyl)amino]benzamide (Intermediate XXI) in 4 mL acetic acid was added 1 mL water followed by 0.038 g (0.55 mmol) sodium nitrite. After 2 minutes 0.035 g (0.055 mmol) sodium azide was added resulting in gas evolution. The reaction mixture was stirred for 30 minutes then diluted with 75 mL EtOAc, washed with 50 mL water, 50 mL 4M NaOH, 50 mL brine, dried over MgSO$_4$, filtered, and concentrated. Purification by automated flash chromatography (40 g silica gel cartridge, 20-100% EtOAc/hexanes over 20 min) afforded 3-azido-N-[(1R)-1-(4-fluorophenyl)ethyl]-5-[(methylsulfonyl)(propyl)amino]benzamide. $^1$H NMR (CDCl$_3$, 400 MHz) δ 7.45 (br t, J=1.47 Hz, 1H), 7.36 (m, 3H), 7.11 (t, J=2.01 Hz, 1H), 7.06 (m, 2H), 6.31 (br d, J=7.32 Hz, 1H), 5.28 (quint, J=7.14 Hz, 1H), 3.64 (t, J=7.15 Hz, 2H), 2.89 (s, 3H), 1.61 (d, J=6.96 Hz, 3H), 1.5 (m, 2H), 0.91 (t, J=7.33 Hz, 3H). LCMS [M+H]$^+$=420.1

Step B: Cycloaddition

To a solution of 0.15 g (0.36 mmol) 3-azido-N-[(1R)-1-(4-fluorophenyl)ethyl]-5-[(methylsulfonyl)(propyl)amino]benzamide in 2 mL t-BuOH was added 1 mL water and 0.004 g (0.018 mmol) copper(II) sulfate hydrate and 0.007 g (0.036 mmol) sodium ascorbate. The heterogeneous reaction mixture was stirred at rt for 24 h, then diluted w. 75 mL EtOAc, washed with 50 mL water, 50 mL brine, dried over MgSO$_4$, filtered, and concentrated. Purification by automated flash chromatography (40 g silica gel cartridge 20-100% EtAOc/hex over 15 min) afforded 0.18 g (100%) 3-(4-acetyl-1H-1,2,3-triazol-1-yl)-N-[(1R)-1-(4-fluorophenyl)ethyl]-5-[(methylsulfonyl) (propyl)amino]benzamide as a foam. $^1$H NMR (CDCl$_3$, 400 MHz) δ 8.57 (s, 1H), 8.11 (br t, J=1.83 Hz, 1H), 7.93 (t, J=2.02 Hz, 1H), 7.89 (br t, J=1.64 Hz, 1H), 7.38 (m, 2H) 7.06 (m, 2H), 6.52 (br d, J=7.50 Hz, 1H), 5.32 (quint, J=7.15 Hz, 1H), 3.74 (t, J=7.14 Hz, 2H), 2.93 (s, 3H), 2.76 (s, 3H), 1.64 (d, J=6.96 Hz, 3H), 1.54 (m, 2H), 0.93 (t, J=7.32 Hz, 3H). LCMS [M+H]$^+$=488.1

Intermediate XXIII tert-butyl[1-(5-{3-{[methoxy(methyl)amino]carbonyl}-5-[methyl (methylsulfonyl)amino]phenyl}-1,3,4-oxadiazol-2-yl)-1-(1R)-methyl-2-phenylethyl]carbamate

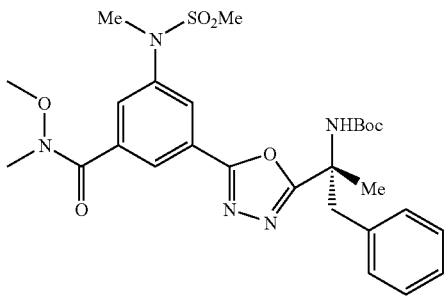

To a slurry of 3-(5-{1-[(tert-butoxycarbonyl)amino]-1-methyl-2-phenylethyl}-1,3,4-oxadiazol-2-yl)-5-[methyl (methylsulfonyl)amino]benzoic acid (Intermediate VI) (0.303 g, 0.571 mmol) and Weinreb amine hydrochloride (0.111 g, 1.142 mmol) in 6 mL CHCl$_3$ was added diisopropylethylamine (0.150 mL, 0.857 mmol), followed by EDC (0.154 g, 0.857 mmol) and HOAt (0.035 g, 0.228 mmol) After 7 days at rt, the reaction was quenched by the addition of brine. The layers were separated, the aqueous washed with CH2Cl2 (2×), the combined organics were washed with brine, dried over Na2SO4, filtered and concentrated. Purification with normal phase chromatography (40->100% EA/hex) afforded tert-butyl[1-(5-{3-{[methoxy(methyl)amino]carbonyl}-5-[methyl(methylsulfonyl)amino]phenyl}-1,3,4-oxadiazol-2-yl)-1-methyl-2-phenylethyl]carbamate as a white foam. $^1$H NMR (CDCl$_3$, 400 MHz) 8.21 (app t, J=1.5 Hz, 1H), 8.11 (app t, J=2.0 Hz, 1H), 7.90 (app t, J=1.5 Hz, 1H), 7.30-7.22 (m, 3H), 7.06-7.04 (m, 2H), 5.04 (br s, 1H), 3.60 (s, 3H), 3.42 (s, 3H), 3.39 (s, 3H), 2.90 (s, 3H), 1.69 (s, 3H), 1.41 (s, 9H). LCMS [M+H]$^+$=574.

Intermediate XXV ethyl-3-[(Z)-2-(2-methylcyclopropyl)vinyl]-5-[(methylsulfonyl) (propyl)amino]benzenecarboximidoate

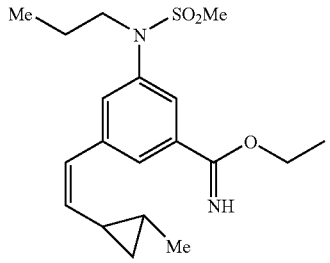

Step A: Carboxamide Formation

To a solution of Intermediate XV (0.069 g, 0.204 mmol) in 1.2 mL CH$_2$Cl$_2$ was added EDC (0.059 g, 0.307 mmol), followed by HOAt (0.022 g, 0.164 mmol). After 30 min at rt, 1 mL DMF was added, the reaction was cooled to −10° C., and gaseous ammonia was bubbled through the reaction for 30 min. The reaction was quenched by the addition of satd. aqueous NaHCO$_3$ and diluted with EtOAc. The layers were separated, and the aqueous layer washed with fresh EtOAc (2×). The combined organics were washed with aqueous 3M LiCl and brine, dried over Na$_2$SO$_4$, filtered and concentrated. The residue was purified by normal phase chromatography (40->100% EtOAc/hex) to afford the desired carboxamide as a viscous oil. $^1$H NMR (CDCl$_3$) δ 7.99 (s, 1H), 7.72 (s, 1H), 7.65 (s, 1H), 7.62 (s, 2H), 6.27 (d, J=11.3 Hz, 1H), 5.19 (dd, J=11.4, 10.1 Hz, 1H), 3.66-3.61 (m, 2H), 2.94 (s, 3H), 1.53-1.45 (m, 2H), 1.10 (d, J=6.0 Hz, 3H), 0.93-0.86 (m, 5H), 0.69-0.64 (m, 2H), LCMS [(M+CH$_3$CN)+H]$^+$=378.

Step B: Imidate Formation

To a solution of carboxamide from Step A (0.067 g, 0.199 mmol) in 1.8 mL CH$_2$Cl$_2$ was added triethyloxonium hexafluorophosphate (0.069 g, 0.279 mmol). After 15 h, a further aliquot of triethyloxonium hexafluorophosphate (0.035 g, 0.140 mmol) was added, and after 4 h, the reaction was quenched by adding satd. NaHCO3 and diluted with EtOAc and H2O. The layers were separated, and the aqueous layer washed with fresh EtOAc (2×). The combined organics were washed with aqueous 3M LiCl and brine, dried over Na$_2$SO$_4$, filtered and concentrated. This residue was used without further purification. LC/MS [M+H]$^+$=365.

Intermediate XXVI rac-N-(tert-butoxycarbonyl)-benzylprolinehydrazide

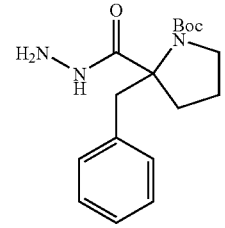

Step A: Coupling

To a soln of rac-N-Boc-benzyl proline (0.170 g, 0.557 mmol) and Cbz-hydrazine (0.185 g, 1.113 mmol) in 3 mL CH$_2$Cl$_2$ was added Hunig's base (0.29 mL, 1.67 mmol) and BOP-reagent 0.369 g, 0.835 mmol). After 2.5 h, the reaction was poured onto a silica gel column and purified using normal phase chromatography (30->90% EtOAc/hexanes). $^1$H NMR (CDCl$_3$) was a mixture of amide rotamers. LCMS (M+H)$^+$=454.

Step B: Deprotection

To a slurry of adduct from Step A (0.208 g, 0.459 mmol) in 8 mL EtOAc was added 10% Pd/C (0.049 g, 0.046 mmol). The vessel was evacuated and opened to H2 (3×), and the reaction was allowed to proceed under an atmosphere of H$_2$ for 5 h. The flask was evacuated and opened to Ar (3×), and the reaction was filtered through a pad of celite, rinsing with fresh EtOAc. The organics were concentrated to yield N-(tert-butoxycarbonyl)-benzylprolinehydrazide as a white wax. $^1$H NMR (d$_4$-MeOD) δ 7.29-7.21 (m, 3H), 7.15-7.13 (m, 2H), 3.68 (d, J=13.6 Hz, 1H), 3.54 (d, J=13.6 Hz, 1H), 3.43 (m, 1H), 2.72 (m, 1H), 2.21-1.99 (m, 2H), 1.09 (m, 1H), 0.90 (m, 1H). LCMS [(M-Boc)+H]$^+$=220.

Intermediate XXVII

3-bromo-5-nitrobenzoic acid methyl ester

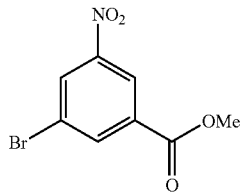

To a solution of 3-bromo-5-nitrobenzoic acid (1.26 g, 5.12 mmol) in 20 mL MeOH was added thionyl chloride (0.410 mL, 5.63 mmol) dropwise via syringe. The reaction was heated to reflux for 15 h, cooled to rt and concentrated to afford a white solid. $^1$H NMR (CDCl$_3$) δ 8.77 (m, 1H), 8.53 (m, 1H), 8.47 (m, 1H), 3.98 (s, 3H).

Intermediate XXVIII

3-bromo-5-[methyl(methylsulfonyl)amino]benzoic acid

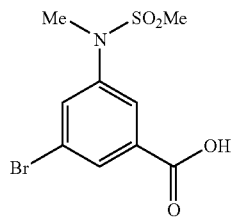

Prepared from Intermediate XXVII following Steps B, C, D and I in the synthesis of Intermediate XIV. This compound does not ionize by LCMS. $^1$H NMR (d$_4$-MeOH) δ 8.04 (m, 1H), 8.00 (m, 1H), 7.84 (m, 1H), 3.32 (s, 3H), 2.91 (s, 3H).

Intermediate XXIX tert-butyl[1-(5-{3-bromo-5-[methyl(methylsulfonyl)amino]phenyl}-1,3,4-oxadiazol-2-yl)-(1R)-1-methyl-2-phenylethyl]carbamate

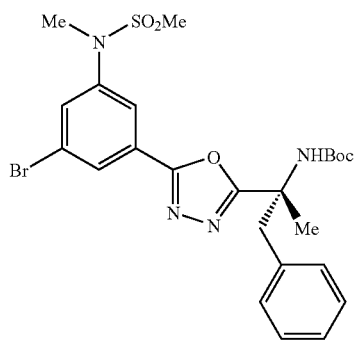

Prepared from Intermediate II and Intermediate XXVIII as using a procedure as described for the synthesis of Intermediate VI. LCMS [M+H]$^+$=566.

Intermediate XXX

Methyl-3-(hydrazinocarbonyl)-5-[methyl(methylsulfonyl)amino]benzoate

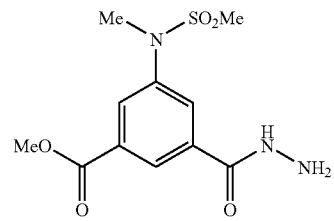

Step A: Coupling

To a solution of Intermediate III (0.520 g, 1.810 mmol) and Boc-hydrazine (0.359 g, 2.715 mmol) in 8 mL CH$_2$Cl$_2$ was added Hunig's base (0.950 mL, 5.43 mmol) and BOP-reagent (0.881 g, 1.991 mmol). After 30 min, the reaction was poured onto a silica gel column and purified by normal phase chromatography (5->75% EtOAc/hexanes) to afford the desired product as a white foam. $^1$H NMR (d$_4$-MeOH) δ 8.40 (s, 1H), 8.22 (s, 1H), 8.11 (s, 1H), 3.93 (s, 3H), 3.37 (s, 3H), 2.93 (s, 3H), 1.49 (s, 9H); LCMS [(M-Boc)+H]$^+$=302.

Step B: Boc Deprotection

Gaseous HCl was bubbled through a solution of product from Step A in 20 mL CH$_2$Cl$_2$ at 0° C. for 5 min. The reaction was warmed to rt for 20 min, then concentrated to afford Methyl-3-(hydrazinocarbonyl)-5-[methyl(methylsulfonyl)amino]benzoate as a white solid. $^1$H NMR (d$_4$-MeOH) δ 8.42 (m, 1H), 8.29 (m, 1H), 8.17 (m, 1H), 3.95 (s, 3H), 3.38 (s, 3H), 2.95 (s, 3H); LCMS [M+H]$^+$=302.

Intermediate XXXI

3-bromo-5-(methoxycarbonyl)benzoic acid

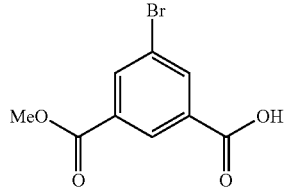

Prepared from dimethyl 5-bromoisopthalate using a procedure similar to that described in Step C for the preparation of Intermediate III.

Intermediate XXXII 3-bromo-5-(5-{(1R)-1-[(tert-butoxycarbonyl)amino]-1-methyl-2-phenylethyl}-1,3,4-oxadiazol-2-yl)benzoic acid

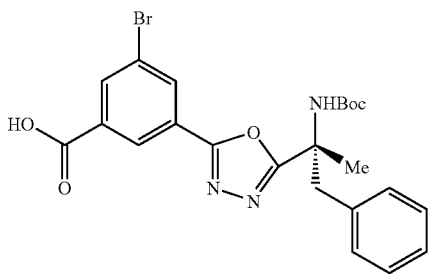

Prepared from Intermediate II and Intermediate XXXI following a sequence similar to that used for the preparation of Intermediate VI.

Intermediate XXXIII

3-[5-((1R)-1-amino-1-methyl-2-phenylethyl)-1,3,4-oxadiazol-2-yl]-5-(1,3-oxazol-2-yl)benzoic acid

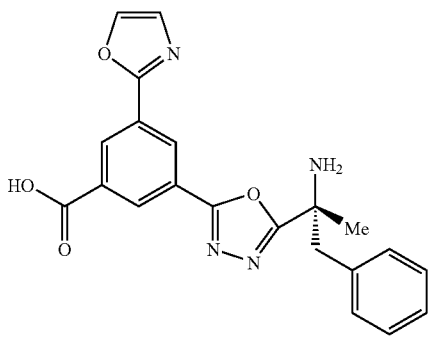

Step A: Cross-Coupling

To a solution of oxazole (0.080 g, 1.158 mmol) in 4 mL degassed THF at −78° C. was added 2.5M n-BuLi in hexanes (0.460 mL, 1.158 mmol). The rxn was allowed to proceed at −78° C. for 30 min, then 0.50M ZnCl$_2$ in THF (degassed prior to addition) was added via syringe. The bath was removed, and 8.1 mL of this solution was added to Intermediate XXXII (0.100 g, 0.199 mmol) and Pd(Ph$_3$P)$_4$. This solution was microwaved at 85° C. for 45 min, then the reaction was quenched by the addition of water and diluted with EtOAc. The pH of the aqueous layer was adjusted to ~3 by the addition of 0.5M KHSO$_4$, and the layers were separated. The aqueous washed with EtOAc (3×), the combined organics were dried over Na$_2$SO$_4$, filtered and concentrated. Purification by normal phase chromatography (0-15% MeOH/CH$_2$Cl$_2$) afforded the desired product as a yellow foam. $^1$H NMR (d$_4$-MeOH) δ 8.99 (s, 1H), 8.88 (s, 1H), 8.80 (s, 1H), 7.80 (s, 1H), 7.33-7.25 (m, 5H), 7.07 (s, 1H), 3.60 (d, J=12.8 Hz, 1H), 3.44 (d, J=12.8 Hz, 1H), 1.73 (s, 3H), 1.40 (s, 9H); LCMS [M+H]$^+$=491.

Step B: Deprotection

To a solution of product from Step A (0.098 g, 0.199 mmol) in 3 mL EtOAc was added 3 mL EtOAc saturated with HCl at 0° C. The reaction was allowed to proceed at rt for 1.5 h, then concentrated to afford 3-[5-(1-amino-1-methyl-2-phenylethyl)-1,3,4-oxadiazol-2-yl]-5-(1,3-oxazol-2-yl)benzoic acid as a yellow foam. This material was used without further purification. LCMS [M+H]$^+$=391.

Intermediate XXXIV tert-butyl[1-(5-{3-bromo-5-[(dipropylamino)carbonyl]phenyl}-1,3,4-oxadiazol-2-yl)-(1R)-1-methyl-2-phenylethyl]carbamate

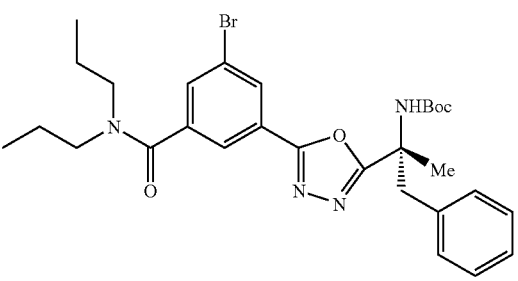

To a solution of Intermediate XXXII (0.300 g, 0.597 mmol) and dipropylamine (0.060 g, 0.597 mmol) in 10 mL of DMF was added EDC (0.137 g, 0.717 mmol) and HOAt (0.089 g, 0.657 mmol). The reaction was stirred at rt for 50 h, then diluted with EtOAc. The organic layer washed with H$_2$O, 10% KHSO$_4$, sat. NaHCO$_3$ and 3M LiCl, dried over Na$_2$SO$_4$, filtered and concentrated. The residue was purified by normal phase chromatography (5->35% EtOAc/hexanes) to obtain the desired bromide as a white solid. $^1$H NMR (CDCl$_3$) δ 8.17 (t, J=1.6 Hz, 1H), 7.94 (m, 1H), 7.65 (m, 1H), 7.30-7.26 (m, 3H), 7.06-7.04 (m, 2H), 3.58-3.40 (m, 4H), 3.20-3.16 (m, 2H), 1.72 (s, 5H), 1.56 (s, 2H), 1.42 (s, 9H), 1.02-0.98 (m, 3H), 0.81-0.77 (m, 3H). LCMS [M+H]$^+$=586 and 588.

Intermediate XXXV

3-[5-((1R)-1-amino-1-methyl-2-phenylethyl)-1,3,4-oxadiazol-2-yl]-5-bromo-N—[(R)-1-(4-fluorophenyl)ethyl]benzamide

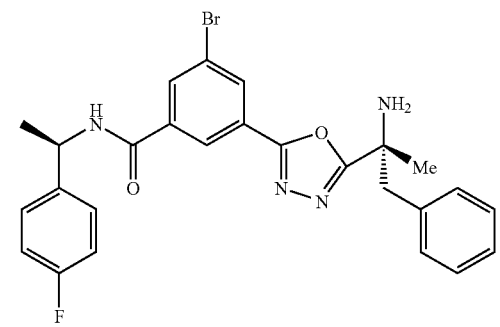

Prepared following a procedure as described for the synthesis of Intermediate XXXIV.

Intermediate XXXVI

[3-(methoxycarbonyl)-2-furyl]boronic acid

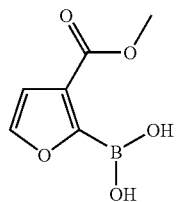

Methyl 2-bromofuran-3-carboxylate was synthesized from 3-furoic acid as described in the literature (Johansson, G.; etc. *J. Med. Chem.* 1997, 40, 3804-3819).

To the methyl 2-bromofuran-3-carboxylate in toluene (0.8 mL) and THF (0.2 mL) was added triisopropyl borate (0.183 g, 0.976 mmol). The mixture was cooled to −78° C. n-butyllithium (2.5M in hexane, 0.39 mL, 0.976 mmol) was added dropwise, and the mixture was stirred for an additional 0.5 h. The reaction mixture was then allowed to warm to −20° C. before a 2N HCl solution (0.5 mL) was added. When the mixture reached rt, it was diluted with EtOAc and the organic layers were concentrated. The residue was titrated with cold hexane and concentrated to give boronic acid as brown solid. This was used without further purification. LCMS [M+H]$^+$=171.

Intermediate XXXVII tert-butyl[1-(5-{3-(bromomethyl)-5-[methyl(methylsulfonyl)amino]phenyl}-1,3,4-oxadiazol-2-yl)-(1R)-1-methyl-2-phenylethyl]carbamate

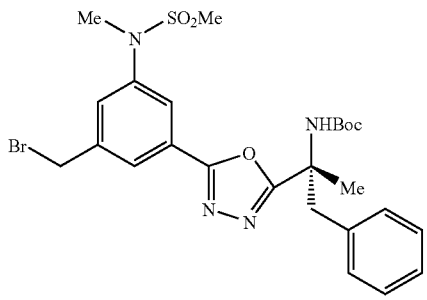

To a solution of Intermediate VI (0.120 g, 0.226 mmol) in 2 mL anhydrous THF at 0° C. under argon was added 1.0M BH3-THF in THF (2.26 mL, 2.262 mmol). It was allowed to warm to rt. After 16 hr at rt, the reaction was cooled back down to 0° C. and quenched with MeOH. It was concentrated to half its original volume and was diluted with EtOAc and H$_2$O. The layers were separated, and the aqueous layer was extracted with EtOAc (2×). The combined organics were washed with sat'd NaHCO$_3$ and brine, dried over Na$_2$SO$_4$, filtered, and concentrated to afford the desired alcohol as a white foam which was taken up in 2 mL anhydrous CH$_2$Cl$_2$ under argon with CBr$_4$ (0.136 g, 0.411 mmol). To the resulting solution was added Ph$_3$P (0.099 g, 0.380 mmol) portionwise. After 12 hr, the reaction was concentrated under reduced pressure and purified using normal phase chromatography (10->65% EtOAc/hexanes) to afford tert-butyl[1-(5-{3-(bromomethyl)-5-[methyl(methylsulfonyl)amino]phenyl}-1,3,4-oxadiazol-2-yl)-1-methyl-2-phenylethyl]carbamate as a white solid. $^1$H NMR (CDCl$_3$, 400 MHz) δ: 7.94 (s, 1H), 7.92 (s, 1H), 7.64 (s, 1H), 7.32-7.27 (m, 3H), 7.10-7.05 (m, 2H), 5.14-4.98 (br s, 1H), 4.52 (s, 2H), 3.57 (A of AB, d, J=13.6 Hz, 1H), 3.46-3.38 (m, 1H), 3.40 (s, 3H), 2.91 (s, 3H), 1.73 (s, 3H), 1.43 (s, 9H). LCMS [M+H]$^+$=579.

Intermediate XXXVIII

Tert-butyl (2R)-2-(2,2-dirobovinyl)pyrrolidine-1-carboxylate

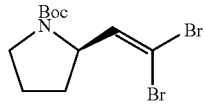

To a stirred solution of triphenylphosphine (31.7 g, 120.8 mmol) and carbon tetrabromide (20.0 g, 60.3 mmol) in methylene chloride (450 mL) at 0° C. was added dropwise a solution of N-(tert-Butoxycarbonyl)-D-prolinal (6.0 g, 30.1 mmol) in methylene chloride (50 mL). Upon complete addition of the aldehyde, the cooling bath was removed and mixing continued for an additional 30 minutes at ambient temperature. The mixture was poured into saturated sodium bicarbonate solution (600 mL) and the organic layer was extracted, dried over sodium sulfate anhydrous, concentrated in vacuo and purified on a silica gel column using a 100% to 99:1 gradient of methylene chloride to methanol as mobile phase to yield pure tert-butyl 2-(2,2-dibromovinyl)pyrrolidine-1-carboxylate. LC-MS m/z (minus t-butyl+1)=300. $^1$H NMR (CDCl$_3$, 400 Mhz) 6.37 ppm (s, 1H), 4.36 (s, 1H), 3.5-3.4 (m, 2H), 2.2-2.1 (m, 1H), 1.88-1.82 (m, 2H), 1.77-1.71 (m, 1H), 1.56 (s, 1H), 1.47 (s, 9H).

Intermediate XXXIX

Tert-butyl (2R)-2-ethynylpyrrolidine-1-carboxylate

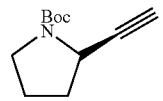

Tert-butyl (2R)-2-(2,2-dibromovinyl)pyrrolidine-1-carboxylate (Intermediate XXXVIII, 8.1 g, 22.8 mmol) was dissolved in dry THF (200 mL) and cooled to −78° C. Then added sec-butyllithium 1.4M in cyclohexane (32.6 mL, 45.6 mmol) over 30 minutes and continued mixing an additional 30 minutes before quenching with 20% ammonium chloride solution (200 mL). The mixture was warmed to rt and diluted with ethyl ether (200 mL). The organic phase was separated, washed with brine, dried in vacuo and purified on a silica gel column using a 100% to 99:1 gradient of methylene chloride to methanol as mobile phase to yield pure tert-buty (2R)-2-ethynylpyrrolidine-1-carboxylate. LC-MS m/z (minus t-butyl+1)=220. ¹H NMR (CD₃OD, 400 Mhz) 4.44 ppm (s, 1H), 3.44-3.37 (m, 1H), 3.34-3.25 (m, 1H), 2.61 (s, 1H), 2.08-1.85 (m, 4H), 1.47 (s, 9H).

Intermediates XXXVIII and XXXIX can be referenced in Eugene J. Trybulski, Richard H. Kramss, Richard M. Mangano, and Andrew Rusinko, III. Chemical and Biochemical Studies of 2-Propynylpyrrolidine Derivatives. Restricted-Rotation Analogues of N-Methyl-N-(1-methyl-4-pyrrolidino-2-butynyl)acetamide (BM-5). *J. Med. Chem.* 1990, 33, 3190-3198.

Intermediate XL (2R)-2-prop-1-ynylpyrrolidine

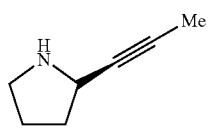

Step A: Alkylation

Tert-butyl-(2R)-2-ethynylpyrrolidine-1-carboxylate (0.71 g, 3.6 mmol) was dissolved in THF (3 mL) and cooled to –78° C. Then added 1.6M butyl lithium in hexane (2.7 mL, 4.3 mmol) and continued stirring for 20 minutes before adding iodomethane (0.27 mL, 4.3 mmol) and allowing the mixture to return to ambient temperature overnight. Upon completion (TLC using 3:1 Ethyl acetate to hexane with ninhydrin), the mixture was quenched with water, extracted with ethyl acetate, dried over sodium sulfate, filtered and concentrated in vacuo to yield tert-butyl (2R)-2-ethynylpyrrolidine-1-carboxylate. LC-MS m/z (minus t-butyl+1)=154. ¹H NMR (CD₃OD, 400 Mhz) 4.39 ppm (s, 1H), 3.40-3.36 (m, 1H), 3.31-3.23 (m, 1H), 2.04-2.01 (m, 2H), 1.92-1.84 (m, 2H), 1.78 (s, 3H), 1.46 (s, 9H).

Step B: Deprotection

Anhydrous HCl was bubbled into a stirred solution of tert-butyl (2R)-2-ethynylpyrrolidine-1-carboxylate (0.71 g, 3.4 mmol) in ethyl acetate (15 mL) at 0° C. and allowed to mix for 45 min. Upon completion of the reaction as visualized by TLC (99:1 CH₂Cl₂ to MeOH), the solution was dried in vacuo to yield 2-prop-1-ynylpyrrolidinium chloride. LC-MS m/z=111. ¹H NMR (CD3OD, 400 Mhz) 4.33-4.31 ppm (m, 1H), 3.42-3.24 (m, 2H), 2.36-1.99 (m, 4H), 1.88 (s, 3H).

Intermediate XLI (2R)-2-vinylpyrrolidine

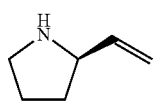

Tert-butyl (2R)-2-vinylpyrrolidine-1-carboxylate was formed as a by-product from the reaction of Intermediate 2. (HPLC RT=2.8 min.) HRMS (ES/FTMS) C₁₁H₁₉NO₂ calcd. 198.1489 (M+1), found: 198.1493. ¹H NMR (CD₃OD, 400 Mhz) 5.80-5.72 ppm (m, 1H), 5.04 (d, 2H), 4.27 (s, 1H), 3.41-3.3 (m, 2H), 2.08-1.81 (m, 4H), 1.45 (s, 9H). (2R)-2-vinylpyrrolidinium chloride was synthesized from tert-butyl (2R)-2-vinylpyrrolidine-1-carboxylate in the same way as Intermediate XL, step B.

Intermediate XLII (2S)-2-ethylpyrrolidine

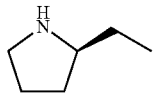

Step A: Hydrogenation

Tert-butyl-(2R)-2-vinylpyrrolidine-1-carboxylate (0.21 g, 1.07 mmol) was dissolved in methanol (10 mL) with palladium on carbon, 10% catalyst (0.046 g, 20% by wt.) and subjected to a hydrogen atmosphere via balloon. The reaction was run overnight and filtered through Celite and concentrated in vacuo to yield tert-butyl (2S)-2-ethylpyrrolidine-1-carboxylate (0.18 g, HPLC RT=3.00 min.). LC-MS m/z (minus t-butyl+CH₃CN+1)=185. ¹H NMR (CD₃OD, 400 Mhz) 3.67-3.63 ppm (m, 1H), 3.36-3.30 (m, 2H), 1.92-1.71 (m, 4H), 1.45 (s, 9H), 1.43-1.29 (m, 2H), 0.90-0.85 (t, 3H).

Step B: Deprotection (2S)-2-ethylpyrrolidinium chloride was synthesized from tert-butyl(2S)2-ethylpyrrolidine-1-carboxylate in the same way as Intermediate XL, step B. ¹H NMR (CD₃OD, 400 Mhz) 3.45-3.39 ppm (m, 1H), 3.34-3.23 (m, 2H), 2.26-2.19 (m, 1H), 2.13-1.99 (m, 2H), 1.82-1.61 (m, 3H), 1.07-1.03 (t, 3H).

Intermediate XLIII (2R)-2-[(1Z)-prop-1-enyl]pyrrolidine

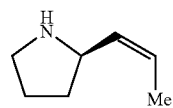

Step A: Wittig Reaction

To a solution of Boc-D-prolinal (0.5 g, 2.5 mmol) in tetrahydrofuran (10 mL) was added ethyltriphenylphosphonium bromide (3.7 g, 10.0 mmol) and cooled to –78° C. Then added dropwise lithium hexamethyldisilazide 1.0 M in THF (12 mL) and continued stirring from –78° C. to rt overnight. Upon completion as determined by TLC (99:1 methylene chloride to methanol with ninhydrin) the mixture was quenched with 20% ammonium chloride solution and extracted with ethyl acetate. The organic washed with brine, dried over sodium sulfate anhydrous and concentrated in vacuo very carefully as the product is volatile. Crude product was purified on silica gel using a 99:1 mixture of methylene chloride to methanol as mobile phase with ninhydrin to develop. Pure fractions were combined and dried to yield tert-butyl-(2R)-2-[(1Z)-prop-1-enyl]pyrrolidine-1-carboxylate. LC-MS m/z (minus t-butyl+1)=156. ¹H NMR (CD₃OD, 400 Mhz) 5.47-5.41 ppm (m, 1H), 5.34-5.28 (m, 1H), 4.58-4.53 (m, 1H), 3.42-3.34 (m, 3H), 2.14-2.06 (m, 1H), 1.96-1.77 (m, 2H), 1.70-1.58 (m, 3H), 1.42 (s, 9H).

Step B: Deprotection (2R)-2-[(1Z)-prop-1-enyl]pyrrolidinium chloride was synthesized from tert-butyl-(2R)-2-[(1Z)-prop-1-enyl]pyrrolidine-1-carboxylate in the same way as Intermediate XL, step B.

Intermediate XLIV 2-(ethylthio)-1,3-benzothiazole

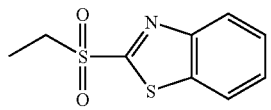

Step A: Mitsunobo Reaction

Ethyl alcohol (0.63 mL, 10.8 mmol), 2-benzothiazolethiol (2.0 g, 11.9 mmol) and triphenylphosphine (3.1 g, 11.9 mmol) were dissolved in tetrahydrofuran (50 mL) and cooled to 0° C. Then added diisopropylazadicarboxylate (2.3 mL, 11.9 mmol) and continued stirring for 1 hr. Upon completion, the reaction mixture was dried in vacuo, filtered through a plug of silica with 5% ethyl acetate in hexane and dried in vacuo again to yield 2-(ethylthio)-1,3-benzothiazole (2.2 g, HPLC RT=3.05 min.). LC-MS m/z=196.

Step B: Oxidation 2-(ethylthio)-1,3-benzothiazole (2.2 g, 11.2 mmol) was dissolved in methylene chloride and cooled to 0° C. Then added sodium bicarbonate (6.2 g, 73.9 mmol) and 3-chloroperoxybenzoic acid (10.2 g, 58.8 mmol) and continued stirring for 2 hr. The mixture was quenched with 1M sodium thiosulfate solution (20 mL), saturated sodium bicarbonate solution (20 mL) and diluted with ethyl ether and water. The organic layer washed with sodium thiosulfate solution, brine, dried over sodium sulfate anhydrous, filtered and concentrated in vacuo to yield 2-(ethyl sulfonyl)-1,3-benzothiazole (1.8 g, HPLC RT=2.30 min.). LC-MS m/z=228. $^1$H NMR (CD$_3$OD, 400 Mhz) 8.22-8.17 ppm (m, 2H), 7.72-7.63 (m, 2H), 3.63-3.57 (q, 2H), 1.39-1.35 (t, 3H).

Intermediate XLV (2R)-2-[(1E)-prop-1-enyl]pyrrolidine

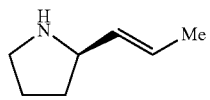

Step A: Modified Julia Olefination

To a stirring solution of Boc-D-Prolinal (0.53 g, 2.65 mmol) and 2-(ethyl sulfonyl)-1,3-benzothiazole (1.5 g, 6.62 mmol) in tetrahydrofuran (4 mL) at −78° C. was added 1M Lithium bis(trimethylsilyl)amide in THF (4 mL) and continued stirring for 30 min. Then the mixture was warmed to 0° C. and stirred for an additional 3 hr. Upon completion via LC-MS, the reaction mixture was quenched with 20% ammonium chloride solution and extracted with ethyl ether. The ether layer washed with brine, dried over sodium sulfate anhydrous, filtered and dried in vacuo to yield crude product which was further purified on an ISCO normal phase HPLC using a 100% to 75% gradient of hexane to ethyl acetate as mobile phase. Pure tert-butyl-(2R)-2-[(1E)-prop-1-enyl]pyrrolidine-1-carboxylate was isolated from the combined fractions (0.09 g). $^1$H NMR (CD$_3$OD, 400 Mhz) 5.51-5.44 ppm (m, 1H), 5.39-5.31 (m, 1H), 4.20-4.12 (m, 1H), 3.38-3.30 (m, 3H), 1.91-1.81 (m, 2H), 1.79-1.66 (m, 4H), 1.425 (s, 9H).

Step B: Deprotection (2R)-2-[(1E)-prop-1-enyl]pyrrolidinium chloride was synthesized from tert-butyl-(2R)-2-[(1E)-prop-1-enyl]pyrrolidine-1-carboxylate in the same way as Intermediate XL, step B.

Intermediate XLVII $N^1,N^1$-Dimethyl-$N^3$-propylpropane-1,3-diamine

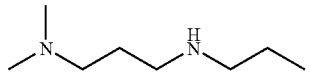

This compound can be prepared as described in International Patent Application WO 93/11758.

Intermediate XLVIII $N^1,N^1$-Dimethyl-$N^4$-propylbutane-1,4-diamine

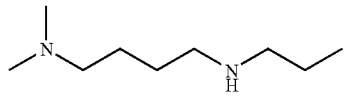

A solution of $N^1,N^1$-dimethylbutane-1,4-diamine (0.64 g, 5.5 mmol) and propionaldehyde (0.38 mL, 5.2 mmol) in 20 mL methanol was stirred at rt overnight. Sodium borohydride (0.31 g, 8.3 mmol) was added and the reaction mixture was stirred for 20 min. The reaction was quenched with 1N NaOH, extracted with ether and washed with brine. Drying, solvent evaporation and flash chromatography (0-12% [10% NH$_4$OH/MeOH]/CH$_2$Cl$_2$) gave $N^1,N^1$-dimethyl-$N^4$-propylbutane-1,4-diamine. $^1$H NMR (CDCl$_3$) δ 2.61 (t, J=6.7 Hz, 2H), 2.57 (t, J=7.2 Hz, 2H), 2.26 (t, J=7.0 Hz, 2H), 2.21 (s, 6H), 1.49 (m, 6H), 0.91 (t, J=7.4 Hz, 3H).

Intermediate XLIX tert-butyl((1R)-1-benzyl-1-methyl-2-oxoethyl)carbamate

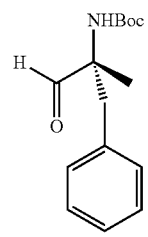

Step A: Reduction

To a solution of alpha-methyl-D-phenylalanine (1.74 g, 9.71 mmol) in 30 mL THF at rt was added NaBH$_4$ (0.92 g 24.27 mmol) in one portion. The solution was cooled to 0° C. Iodine (2.46 g, 9.71 mmol) in 5 mL THF was added dropwise over 30 min. After the addition was complete, the reaction was heated to reflux for 2 days. The reaction was then cooled to 0° C. and quenched by the addition of methanol until the bubbling subsided. The reaction mixture was acidified by the addition of 6N HCl until pH 1, stirred at 50° C. for 30 min and concentrated in vacuo. Purification using ion exchange chromatography (SCX cartridge) afforded (R)-2-amino-2-methyl-3-phenylpropan-1-ol as a white solid. $^1$H NMR (400 MHz, CDCl$_3$) δ 7.35-7.18 (m, 5H), 3.36 (A of AB, d, J=10.4 Hz, 1H), 3.31 (B of AB, d, J=10.4 Hz, 1H), 2.70 (s, 2H), 1.04 (s, 3H).

Step B: Boc Protection

A solution of (R)-2-amino-2-methyl-3-phenylpropan-1-ol (4.14 g, 25 mmol) and di-tertbutyldicarbonate (7.1 g, 32.5 mmol) was stirred at rt for 16 h, concentrated in to provide tert-butyl((1R)-1-benzyl-2-hydroxy-1-methylethyl)carbamate, as a white solid. $^1$H NMR (400 MHz, CDCl$_3$) δ 7.35-7.15 (m, 5H), 4.48 (br s, 1H), 4.17 (br s, 1H), 3.76-3.62 (m, 2H), 3.19 (A of AB, d, J=13.6 Hz, 1H), 2.81 (B of AB, d, J=13.6 Hz, 1H), 1.47 (s, 9H), 1.07 (s, 3H).

Step C: Oxidation

To a solution of tert-butyl((1R)-1-benzyl-2-hydroxy-1-methylethyl)carbamate (6.7 g, 25.2 mmol) in DCM (100 mL) and DMSO (25 mL) was added triethylamine (10.5 mL, 75.7 mmol) and sulfurtrioxide-pyridine (10 g, 63.1 mmol). The reaction mixture was stirred at rt for 3.5 h, diluted with EtOAc, washed with 10% KHSO4, saturated NaHCO3, water, brine and aq LiCl, dried over sodium sulfate, concentrated in vacuo and purified by flash chromatography (silica, 0-20% EtOAc/hexanes) to provide tert-butyl ((1R)-1-benzyl-1-methyl-2-oxoethyl)carbamate as a white solid. $^1$H NMR (400 MHz, CDCl$_3$) δ 9.53 (s, 1H), 7.35-7.22 (m, 3H), 7.12-7.00 (m, 2H), 4.84 (br s, 1H), 3.17 (A of AB, d, J=13.6 Hz, 1H), 3.08 (B of AB, d, J=13.6 Hz, 1H), 1.51 (s, 9H), 1.27 (s, 3H).

Intermediate L (R)-2-tert-Butoxycarbonylamino-2-methyl-3-phenyl-propanal oxime

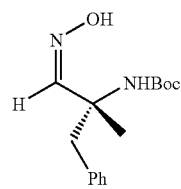

A solution of (R)-2-tert-butoxycarbonylamino-2-methyl-3-phenylpropanal (80 mg, 0.30 mmol), hydroxylamine hydrochloride (25 mg, 0.36 mmol) and triethylamine (0.125 mL, 0.9 mmol) in 3.4 mL ethanol was heated to reflux temperature overnight. Additional hydroxylamine hydrochloride (25 mg, 0.36 mmol) and triethylamine (0.125 mL, 0.9 mmol) were added and the reaction continued at reflux temperature for 4.5 h. Concentration and flash chromatography (0-25% EtOAc/hexanes) gave (R)-2-tert-butoxycarbonylamino-2-methyl-3-phenylpropanal oxime. $^1$H NMR (CDCl$_3$) δ 7.95 (bs, 1H), 7.52 (bs, 1H), 7.25 (m, 3H), 7.10 (d, J=6.7 Hz, 2H), 5.01 (s, 1H), 3.14 (m, 2H), 1.46 (s, 9H), 1.42 (s, 3H).

Intermediate LI 3-(5-((2R)-2-tert-Butoxycarbonylamino-1-phenyl-propan-2-yl)-1,3,4-oxadiazol-2-yl)-5-(2-(carbonitrile)phenyl)-N-methyl-N-(methylsulfonyl)benzenamine

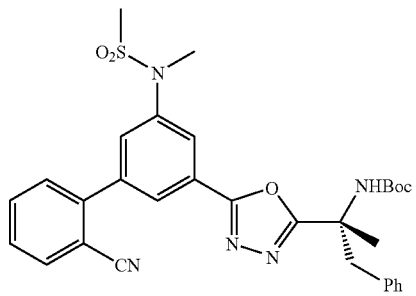

To a degassed solution of 3-(5-((2R)-2-tert-butoxycarbonylamino-1-phenylpropan-2-yl)-1,3,4-oxadiazol-2-yl)-5-bromo-N-methyl-N-(methylsulfonyl)benzenamine (50 mg, 0.088 mmol) (Intermediate XXIX) and 2-cyanophenylzinc bromide (0.5M in THF, 1.1 mL, 0.53 mmol) was added tetrakis(triphenylphosphine)palladium(0) (10.2 mg, 0.0088 mmol). The reaction was heated in a microwave oven to 80° C. for 10 min, diluted with water and extracted with EtOAc. The combined organic layers were washed with brine. Drying, solvent evaporation and flash chromatography (0-65% EtOAc/hexanes) gave 3-((2R)-5-(2-tert-butoxycarbonylamino-1-phenylpropan-2-yl)-1,3,4-oxadiazol-2-yl)-5-(2-(carbonitrile)phenyl)-N-methyl-N-(methylsulfonyl)benzenamine. $^1$H NMR (CDCl3) δ 8.10 (m, 2H), 7.82 (m, 2H), 7.73 (m, 1H), 7.61 (d, J=7.9 Hz, 1H), 7.54 (m, 1H), 7.28 (m, 3H), 7.07 (m, 2H), 3.60 (d, J=16 Hz, 1H), 3.45 (m, 4H), 2.97 (s, 3H), 1.54 (s, 3H), 1.43 (s, 9H).

Intermediate LII 3-(5-((2R)-2-tert-Butoxycarbonylamino-1-phenyl-propan-2-yl)-1,3,4-oxadiazol-2-yl)-5-(2-(aminomethyl)phenyl)-N-methyl-N-(methylsulfonyl)benzenamine

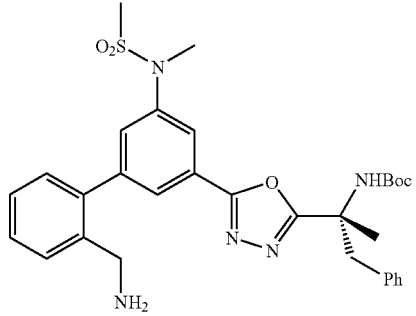

A solution of 3-(5-(2-tert-butoxycarbonylamino-1-phenylpropan-2-yl)-1,3,4-oxadiazol-2-yl)-5-(2-(carbonitrile)

phenyl)-N-methyl-N-(methylsulfonyl)benzenamine (130 mg, 0.22 mmol) in 25 mL ethanol saturated with ammonia was stirred in the presence of Raney nickel (50% slurry in water, washed with ethanol, catalytic amount) under a hydrogen atmosphere for 2 h. The reaction mixture was filtered over celite and concentrated to give 3-(5-((2R)-2-tert-butoxycarbonylamino-1-phenylpropan-2-yl)-1,3,4-oxadiazol-2-yl)-5-(2-(aminomethyl)phenyl)-N-methyl-N-(methylsulfonyl)benzenamine. $^1$H NMR (CD$_3$OD) δ 8.03 (s, 1H), 7.82 (s, 1H), 7.68 (s, 1H), 7.56 (d, J=7.5 Hz, 1H), 7.45 (m, 1H), 7.38 (t, J=7.5 Hz, 1H), 7.24 (m, 4H), 7.10 (m, 2H), 3.77 (s, 2H), 3.55 (m, 1H), 3.42 (s, 3H), 3.34 (m, 1H), 2.98 (s, 3H), 1.60 (s, 3H), 1.39 (bs, 9H).

Intermediate LIII tert-butyl((1R)-3-amino-1-benzyl-2-hydroxy-1-methylpropyl)carbamate

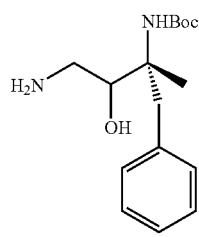

Step A: Epoxidation

To a solution of N-(tert-butyl((1R)-1-benzyl-1-methyl-2-oxoethyl)carbamate (Intermediate XLIX, 1 g, 3.80 mmol) in acetonitrile (15 mL) was added 6 drops water, trimethylsulfonium iodide (775 mg, 3.80 mmol) and potassium hydroxide (511 mg, 9.11 mmol). The reaction was stirred at 60° C., sealed, for 1.5 h, additional trimethylsulfonium iodide (775 mg, 3.80 mmol) and potassium hydroxide (511 mg, 9.11 mmol) were added and the reaction was stirred at 60° C., sealed, for 3 h. the reaction mixture was diluted with EtOAc, washed with sat'd aq NaHCO$_3$, brine, dried over sodium sulfate, and concentrated in vacuo to provide tert-butyl((1R)-1-methyl-1-oxiran-2-yl-2-phenylethyl)carbamate as an oil. MS (ES, M+H) 278.

Step B: Epoxide Opening

A solution of tert-butyl((1R)-1-methyl-1-oxiran-2-yl-2-phenylethyl)carbamate (986 mg, 3.56 mmol) in EtOH (35 mL) and NH$_4$OH (35 mL) was stirred at 60° C., sealed, for 16 h, concentrated in vacuo and purified by flash chromatography (silica, 0-30% (10% NH$_4$OH/MeOH)/CH$_2$Cl$_2$) to provide tert-butyl ((1R)-3-amino-1-benzyl-2-hydroxy-1-methylpropyl)carbamate as a thick oil. $^1$H NMR (400 MHz, CD$_3$OD, 1:1 diastereomeric mixture) δ 7.30-7.14 (m, 5H), 4.01 (br d, J=9.2 Hz, 0.5H), 3.54 (dd, J=10.0, 2 Hz, 0.5H), 3.39 (br s, 0.5H), 3.36 (br s, 0.5H), 2.94-2.56 (m, 4H), 1.47 (s, 9H), 1.03 (s, 1.5H), 0.99 (s, 1.5H).

Intermediate LIV methyl-2-{3-[5-((1R)-1-(tert-Butoxycarbonylamino)-1-methyl-2-phenylethyl)-1,3,4-oxadiazol-2-yl]-5-[(dipropylamino)carbonyl]phenyl}-3-furoate

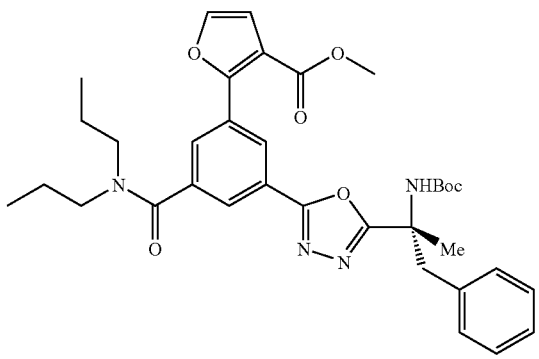

To the mixture of Intermediate XXXIV (0.030 g, 0.051 mmol) and Pd(PPh$_3$)$_4$ (0.004 g, 0.003 mmol) in degassed DMF (0.6 mL) under argon was added Na$_2$CO$_3$ (0.014 g, 0.128 mmol, dissolved in minimum amount of water) and Intermediate XXXVI (0.011 g, 0.067 mmol). After the reaction mixture was purged with argon, it was heated at 120° C. for 18 h. After cooling to rt, the reaction was filtered and the organic layer was purified by reverse phase preparative HPLC (5-95% MeCN/H$_2$O containing 0.1% TFA, C18 PRO YMC 20×150 mm) to give desired methyl-2-{3-[5-(1-(tert-Butoxycarbonyl amino)-1-methyl-2-phenylethyl)-1,3,4-oxadiazol-2-yl]-5-[(dipropylamino)carbonyl]phenyl}-3-furoate. LCMS [M+H]$^+$=631.

Intermediate LV

2-{3-[5-((1R)-1-(tertbutoxycarbonylamino)-1-methyl-2-phenylethyl)-1,3,4-oxadiazol-2-yl]-5-[(dipropylamino)carbonyl]phenyl}-3-furoic acid

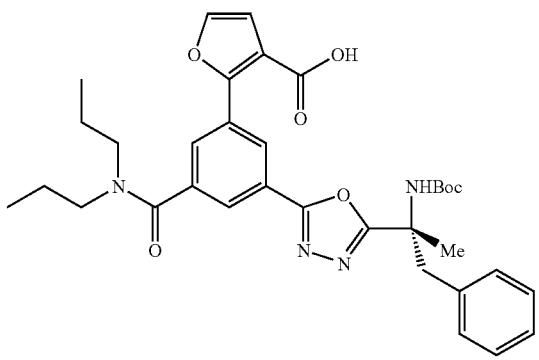

To a solution of Intermediate LIV (0.004 g, 0.006 mmol) in 0.15 mL of THF was added 1N LiOH (0.056 mL, 0.056 mmol). After 50 hr at rt, the reaction was quenched by the addition of 1N HCl (0.060 mL, 0.060 mmol) and purified by reverse phase preparative HPLC (5-95% MeCN/H$_2$O containing 0.1% TFA, C18 PRO YMC 20×150 mm) to give the desired acid G as white solid. $^1$H NMR (CDCl$_3$) δ 8.75 (s, 1H), 8.23 (s, 1H), 8.05 (s, 1H), 7.51 (d, J=1.9 Hz, 1H), 7.28-7.26 (m, 3H), 7.07-7.06 (m, 2H), 6.90 (d, J=1.8 Hz, 1H), 5.24 (s, 1H), 3.59-3.26 (m, 6H), 1.73-1.40 (m, 16H), 1.02-0.99 (m, 3H), 0.79-0.75 (m, 3H). LCMS [M+H]$^+$=617

Intermediate LVI

2-{3-[5-((1R)-1-amino-1-methyl-2-phenylethyl)-1,3,4-oxadiazol-2-yl]-5-[(dipropylamino)carbonyl]phenyl}-3-furamide

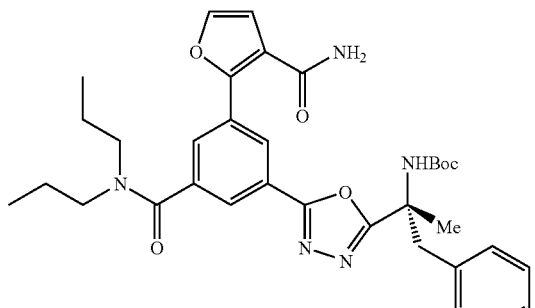

To a solution of Intermediate LV (0.026 g, 0.042 mmol) in 0.4 mL of DMF was added ammonium chloride (0.005 g, 0.084 mmol), EDC (0.016 g, 0.084 mmol), HOAt (0.011 g, 0.084 mmol) and diisopropylethylamine (0.022 g, 0.169 mmol). The reaction was stirred at rt for 5 h and purified by reverse phase preperative HPLC (5-95% MeCN/H$_2$O containing 0.1% TFA, C18 PRO YMC 20×150 mm) to give the desired amide as a white solid. LCMS [M+H]$^+$=616.

Intermediate LVII

N-[(1R)-1-(4-fluorophenyl)ethyl]-3-(5-formyl-2-furyl)-5-[methyl (methylsulfonyl)amino]benzamide

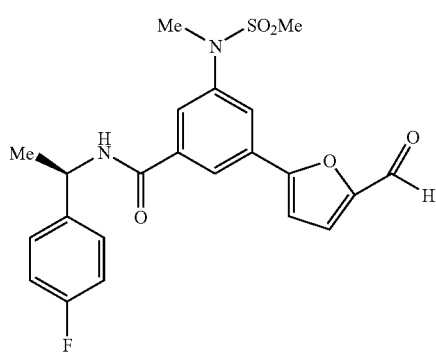

To a solution of Intermediate X (0.280 g, 0.65 mmol) and (5-formyl-2-furyl)boronic acid (0.0912 g, 0.65 mmol) in 5 mL degassed DMF was added TPPTS (0.111 g, 0.20 mmol) Pd(OAc)$_2$ (0.015 g, 0.07 mmol) and diisopropylamine (0.066 g, 0.65 mmol). After 15 h at rt, the reaction was diluted with satd. aqueous NaHCO3 and EtOAc, and the layers were separated. The organics were washed with brine, dried over Na2SO4, filtered and concentrated. Purification by normal phase chromatography (50->100% EtOAc/hexanes) afforded the desired coupled adduct. $^1$H NMR (400 MHz, CDCl$_3$) δ 9.67 (s, 1H), 8.09 (m, 1H), 7.95 (m, 1H), 7.84 (m, 1H), 7.41-7.34 (m, 3H), 7.08 (m, 2H), 6.99 (d, J=5.9 Hz, 1H), 6.54 (d, J=7.5 Hz, 1H), 5.31 (m, 1H), 3.40 (s, 3H), 2.89 (s, 3H), 1.65 (d, J=7.0 Hz, 3H). LCMS [M+H]$^+$=445.

Intermediate LVIII 3-(5-{([tert-butylsulfinyl)imino]methyl}-2-furyl)-[(1R)-1-(4-fluorophenyl)ethyl]-5-[methyl(methylsulfonyl)amino]benzamide

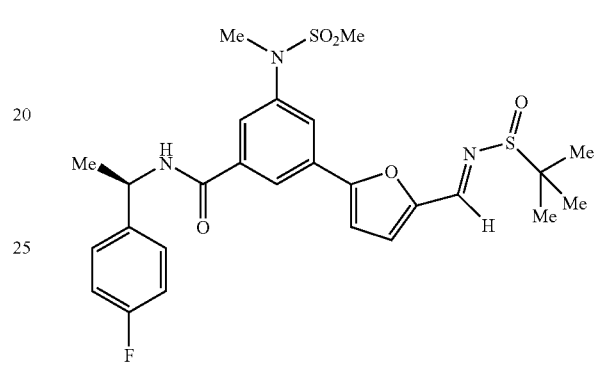

To a solution of Intermediate LVII (0.250 g, 0.56 mmol) in 10 mL CH$_2$Cl$_2$ was added racemic Ellman sulfinamide (0.136 g, 1.12 mmol) and CuSO$_4$ (1.34 g, 8.43 mmol). The slurry was allowed to stir at rt overnight, then filtered through a pad of celite, rinsing with EtOAc. The organics were partitioned between satd. NaHCO$_3$ and EtOAc, the layers were separated, the organic layer was dried over Na$_2$SO$_4$, filtered and concentrated to afford the title compound, which was used without further purification. LCMS [M+H]$^+$=548.

Intermediate LIX 3-(5-{(1R)-1-[(tert-butoxycarbonyl)amino]-1-methyl-2-phenylethyl}-1,3,4-oxadiazol-2-yl)-5-[ethyl (methylsulfonyl)amino]benzoic acid

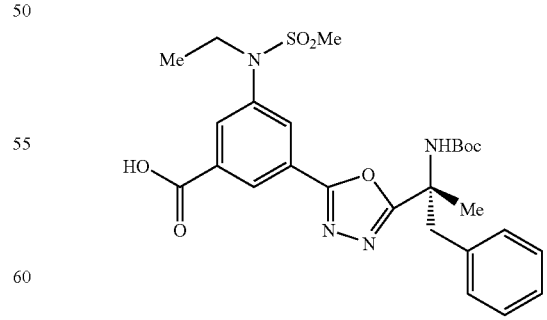

Prepared using a procedure similar to that employed for the synthesis of Intermediate VI, substituting ethyl iodide in the place of methyl iodide in Step B of the Intermediate III synthesis.

Intermediate LX 3-(5-{(1R)-1-[(tert-butoxycarbonyl)amino]-1-methyl-2-phenylethyl}-1,3,4-oxadiazol-2-yl)-5-[propyl (methylsulfonyl)amino]benzoic acid

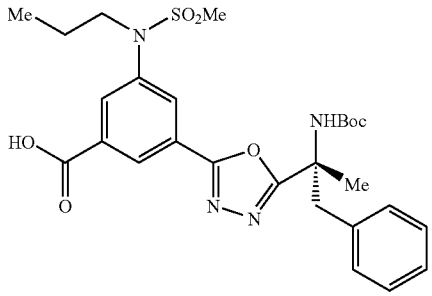

Prepared using a procedure similar to that employed for the synthesis of Intermediate VI, substituting propyl iodide in the place of methyl iodide in Step B of the Intermediate III synthesis.

Intermediate LXI 3-(5-{(1R)-1-[(tert-butoxycarbonyl)amino]-1-methyl-2-phenylethyl}-1,3,4-oxadiazol-2-yl)-5-[methyl (isopropylsulfonyl)amino]benzoic acid

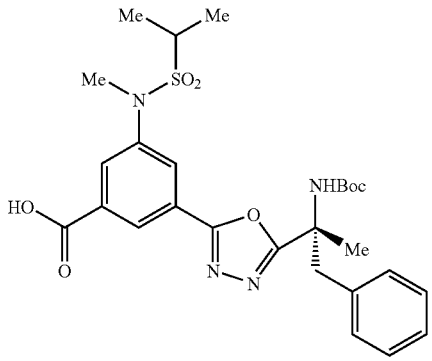

Prepared using a procedure similar to that employed for the synthesis of Intermediate VI, substituting isopropyl sulfonyl chloride in the place of methanesulfonyl chloride in Step A of the Intermediate III synthesis.

Intermediate LXII

Dimethyl-5-trifluoromethyl isophthalate

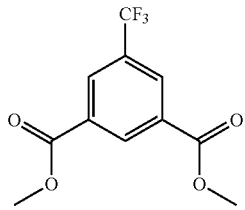

To a solution of dimethyl 5-iodoisophthalate (1 g, 3.12 mmol) in 1:1 DMF/HMPA was added Methyl-2,2-difluoro-2(fluorosulfonyl)acetate (3 g, 15.6 mmol) and Copper (I) Iodide (2.9 mg, 15.6 mmol) and the reaction mixture heated to 80 C for 16 h. The reaction was cooled to rt and diluted with ethyl acetate (200 mL) The solvent was decanted and the copper salts washed with an additional 100 mL of ethyl acetate. The organics were poured into water (200 mL) the phases separated and the aqueous extracted with Ethyl acetate (100 mL) dried over anhydrous sodium sulfate, filtered and concentrated at reduced pressure. The residue was chromatographed on silica gel eluting with dichloromethane. to give dimethyl-5-trifluoromethyl isophthalate: $^1$H NMR (400 MHz, CDCl$_3$) δ 8.85 (s, 1H), 8.48 (s, 2H), 4.01 (s, 6H). LCMS [(M)+H]$^+$=263.

Intermediate LXIII tert-butyl)-{(1R)-1-[5-(2'-cyano-3'-fluoro-5-{[(2)-2-prop-1-yn-1-ylpyrrolidin-1-yl]carbonyl}biphenyl-3-yl)-1,3,4-oxadiazol-2-yl]-1-methyl-2-phenylethyl}carbamate

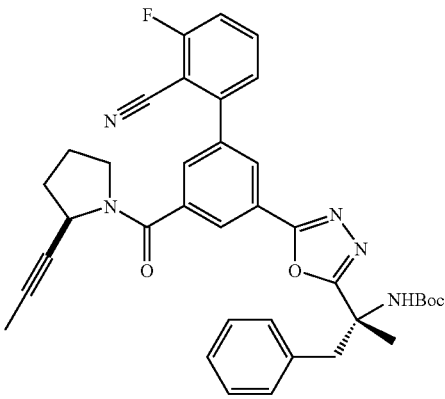

Prepared using a procedure similar to that described for the synthesis of Intermediate XVIII, followed by coupling the resulting acid with (2R)-2-prop-1-ynylpyrrolidine (Intermediate XL) under standard amide bond forming conditions.

Intermediate LIX tert-butyl((1R)-1-{5-[5-(bromomethyl)-2'-cyanobiphenyl-3-yl]-1,3,4-oxadiazol-2-yl}-1-methyl-2-phenylethyl)carbamate

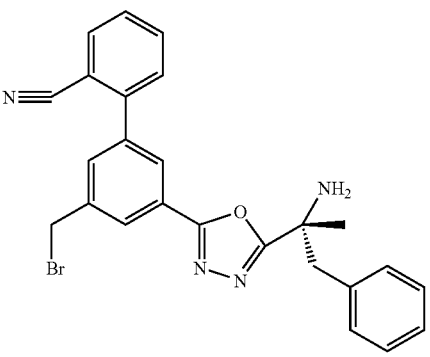

Prepared from Intermediate XIX, using a procedure as described for the synthesis of Intermediate XXX.

Example 1

3-{5-[(1R)-1-amino-1-methyl-2-phenylethyl]-1,3,4-oxadiazol-2-yl}-N-[(1R)-1-(4-fluorophenyl)ethyl]-5-[methyl(methylsulfonyl)amino]benzamide

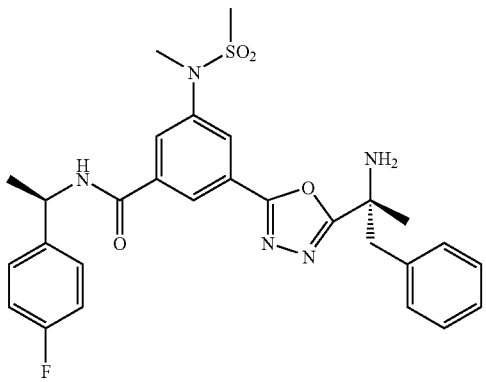

Step A: Amide Bond Formation

To a solution of Intermediate V (0.076 g, 0.143 mmol) in 1.5 mL CH$_2$Cl$_2$ was added (1R)-1-(4-fluorophenyl)ethanamine (0.030 mL, 0.215 mmol), followed by diisopropylethylamine (0.075 mL, 0.430 mmol) and BOP-reagent (0.095 g, 0.215 mmol). After 20 min at rt, the reaction was loaded directly onto a silica gel column equilibrated with 30% EtOAc/hexanes, and purified by normal phase chromatography (30->75% EtOAc/hexanes) to obtain the desired amide as a white foam. $^1$H NMR (CDCl$_3$) δ 8.29 (s, 1H), 8.12 (s, 1H), 7.98 (s, 1H), 7.38-7.7.35 (m, 2H), 7.29-7.24 (m, 3H), 7.08-7.02 (m, 4H), 6.52 (d, J=7.5 Hz, 1H), 5.30 (m, 1H), 3.60 (d, J=13.4 Hz, 1H), 3.40 (d, J=13.4 Hz, 1H), 3.40 (s, 3H), 2.88 (s, 3H), 1.69 (s, 3H), 1.62 (d, J=7.0 Hz, 3H) 1.40 (s, 9H). LCMS [M+H]$^+$=652.

Step B: Boc Deprotection

Gaseous HCl was bubbled through a solution of amide (0.068 g, 0.104 mmol) from step A in 6 mL CH$_2$Cl$_2$ at 0° C. for 10 min. The reaction was warmed to rt for 20 min, cooled back to 0° C. and HCl was bubbled through the solution for a further 5 min. After 30 minutes at rt, the reaction was concentrated, and the residue was freeze dried to obtain a flocculent white solid. The two diastereomers at the right hand amine stereocenter were separated by chiral chromatography (5×50 cm Chiracel AD column, 100% EtOH, 40 mL/min, R$_t$=4.419 and 5.941 min). The slower eluting isomer was the active diastereomer (R$_t$=5.941 min). $^1$H NMR (d$_4$-MeOH) δ 9.07 (d, J=7.5 Hz, 1H), 8.38 (d, J=1.5 Hz, 1H), 8.20 (d, J=1.8 Hz, 1H), 8.12 (d, J=1.6 Hz, 1H), 7.45-7.42 (m, 2H), 7.30-7.28 (m, 3H), 7.09-7.03 (m, 4H), 5.25 (m, 1H), 3.44 (s, 2H), 3.40 (s, 3H), 3.00 (s, 3H), 1.87 (s, 3H), 1.59 (d, J=7.1 Hz, 3H). HRMS exact mass calc for C$_{28}$H$_{31}$FN$_5$O$_4$S [M+H]$^+$: 552.2076; observed: 552.2088.

Example 2

3-{5-[(1R)-1-amino-1-methyl-2-phenylethyl]-1,3,4-oxadiazol-2-yl}-N-[(1R)-1-(4-fluorophenyl)ethyl]-5-[methyl(isopropylsulfonyl)amino]benzamide

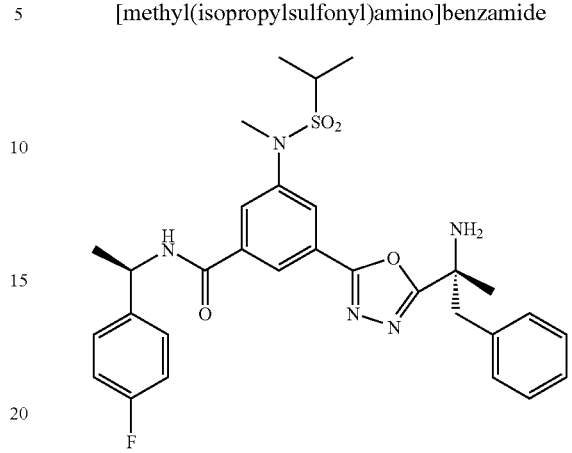

This compound was prepared in a similar manner to Example 1, using Intermediate LXI. HRMS exact mass calc for C$_{30}$H$_{35}$FN$_5$O$_4$S [M+H]$^+$: 580.2394; observed: 580.2389.

Example 3

3-{5-[(1R)-1-amino-1-methyl-2-phenylethyl]-1,3,4-thiadiazol-2-yl}-N-[(1R)-1-(4-fluorophenyl)ethyl]-5-[methyl(methylsulfonyl)amino]benzamide

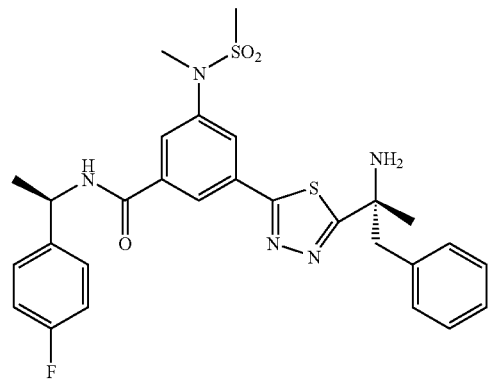

Step A: Thiadiazole Formation

To a solution of Intermediate IV (0.110 g, 0.196 mmol) in 2.5 mL CH$_3$CN was added Lawesson's reagent (0.103 g, 20.254 mmol). The slurry was heated 50° C. for 5 h. The reaction mixture was concentrated, redissolved in a minimum volume of CH$_2$Cl$_2$ and loaded directly onto a silica gel column equilibrated with 10% EtOAc/hexanes, and purified using normal phase chromatography (10->65% EtOAc/hexanes) to afford the desired thiodiazole as a white foam. $^1$H NMR (CDCl$_3$) δ 8.40 (app. t, J=1.5 Hz, 1H), 8.23 (app. t, J=2.2 Hz, 1H), 8.13 (m, 1H), 7.28-7.24 (m, 3H), 7.11-7.08 (m, 2H), 5.14 (br s, 1H), 3.94 (s, 3H), 3.41-3.38 (m, 2H), 2.90 (s, 3H), 2.54 (s, 3H), 1.69 (s, 3H), 1.43 (s, 9H). LCMS [M+H]$^+$=561.

Step B: Ester Hydrolysis

To a solution of methyl ester (0.068 g, 0.209 mmol) from step A in 1.5 mL THF was added 1N LiOH (0.364 mL, 0.364 mmol). After 1.5 h at rt, the reaction was quenched by the addition of 1N HCl (0.485 mL, 0.485 mmol) and diluted with EtOAc and H₂O. The layers were separated, and the aqueous layer was extracted with EtOAc (3×). The combined organics were dried over Na₂SO₄, filtered and concentrated to afford the desired acid as a white foam. The acid was used without further purification. ¹H NMR (CDCl₃) δ 8.44 (s, 1H), 8.28 (s, 1H), 8.19 (s, 1H), 7.30-7.24 (m, 3H), 7.12-7.10 (m, 2H), 3.81-3.71 (m, 2H), 3.43-3.40 (m, 2H), 3.40 (s, 3H), 2.92 (s, 3H), 2.55 (s, 3H), 1.74 (s, 3H), 1.43 (s, 9H). LCMS [M+H]⁺=547.

Step C: Amide Bond Formation

To a solution of acid from step B (0.066 g, 0.121 mmol) in 2.0 mL CH₂Cl₂ was added (1R)-1-(4-fluorophenyl)ethanamine (0.024 mL, 0.181 mmol), followed by diisopropylethylamine (0.063 mL, 0.362 mmol) and BOP-reagent (0.080 g, 0.181 mmol). After 30 min at rt, the reaction was loaded directly onto a silica gel column equilibrated with 30% EtOAc/hexanes, and purified by normal phase chromatography (30->80% EtOAc/hexanes) to obtain the desired amide as a white foam. ¹H NMR (CDCl₃) δ 8.22 (t, J=1.3 Hz, 1H), 8.06 (t, J=1.9 Hz, 1H), 7.92 (t, J=1.6 Hz, 1H), 7.36-7.30 (m, 2H), 7.29-7.24 (m, 3H), 7.11-7.08 (m, 2H), 7.04-7.01 (m, 2H), 6.66 (d, J=7.5 Hz, 1H), 5.27 (m, 1H), 5.10 (br s, 1H), 3.71 (d, J=13.5 Hz, 1H), 3.38 (d, J=13.4 Hz, 1H), 3.40 (s, 3H), 2.88 (s, 3H), 1.69 (s, 3H), 1.62 (d, J=7.0 Hz, 3H) 1.40 (s, 9H). LCMS [M+H]⁺=652.

Step D: Boc Deprotection

To a solution of amide (0.074 g, 0.111 mmol) from step C in 1.50 mL CH₂Cl₂ was added TFA (0.433 mL, 4.43 mmol). After 6 h at rt the reaction was concentrated, redissolved in DMF and purified by preparative HPLC (5->95% CH₃CN/H₂O, 0.1% added TFA, C18 PRO YMC 20×150 mm) to afford 3-{5-[(1R)-1-amino-1-methyl-2-phenylethyl]-1,3,4-thiadiazol-2-yl}-N-[(1R)-1-(4-fluorophenyl)ethyl]-5-[methyl(methylsulfonyl)amino]benzamide as its trifluoroacetate salt. ¹H NMR (d₄-MeOH) δ 9.03 (d, J=7.7 Hz, 1H), 8.31 (t, J=1.3 Hz, 1H), 8.20 (t, J=1.8 Hz, 1H), 8.05 (t, J=1.8 Hz, 1H), 7.44-7.40 (m, 2H), 7.31-7.27 (m, 3H), 7.09-7.02 (m, 4H), 5.25 (m, 1H), 3.47 (d, J=13.5 Hz, 1H), 3.41 (d, J=13.5 Hz, 1H), 3.40 (s, 3H), 2.97 (s, 3H), 1.89 (s, 3H), 1.58 (d, J=7.1 Hz, 3H). LC/MS [M+H]=568.

Step A: Oxadiazole Formation

To a solution of Intermediate VII (0.068 g, 0.172 mmol) and Intermediate VIII (0.028 g, 0.095 mmol) in 1.0 mL CH₂Cl₂ was added 0.5M HOBt stock solution in DMF (0.34 mL, 0.172 mmol) followed by diisopropylcarbodiimide (0.027 mL, 0.172 mmol). After 3 h at rt, the reaction was concentrated, and the residue was dissolved in EtOAc. The organic layer washed with satd. aqueous NaHCO₃ (2×), 0.5M aqueous KHSO₄, 3M aqueous LiCl, and brine, then dried over Na₂SO₄, filtered and concentrated. The residue was dissolved in 1.0 mL EtOH and 0.30 mL H₂O, then NaOAc (0.049 g, 0.597 mmol) was added. The reaction was heated to 86° C. for 3 h, cooled to rt and partitioned between EtOAc and hexanes. The layers were separated, and the aqueous layer washed with EtOAc (2×), the combined organics were washed with brine, dried over Na₂SO₄, filtered and concentrated. The residue was purified by normal phase silica gel chromatography (10->70% EA/hex), followed by preparative HPLC (5->95% CH₃CN/H₂O, 0.1% added TFA, C18 PRO YMC 20×150 mm) to afford the desired oxadiazole as a viscous oil. ¹H NMR (CDCl₃) δ 8.29 (s, 1H), 8.12 (s, 1H), 7.98 (s, 1H), 7.38-7.35 (m, 2H), 7.29-7.24 (m, 3H), 7.08-7.02 (m, 4H), 6.52 (d, J=7.5 Hz, 1H), 5.30 (m, 1H), 3.60 (d, J=13.4 Hz, 1H), 3.40 (d, J=13.4 Hz, 1H), 3.40 (s, 3H), 2.88 (s, 3H), 1.69 (s, 3H), 1.62 (d, J=7.0 Hz, 3H) 1.40 (s, 9H). LCMS [M+H]⁺=652.

Step B: Boc Deprotection

To a solution of oxadiazole (0.014 g, 0.021 mmol) from step A in 1.4 mL CH₂Cl₂ was added TFA (0.042 mL, 0.430 mmol). After 3 h, another aliquot of TFA (0.042 mL, 0.430 mmol) was added, and after 15 h at rt, the reaction was concentrated, and the residue was freeze dried to obtain 3-{3-[(1R)-1-amino-1-methyl-2-phenylethyl]-1,2,4-oxadiazol-5-yl}-N-[(1R)-1-(4-fluorophenyl)ethyl]-5-[methyl(methylsulfonyl)amino]benzamide as a flocculent white solid. ¹H NMR (d₄-MeOH) δ 8.55 (t, J=1.4 Hz, 1H), 8.37 (t, J=1.2 Hz, 1H), 8.18 (t, J=2.0 Hz, 1H), 7.43 (dd, J=8.6, 5.3 Hz, 2H), 7.28-7.26 (m, 3H), 7.08-7.04 (m, 4H), 5.26 (m, 1H), 3.41 (s, 3H), 3.35 (s, 2H), 2.98 (s, 3H), 1.77 (s, 3H), 1.59 (d, J=7.1 Hz, 3H). HRMS exact mass calc for C₂₈H₃₁FN₅O₄S [M+H]⁺: 552.2076; observed: 552.2077.

Example 4

3-{3-[(1R)-1-amino-1-methyl-2-phenylethyl]-1,2,4-oxadiazol-5-yl}-N—[(R)-1-(4-fluorophenyl)ethyl]-5-[methyl(methylsulfonyl)amino]benzamide Example 5

3-{5-[(1R)-1-amino-1-methyl-2-phenylethyl]-1,2,4-oxadiazol-3-yl}-N-[(1R)-1-(4-fluorophenyl)ethyl]-5-[methyl(methylsulfonyl)amino]benzamide

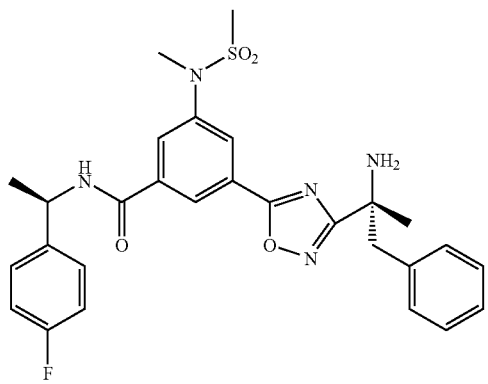

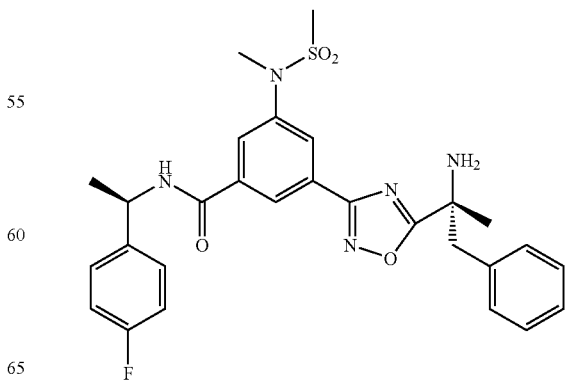

Step A: Oxadiazole Formation

To a solution of (R)—N-Boc-α-methyl phenylalanine (0.061 g, 0.220 mmol) and Intermediate XII (0.050 g, 0.122 mmol) in 1.0 mL CH$_2$Cl$_2$ was added 0.5M HOBt stock solution in DMF (0.44 mL, 0.220 mmol) followed by diisopropylcarbodiimide (0.034 mL, 0.220 mmol). After 1.5 h at rt, the reaction was concentrated, and the residue was dissolved in EtOAc. The organic layer washed with satd. aqueous NaHCO$_3$ (2×), 0.5M aqueous KHSO$_4$, 3M aqueous LiCl, and brine, then dried over Na$_2$SO$_4$, filtered and concentrated. The residue was dissolved in 2.0 mL EtOH and 0.50 mL H$_2$O, then NaOAc (0.140 g, 1.71 mmol) was added. The reaction was heated to 86° C. for 16 h, cooled to rt and partitioned between EtOAc and hexanes. The layers were separated, and the aqueous layer washed with EtOAc (2×), the combined organics were washed with brine, dried over Na$_2$SO$_4$, filtered and concentrated. The residue was purified by normal phase silica gel chromatography (30->80% EA/hex) to afford the desired oxadiazole as a viscous oil. $^1$H NMR (CDCl$_3$) δ 8.27 (s, 1H), 8.20 (t, J=2.2 Hz, 1H), 7.97 (d, J=2.1 Hz, 1H), 7.37-7.7.34 (m, 2H), 7.29-7.24 (m, 3H), 7.05-7.01 (m, 4H), 6.42 (d, J=7.3 Hz, 1H), 5.30 (q, J=7.5 Hz, 1H), 5.09 (br s, 1H), 3.57 (d, J=13.5 Hz, 1H), 3.43 (d, J=13.5 Hz, 1H), 3.37 (s, 3H), 2.88 (s, 3H), 1.70 (s, 3H), 1.61 (d, J=7.0 Hz, 3H) 1.42 (s, 9H). LCMS [(M-tBu)+H]$^+$=596.

Step B: Boc Deprotection

Gaseous HCl was bubbled through a solution of oxadiazole (0.029 g, 0.044 mmol) from step A in 4 mL CH$_2$Cl$_2$ at 0° C. for ~10 min. After 40 min at rt, the reaction was concentrated, the residue was purified by preparative HPLC (5->95% CH$_3$CN/H$_2$O, 0.1% added TFA, C18 PRO YMC 20×150 mm), and the fractions containing the desired product were freeze dried to obtain 3-{5-[(1R)-1-amino-1-methyl-2-phenylethyl]-1,2,4-oxadiazol-3-yl}-N-[(1R)-1-(4-fluorophenyl)ethyl]-5-[methyl (methylsulfonyl)amino]benzamide as a flocculent white solid. $^1$H NMR (d$_4$-MeOH) δ 9.05 (d, J=7.4 Hz, 1H), 8.43 (t, J=1.4 Hz, 1H), 8.25 (t, J=1.8 Hz, 1H), 8.05 (s, 1H), 7.43 (dd, J=8.4, 5.5 Hz, 2H), 7.29-7.27 (m, 3H), 7.07-7.02 (m, 4H), 5.25 (q, J=7.0 Hz, 1H), 3.43 (d, J=13.7 Hz, 1H), 3.41-3.38 (m, 4H), 2.95 (s, 3H), 1.85 (s, 3H), 1.57 (d, J=7.0 Hz, 3H). HRMS exact mass calc for C$_{28}$H$_{31}$FN$_5$O$_4$S [M+H]$^+$: 552.2076; observed: 552.2104.

Example 6

3-{3-[(1R)-1-amino-1-methyl-2-phenylethyl]-1H-1,2,4-triazol-5-yl}-N-[1)-1-(4-fluorophenyl)ethyl]-5-[methyl(methylsulfonyl)amino]benzamide

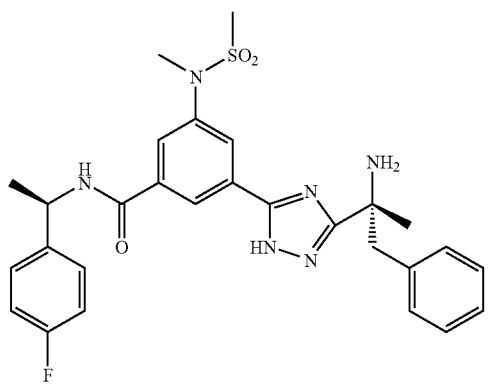

Step A: Triazole Formation

To a solution of Intermediate II (0.157 g, 0.534 mmol) and Intermediate XIII (0.075 g, 0.178 mmol) in 1.5 mL EtOH was stirred at 0° C. for 2 h. The reaction was then heated to reflux for 41 h, cooled to rt, and concentrated. The residue was redissolved in 0.85 mL DMF and purified by preparative HPLC (5->95% CH$_3$CN/H$_2$O, 0.1% added TFA, C18 PRO YMC 20×150 mm) to afford the desired triazole as a viscous oil. $^1$H NMR (CDCl$_3$) δ 8.39 (s, 1H), 8.16 (s, 1H), 7.91 (s, 1H), 7.37 (dd, J=8.6, 5.3 Hz, 2H), 7.26-7.24 (m, 3H), 7.07-6.97 (m, 4H), 5.31-5.26 (m, 1H), 3.64 (d, J=13.0 Hz, 1H), 3.32 (s, 3H), 3.17 (d, J=13.0 Hz, 1H), 2.84 (s, 3H), 1.70 (s, 3H), 1.60 (d, J=7.0 Hz, 3H) 1.42 (s, 9H). LCMS [M+H]$^+$=651.

Step B: Boc Deprotection

To a solution of triazole (0.032 g, 0.049 mmol) from Step A in 1.2 mL CH$_2$Cl$_2$ was added TFA (0.146 mL, 1.97 mmol). After 15 h at rt, the reaction was concentrated, the residue was purified by preparative HPLC (5->95% CH$_3$CN/H$_2$O, 0.151% added TFA, C18 PRO YMC 20×150 mm), and the fractions containing the desired product were freeze dried to obtain 3-{3-[(1R)-1-amino-1-methyl-2-phenylethyl]-1H-1,2,4-triazol-5-yl}-N-[(1)-1-(4-fluorophenyl)ethyl]-5-[methyl(methylsulfonyl)amino]benzamide as a flocculent white solid. $^1$H NMR (d$_4$-MeOH) δ 8.40 (s, 1H), 8.22 (s, 1H), 7.98 (s, 1H), 7.43 (dd, J=8.6, 5.3 Hz, 2H), 7.23-7.22 (m, 3H), 7.06 (app. t, J=8.8 Hz, 2H), 6.96 (m, 2H), 5.25 (q, J=7.1 Hz, 1H), 3.40 (s, 3H), 3.35-3.28 (m, 2H), 2.98 (s, 3H), 1.75 (s, 3H), 1.58 (d, J=7.0 Hz, 3H). HRMS exact mass calc for C$_{28}$H$_{32}$FN$_6$O$_3$S [M+H]$^+$: 551.2235; observed: 551.2247.

Example 7

N-{3-{5-[(1R)-1-amino-1-methyl-2-phenylethyl]-1,3,4-oxadiazol-2-yl}-5-[(Z)-2-(2-methylcyclopropyl)vinyl]phenyl}-N-propylmethanesulfonamide

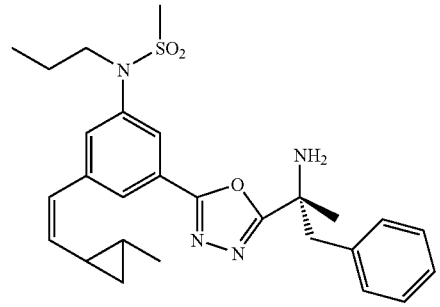

Step A: Coupling

To a slurry of Intermediate II (0.110 g, 0.375 mmol) and Intermediate XV (0.110 g, 0.326 mmol) in 3 mL CH$_2$Cl$_2$ was added diisopropylethylamine (0.171 mL, 0.978 mmol), followed by BOP-reagent (0.216 g, 0.489 mmol). After 40 min. at rt, the reaction was loaded directly onto a silica gel column equilibrated with 10% EtOAc/hexanes, and purified using normal phase chromatography (10->55% EtOAc/hexanes). The desired product was obtained as a white foam. $^1$H NMR (CDCl$_3$) δ 9.40 (br s, 1H), 8.83 (br s, 1H), 7.76 (s, 1H), 7.62 (s, 2H), 7.33-7.24 (m, 3H), 7.15 (d, J=6.4 Hz, 2H), 6.27 (d, J=11.3 Hz, 1H), 5.22 (dd, J=11.2, 10.1 Hz, 1H), 4.68 (s, 1H), 3.64 (t, J=7.1 Hz, 2H), 3.53 (d, J=13.6 Hz, 1H), 3.07 (d, J=13.5 Hz, 1H), 2.87 (s, 3H), 2.03 (s, 3H), 1.53-1.45 (m, 2H), 1.48 (s, 9H), 1.12 (d, J=5.9 Hz, 3H), 0.92-0.87 (m, 5H), 0.69-0.64 (m, 2H), LCMS [(M-Boc)+H]$^+$=513.

Step B: Dehydrative Cyclization

To a solution of adduct from Step A (0.082 g, 0.134 mmol) in 1.5 mL 1,2-dichloroethane was added Burgess reagent (0.128 g, 0.535 mmol). The slurry was microwaved at 120° C. for 10 min. The reaction mixture was loaded directly onto a silica gel column equilibrated with 10% EtOAc/hexanes, and purified using normal phase chromatography (10->50% EtOAc/hexanes) to afford the desired oxadiazole as a white foam. $^1$H NMR (CDCl$_3$) δ 7.97 (s, 1H), 7.81 (s, 1H), 7.58 (s, 1H), 7.27-7.24 (m, 3H), 7.05-7.04 (m, 2H), 6.31 (d, J=11.5 Hz, 1H), 5.22 (dd, J=11.2, 10.3 Hz, 1H), 5.08 (br s, 1H), 3.68 (t, J=7.5 Hz, 2H), 3.55 (d, J=13.5 Hz, 1H), 3.41 (d, J=13.5 Hz, 1H), 2.91 (s, 3H), 1.70 (s, 3H), 1.55-1.48 (m, 2H), 1.40 (s, 9H), 1.12 (d, J=6.1 Hz, 3H), 0.96-0.89 (m, 5H), 0.71-0.62 (s, 2H), LCMS [M+H]$^+$=595.

Step C: Boc Deprotection

To a solution of oxadiazole from Step B (0.048 g, 0.081 mmol) in 1 mL CH$_2$Cl$_2$ was added TFA (0.126 mL, 1.291 mmol). After 3 h, the reaction was quenched by the addition of satd. aqueous NaHCO$_3$, and diluted with EtOAc. The layers were separated, the aqueous layer washed with fresh EtOAc (2×), the combined organics were washed with brine, dried over Na$_2$SO$_4$, filtered and concentrated. The residue was purified by preparative HPLC (5->95% CH$_3$CN/H$_2$O, 0.1% added TFA, C18 PRO YMC 20×150 mm), and the fractions containing the desired product were freeze dried to obtain N-{3-{5-[(1R)-1-amino-1-methyl-2-phenylethyl]-1,3,4-oxadiazol-2-yl}-5-[(Z)-2-(2-methyl cyclopropyl)vinyl]phenyl}-N-propylmethanesulfonamide as a flocculent white solid. $^1$H NMR (CDCl$_3$) δ 7.97 (d, J=4.2 Hz, 1H), 7.82 (s, 1H), 7.71 (s, 1H), 7.31-7.30 (m, 3H), 7.08-7.07 (m, 2H), 6.38 (d, J=11.4 Hz, 1H), 5.22 (app. t, J=10.6 Hz, 1H), 3.68 (t, J=7.0 Hz, 2H), 3.43 (s, 2H), 2.96 (s, 3H), 1.86 (s, 3H), 1.54-1.45 (m, 3H), 1.11 (d, J=5.9 Hz, 3H), 0.96-0.89 (m, 4H), 0.73-0.71 (m, 1H), 0.70-0.65 (m, 1H). HRMS exact mass calc for C$_{27}$H$_{35}$N$_4$O$_3$S [M+H]$^+$: 495.2425; observed: 495.2430.

Example 8

3-(5-(((2R)-2-Amino-1-phenylpropan-2-yl)-1,3,4-oxadiazol-2-yl)-5-(1-cyanocyclopentyl)-N—((R)-1-(4-fluorophenyl)ethyl)benzamide

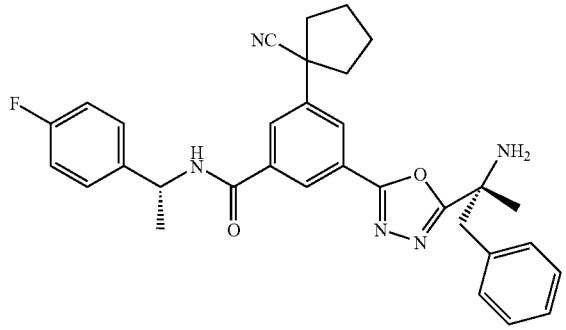

Step A: Amide Bond Formation

A solution of 3-(5-((2R)-2-tert-butoxycarbonylamino-1-phenylpropan-2-yl)-1,3,4-oxadiazol-2-yl)-5-(1-cyanocyclopentyl)benzoic acid (20 mg, 0.039 mmol), (R)-1-(4-fluorophenyl)ethanamine (0.017 mL, 0.13 mmol), benzotriazol-1-yloxy-tris(dimethylamino)-phosphonium hexafluorophosphate (24 mg, 0.05 mmol) and diisopropylethylamine (0.024 mL, 0.14 mmol) in 0.4 mL DMF was stirred at rt overnight. Purification by reverse phase preparative HPLC (5-95% MeCN/H$_2$O containing 0.1% TFA, C18 PRO YMC 20×150 mm) gave 3-(5-((R)-2-tert-butoxycarbonylamino-1-phenylpropan-2-yl)-1,3,4-oxadiazol-2-yl)-5-(1-cyanocyclopentyl)-N—((R)-1-(4-fluorophenyl)ethyl)benzamide. $^1$H NMR (400 MHz, CDCl$_3$) δ 8.30 (s, 1H), 8.16 (m, 1H), 8.10 (d, J=1.5 Hz, 1H), 7.39 (m, 2H), 7.28 (m, 3H), 7.06 (m, 4H), 6.56 (d, J=7.5 Hz, 1H), 5.33 (m, 1H), 5.07 (bs, 1H), 3.59 (d, J=13.6 Hz, 1H), 3.40 (d, J=13.6 Hz, 1H), 2.55 (m, 2H), 2.16-1.98 (m, 6H), 1.72 (s, 3H), 1.64 (d, J=7.0 Hz, 3H), 1.41 (s, 9H).

Step B: Boc Removal

A solution of 3-(5-((R)-2-tert-butoxycarbonylamino-1-phenylpropan-2-yl)-1,3,4-oxadiazol-2-yl)-5-(1-cyanocyclopentyl)-N—((R)-1-(4-fluorophenyl)ethyl)benzamide (16.2 mg, 0.025 mmol) in 0.5 mL TFA and 0.2 mL CH$_2$Cl$_2$ was stirred at rt for 1 h. Concentration and lyophilization gave 3-(5-(2-amino-1-phenylpropan-2-yl)-1,3,4-oxadiazol-2-yl)-5-(1-cyanocyclopentyl)-N—((R)-1-(4-fluorophenyl)ethyl)benzamide as the TFA salt. $^1$H NMR (400 MHz, CD$_3$OD) δ 9.13 (d, J=7.4 Hz, 1H), 8.42 (m, 1H), 8.26 (m, 1H), 8.21 (m, 1H), 7.44 (m, 2H), 7.31 (m, 3H), 7.08 (m, 4H), 5.28 (m, 1H), 3.46 (s, 2H), 2.56 (m, 2H), 2.22 (m, 2H), 2.06 (m, 4H), 1.89 (s, 3H), 1.60 (d, J=7.0 Hz, 3H).

Example 9

5-[5-((R)-1-amino-1-methyl-2-phenylethyl)-1,3,4-oxadiazol-2-yl]-2'-cyano-N-[1-(4-fluorophenyl)ethyl]biphenyl-3-carboxamide trifluoroacetate salt

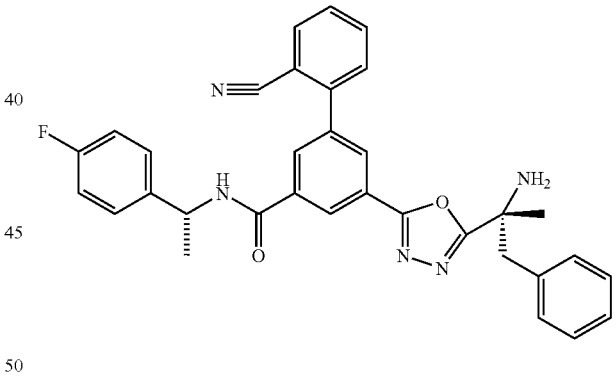

To a solution of the 5-[5-((R)-1-amino-1-methyl-2-phenylethyl)-1,3,4-oxadiazol-2-yl]-2'-cyanobiphenyl-3-carboxylic acid (Intermediate XVIII) (20 mg, 0.05 mmole) and (R)-4-fluoro alpha methyl benzyl amine (36 mg, 0.19 mmole) was added in one portion BOP reagent (25 mg, 0.06 mmole). The reaction was aged at rt for 1 hr and then purified directly by prep HPLC reverse phase chromatography. The pure fractions were collected and diluted by two fold with water and then lyophilized overnight to give the product as a fluffy white solid. $^1$H NMR (400 MHz, CD$_3$OD) δ 9.12 (d, J=7.5 Hz, 1H), 8.57 (t, J=1.6 Hz, 1H), 8.38 (t, J=1.6 Hz, 1H), 8.31 (t, J=1.6 Hz, 1H), 7.94 (dd, J=7.8, 1 Hz, 1H), 7.85 (dt, J=7.8, 1 Hz, 1H), 7.72 (dd, J=7.9, 1 Hz, 1H), 7.66 (dt, J=7.6, 1.1 Hz, 1H), 7.48-7.40 (m, 2H), 7.34-7.26 (m, 3H), 7.15-7.02 (m, 4H), 5.29 (p, J=7.1 Hz, 1H), 3.46 (s, 2H), 1.89 (s, 3H), 1.59 (d, J=7.1 Hz, 3H). LCMS [(M)+H]$^+$=546.

Example 10

N-[(1R)-1-(4-fluorophenyl)ethyl]-3-[4-(1-hydroxy-1-methyl-2-phenylethyl)-1H-1,2,3-triazol-1-yl]-5-[(methylsulfonyl)(propyl)amino]benzamide

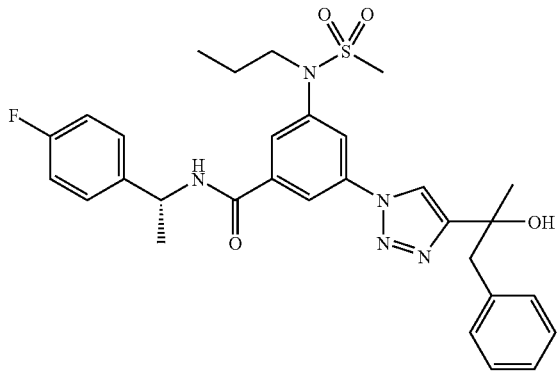

To a 0° C. suspension of 1.07 g (2.5 mmol) tribenzyl tin chloride in 30 mL ether was added 7 mL (10 mmol, 1.5M solution in pentane) methyllithium and the heterogeneous mixture was warmed to rt and stirred 3 hrs giving an approximately 0.2M solution of benzyllithium in ether.

To a solution of 0.013 g (0.027 mmol) 3-(4-acetyl-1H-1,2,3-triazol-1-yl)-N-[(1R)-1-(4-fluorophenyl)ethyl]-5-[(methylsulfonyl)(propyl)amino]benzamide in 1 mL THF at 0° C. was added 0.3 mL (approx. 0.06 mmol) benzyllithium in ether. After 30 min, another 0.3 mL benzyllithium was added and after a further 30 min the reaction mixture was quenched with 10 mL saturated NH$_4$Cl, extracted w. 20 mL EtOAc, washed with 10 mL brine, dried over MgSO$_4$, filtered, and concentrated. Purification by preparative HPLC (5->95% CH$_3$CN/H$_2$O over 30 min, 0.1% added TFA, C18 PRO YMC 20×150 nm) afforded 2 mg N-[(1R)-1-(4-fluorophenyl)ethyl]-3-[4-(1-hydroxy-1-methyl-2-phenylethyl)-1H-1,2,3-triazol-1-yl]-5-[(methylsulfonyl)(propyl)amino]benzamide as a white solid. NMR $^1$H NMR (CDCl$_3$) δ 8.06 (s, 1H), 7.82 (m, 3H), 7.39 (m, 2H) 7.30 (m, 1H), 7.24 (m, 2H), 7.06 (m, 4H), 6.59 (br d, J=7.14 Hz, 1H), 5.30 (m, 1H), 3.71 (t, J=7.14 Hz, 2H), 3.34 (br d, J=13 Hz, 1H), 3.15 (m, 1H), 2.93 (s, 3H), 1.65 (m, 6H), 1.52 (m, 2H), 0.92 (t, J=7.33 Hz, 3H). High resolution mass spec (FT/ICR) calc M+H=580.2389 found 580.2400.

Example 11

3-[4-((R)-1-amino-1-methyl-2-phenylethyl)-1H-1,2,3-triazol-1-yl]-N-[(1R)-1-(4-fluorophenyl)ethyl]-5-[(methylsulfonyl)(propyl)amino]benzamide

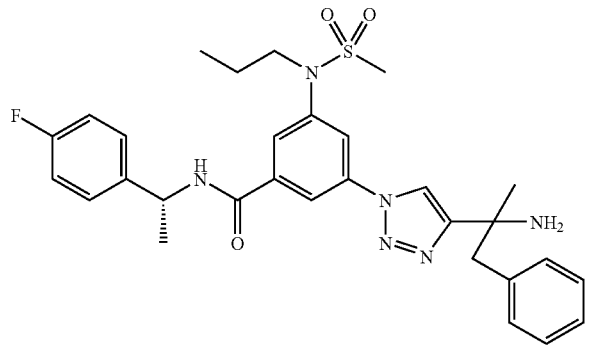

Step A: Ellman Sulfinyl Imine Formation

To a solution of 0.135 g (0.28 mmol) 3-(4-acetyl-1H-1,2,3-triazol-1-yl)-N-[(1R)-1-(4-fluorophenyl)ethyl]-5-[(methylsulfonyl)(propyl)amino]benzamide in 1 mL THF was added 0.18 mL (0.83 mmol) Ti(OEt)$_4$ and 0.04 g (0.33 mmol) 2-methyl-2-propanesulfinamide. The mixture was stirred at rt for 1 hr then heated to reflux for 7 hours whereupon 40 mg more racemic 2-methyl-2-propanesulfinamide and 0.15 mL Ti(OEt)$_4$ and were added and the mixture heated 2 more hr before cooling in an ice bath. To this was added 1 mL brine and 10 mL EtOAc and the mixture was stirred vigorously, breaking up clumps with a spatula. The mixture was filtered through celite and rinsed w. 50 mL EtOAc. The filtrate washed with 50 mL brine, dried over MgSO$_4$, filtered, and concentrated to give 0.07 g 3-{4-[(1E)-N-(tert-butylsulfinyl)ethanimidoyl]-1H-1,2,3-triazol-1-yl}-N-[(1R)-1-(4-fluorophenyl)ethyl]-5-[(methylsulfonyl)(propyl)amino]benzamide as a white solid. $^1$H NMR (400 MHz, CDCl$_3$) δ 8.53 (s, 1H), 8.14 (s, 1H), 7.96 (s, 1H), 7.87 (s, 1H), 7.39 (m, 2H) 7.07 (m, 2H), 6.51 (br d, J=7.33 Hz, 1H), 5.31 (quint, J=7.14 Hz, 1H), 3.74 (t, J=6.78 Hz, 2H), 2.94 (s, 3H), 2.92 (s, 3H), 1.65 (d, J=6.96 Hz, 3H), 1.54 (m, 2H), 1.33 (s, 9H), 0.93 (t, J=7.32 Hz, 3H). LCMS [M+H]$^+$=591.2

Step B: Grignard Addition/Chiral Auxiliary Removal

To a 0° C. suspension of 0.03 g (0.05 mmol) 3-{4-[(1E)-N-(tert-butylsulfinyl)ethanimidoyl]-1H-1,2,3-triazol-1-yl}-N-[(1R)-1-(4-fluorophenyl)ethyl]-5-[(methylsulfonyl)(propyl)amino]benzamide in 5 mL toluene was added 0.1 mL (0.2 mmol, 2M solution in toluene) trimethylaluminum followed by 1 mL (approx. 0.2 mmol, 0.2 mM solution in ether) benzyllithium. The reaction mixture was stirred for 1 hr, then 0.4 mL more benzyllithium was added and the reaction mixture stirred for another hour at 0° C. The reaction was quenched by addition of 1 mL of saturated sodium sulfate solution and 50 mL EtOAc and stirred vigorously. To this was added MgSO$_4$ and the resulting mixture was filtered through celite and concentrated. Purification by flash chromatography (1×8 cm silica gel, linear gradient 30-100% EtOAc/hexanes) afforded 8 mg 3-(4-{1-[(tert-butylsulfinyl)amino]-1-methyl-2-phenylethyl}-1H-1,2,3-triazol-1-yl)-N-[(1R)-1-(4-fluorophenyl)ethyl]-5-[(methylsulfonyl)(propyl)amino]benzamide which was dissolved in 1 mL methanol. To this was added 0.7 mL 2M HCl in ether. After 30 minutes the mixture was concentrated and purified by preparative HPLC (5->95% CH$_3$CN/H$_2$O over 30 min, 0.1% added TFA, C18 PRO YMC 20×150 mm) to afford 3 mg 3-[4-(1-amino-1-methyl-2-phenylethyl)-1H-1,2,3-triazol-1-yl]-N-[(1R)-1-(4-fluorophenyl)ethyl]-5-[(methylsulfonyl)(propyl)amino]benzamide as its trifluoroacetate salt. $^1$H NMR (CD$_3$OD, 500 MHz) δ 8.55 (s, 1H), 8.28 (s, 1H), 8.04 (s, 1H), 7.99 (m, 1H), 7.42 (m, 2H), 7.26 (m, 3H), 7.07 (m, 2H), 7.00 (m, 2H), 5.25 (m, 1H), 3.77 (t, J=6.83 Hz, 2H), 3.47 (d, J=13 Hz, 1H), 3.27 (d, J=13 Hz, 1H), 3.01 (s, 3H), 1.76 (s, 3H), 1.59 (d, J=7.18 Hz, 3H), 1.53 (m, 2H), 0.95 (t, J=7.33 Hz, 3H). High resolution mass spec (FT/ICR) calc M+H=579.2548 found 578.2560.

Example 12

N-{3-[5-((R)-1-amino-1-methyl-2-phenylethyl)-1,3,4-oxadiazol-2-yl]-5-benzoylphenyl}-N-methyl-N-methanesulfonamide

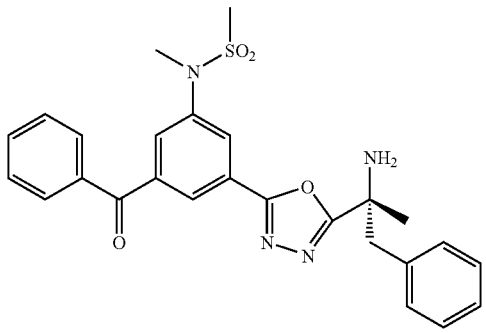

To a solution of tert-butyl[1-(5-{3-{[methoxy(methyl)amino]carbonyl}-5-[methyl (methylsulfonyl)amino]phenyl}-1,3,4-oxadiazol-2-yl)-(1R)-1-methyl-2-phenylethyl] carbamate (Intermediate XXIII) (0.022 g, 0.038 mmol) in 0.80 mL THF at 0° C. was added a 1.0M solution of PhMgBr in THF (0.15 mL, 0.153 mmol). After 1.5 h, a further aliquot of Grignard reagent (0.15 mL, 0.153 mmol) was added. After 45 min at 0° C., the reaction was warmed to rt for 15 min. Concentrated reaction, redissolved residue in 080 mL $CH_2Cl_2$ and added 0.15 mL TFA. After 15 h, a further 0.15 mL TFA was added. Another 0.15 mL aliquot of TFA was added after 4 h. Concentrated 1.5 h after last TFA aliquot addition, redissolved residue in 0.80 mL DMF and purified by preparative HPLC (5->95% $CH_3CN/H_2O$, 0.1% added TFA, C18 PRO YMC 20×150 mm), and the fractions containing the desired product were freeze dried to obtain N-{3-[5-((R)-1-amino-1-methyl-2-phenylethyl)-1,3,4-oxadiazol-2-yl]-5-benzoylphenyl}-N-methyl-N-methane sulfonamide as a flocculent white solid. $^1H$ NMR ($d_4$-MeOH, 400 MHz) 8.28 (m, 1H), 8.22 (m, 1H), 8.04 (m, 1H), 7.86-7.83 (m, 2H), 7.69 (m, 1H), 7.59-7.57 (m, 2H), 7.31-7.28 (m, 3H), 7.09-7.07 (m, 2H), 3.42 (s, 3H), 2.99 (s, 3H), 1.86 (s, 3H). HRMS exact mass calc for $C_{26}H_{27}N_4O_4S$ [M+H]$^+$: 491.1757; observed: 491.1748.

Example 13

N-{3-[5-((R)-1-amino-1-methyl-2-phenylethyl)-1,3,4-oxadiazol-2-yl]-5-acetylphenyl}-N-methyl-N-methanesulfonamide

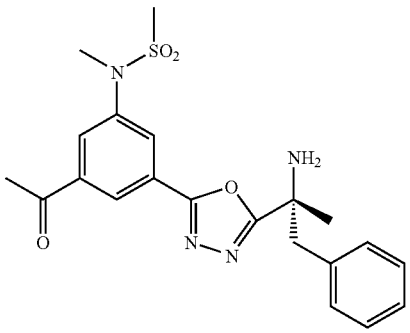

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{21}H_{25}N_4O_4S$ [M+H]$^+$: 429.1591; observed: 429.1585.

Example 14

N-{3-[5-((R)-1-amino-1-methyl-2-phenylethyl)-1,3,4-oxadiazol-2-yl]-5-propionylphenyl}-N-methyl-N-methanesulfonamide

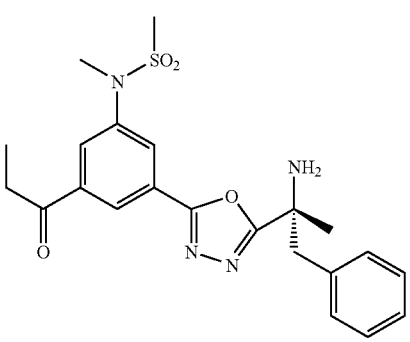

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{22}H_{27}N_4O_4S$ [M+H]$^+$: 443.1748; observed: 443.1750.

Example 15

N-{3-[5-((R)-1-amino-1-methyl-2-phenylethyl)-1,3,4-oxadiazol-2-yl]-5-isobutyrylphenyl}-N-methanesulfonamide

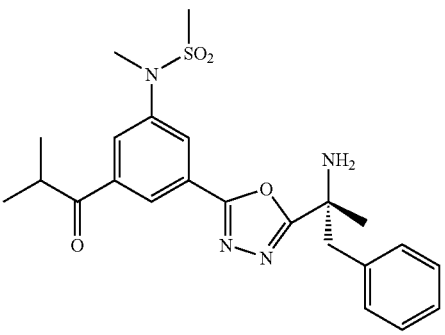

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{23}H_{29}N_4O_4S$ [M+H]$^+$: 457.1904; observed: 457.1909.

Example 16

N-{3-[5-((R)-1-amino-1-methyl-2-phenylethyl)-1,3,4-oxadiazol-2-yl]-5-(2,2-dimethylpropinoyl)phenyl}-N-methanesulfonamide

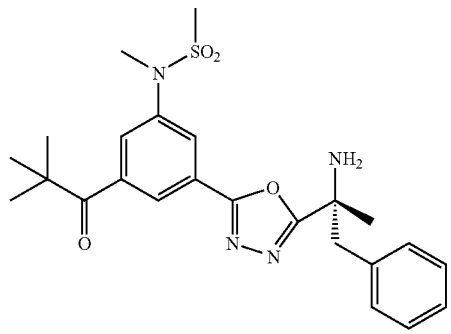

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{24}H_{31}N_4O_4S$ [M+H]$^+$: 471.2061; observed: 471.2054.

Example 17

N-[3-[5-((R)-1-amino-1-methyl-2-phenylethyl)-1,3,4-oxadiazol-2-yl]-5-(cyclopentylcarbonyl)phenyl]-N-methylmethanesulfonamide

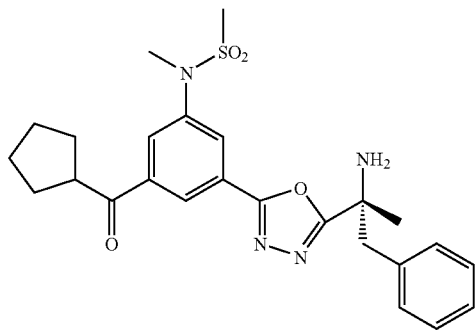

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{25}H_{31}N_4O_4S$ [M+H]$^+$: 483.2061; observed: 483.2067.

Example 18

N-[3-[5-((R)-1-amino-1-methyl-2-phenylethyl)-1,3,4-oxadiazol-2-yl]-5-(cyclohexylcarbonyl)phenyl]-N-methylmethanesulfonamide

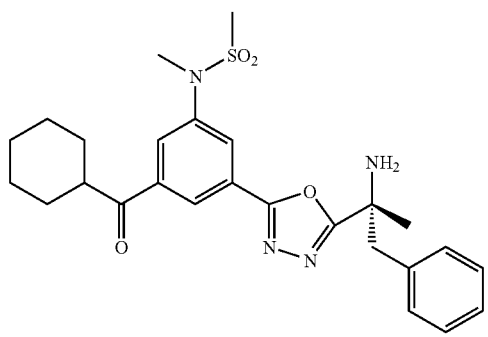

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{26}H_{33}N_4O_4S$ [M+H]$^+$: 497.2219; observed: 497.2221.

Example 19

N-[3-[5-((R)-1-amino-1-methyl-2-phenylethyl)-1,3,4-oxadiazol-2-yl]-5-(cyclopropylcarbonyl)phenyl]-N-methylmethanesulfonamide

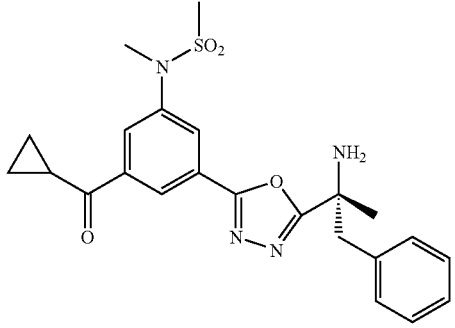

Prepared following a procedure as described to obtain N-{3-[5-((R)-1-amino-1-methyl-2-phenylethyl)-1,3,4-oxadiazol-2-yl]-5-benzoylphenyl}-N-methyl-N-methanesulfonamide (Example 12). HRMS exact mass calc for $C_{23}H_{27}N_4O_4S$ [M+H]$^+$: 465.1960; observed: 465.1932.

Example 20

3-(5-{(R)-1-amino-1-methyl-2-phenylethyl}-1,3,4-oxadiazol-2-yl)-5-[methyl(methylsulfonyl)amino]benzoic acid methyl ester

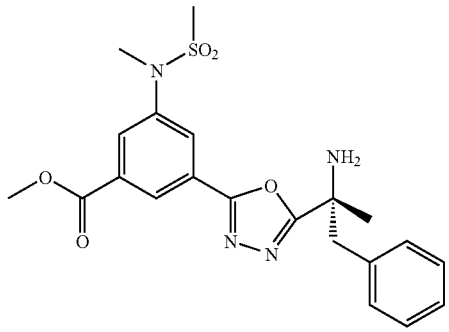

To a solution of Intermediate IV (0.021 g, 0.039 mmol) in 2 mL $CH_2Cl_2$ was added TFA (0.075 mL, 0.771 mmol). After 15 h, a further aliquot (0.075 mL, 0.771 mmol) of TFA was added. After 4 h, the reaction was concentrated and freeze dried to obtain 3-(5-{(R)-1-amino-1-methyl-2-phenylethyl}-1,3,4-oxadiazol-2-yl)-5-[methyl(methylsulfonyl)amino]benzoic acid methyl ester as a flocculent white solid. 1H NMR ($CDCl_3$, 400 MHz) δ 8.48 (m, 1H), 8.28 (m, 1H), 8.26 (m, 1H), 7.33-7.31 (m, 3H), 7.10-7.08 (m, 2H), 3.97 (s, 3H), 3.71 (s, 2H), 3.41 (s, 3H), 2.97 (s, 3H), 1.87 (s, 3H), 1.41 (s, 9H). HRMS exact mass calc for $C_{21}H_{24}N_4O_5S$ $[M+H]^+$: 445.1536; observed: 445.1540.

Example 21

N-[3-[5-((R)-1-amino-1-methyl-2-phenylethyl)-1,3,4-oxadiazol-2-yl]-5-(3-methyl-1,2,4-oxadiazol-5-yl)phenyl]methylmethanesulfonamide

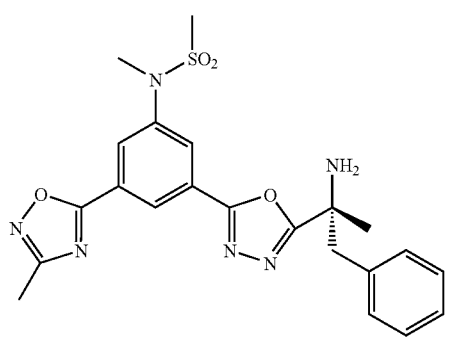

Synthesized following the procedure described for Example 5 using Intermediate V and (1)-N-hydroxyethanimidamide. Removal of the Boc group offered N-[3-[5-((R)-1-amino-1-methyl-2-phenylethyl)-1,3,4-oxadiazol-2-yl]-5-(3-methyl-1,2,4-oxadiazol-5-yl)phenyl]methylmethanesulfonamide. HRMS exact mass calc for $C_{22}H_{24}N_6O_4S$ $[M+H]^+$: 469.1640; observed: 469.1653.

Example 22

N-{3-[5-((R)-1-amino-1-methyl-2-phenylethyl)-1,3,4-oxadiazol-2-yl]-5-[2-(2-methylcyclopropyl)ethyl]phenyl}-N-propylmethanesulfonamide

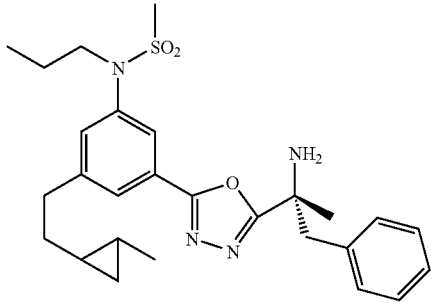

To a soln of Example 7 (0.006 g, 0.010 mmol) 1 mL EtOH was added a spatula tip of palladium on carbon. The flask was evacuated and opened to a hydrogen balloon (3×), and the reaction was allowed to proceed at rt for 2 h. The reaction was evacuated and opened to an argon source (3×), filtered through a pad of celite, rinsing with fresh EtOAc. The organics were concentrated and purified by preparative HPLC (5->95% $CH_3CN/H_2O$, 0.1% added TFA, C18 PRO YMC 20×150 mm), and the fractions containing the desired product were freeze dried to obtain N-{3-[5-((R)-1-amino-1-methyl-2-phenylethyl)-1,3,4-oxadiazol-2-yl]-5-[2-(2-methylcyclopropyl)ethyl]phenyl}-N-propyl methanesulfonamide. The desired product was obtained as a white foam. $^1$H NMR ($CDCl_3$) δ 7.80 (s, 1H), 7.78 (s, 1H), 7.54 (s, 1H), 7.32-7.30 (m, 3H), 7.09-7.06 (m, 2H), 3.70 (t, J=7.0 Hz, 2H), 2.84 (s, 3H), 2.83-2.80 (m, 2H), 1.86 (s, 3H), 1.62-1.44 (m, 6H), 0.42-0.36 (m, 2H), 0.23-0.12 (m, 2H). HRMS exact mass calc for $C_{27}H_{36}N_4O_3S$ $[M+H]^+$: 497.2575; observed: 497.2581.

Example 23

N-{3-{5-[(R)-1-amino-1-methyl-2-phenylethyl]-1H-1,2,4-triazol-3-yl]-5-[(Z)-2-(2-methylcyclopropyl)vinyl]phenyl}-N-propylmethanesulfonamide

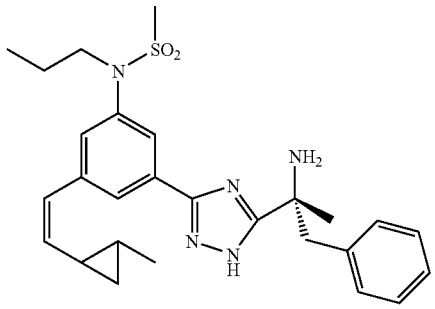

Prepared from Intermediate II and Intermediate XX as described for Example 6. HRMS exact mass calc for $C_{27}H_{36}N_4O_3S$ $[M+H]^+$: 494.2584; observed: 494.2599.

Example 24

3-[5-(2-benzylpyrrolidin-2-yl)-1,3,4-oxadiazol-2-yl]-N-[(1R)-1-(4-fluorophenyl)ethyl]-5-[methyl(methylsulfonyl)amino]benzamide

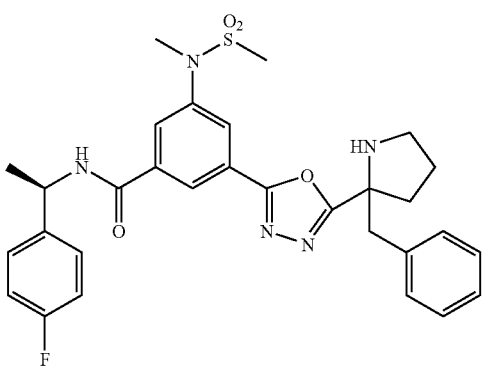

This compound was prepared from Intermediate VII and Intermediate XXVI in a similar manner to Example 7, with $Ph_3P/Im/CBr_4$ being utilized for the dehydrative cyclization in Step B. HRMS exact mass calc for $C_{30}H_{32}FN_5O_4S$ $[M+H]^+$: 578.2233; observed: 578.2232.

Example 25

N-[(1R)-1-(4-fluorophenyl)ethyl]-3-[5-(1-hydroxy-1-methyl-2-phenylethyl)-1,3,4-oxadiazol-2-yl]-5-[methyl(methylsulfonyl)amino]benzamide

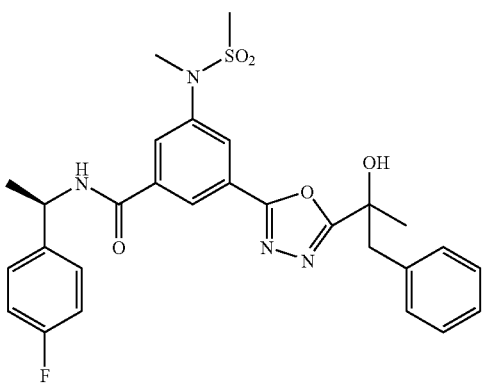

Step A: Coupling

To a solution of Intermediate III (0.221 g, 0.732 mmol) and benzyl lactic acid (0.132 g, 0.732 mmol, prepared according to the procedure reported by Sirinivasan et al, *Synth. Commun*, 1996, 2161-2164) in 3 mL DMF was added EDC (0.183 g, 0.952 mmol) and HOAT (0.023 g, 0.146 mmol). After 50 h, the reaction was quenched by the addition of 3M LiCl and diluted with EtOAc. The layers were separated and the aqueous washed with EtOAc (2×). The combined organics were washed with 3M LiCl and brine, dried over Na2SO4, filtered and concentrated. The residue was purified by silica gel chromatography (0->8% MeOH/CH2Cl2) to afford the desired adduct as a viscous oil. $^1$H NMR ($d_4$-MeOH, 400 MHz) 8.43 (m, 1H), 8.22 (m, 1H), 8.13 (m, 1H), 7.29-7.17 (m, 5H), 3.93 (s, 3H), 3.37 (s, 3H), 3.12 (d, J=13.6 Hz, 1H), 2.91 (d, J=13.6 Hz, 1H), 2.94 (s, 3H), 1.41 (s, 3H). LCMS $[M+H]^+$=464.

Step B: TES Protection

To a solution of alcohol from Step A (0.062 g, 0.134 mmol) and 2,6-lutidine (0.070 mL, 0.602 mmol) in 1.5 mL $CH_2Cl_2$ was added triethylsilyl trifluoromethanesulfonate (0.120 mL, 0.535 mmol). The reaction was allowed to warm to rt over 3H, then quenched by the addition of satd. NaHCO3 and diluted with EtOAc. The layers were separated, the aqueous washed with EtOAc (2×), and the combined organics were washed with brine and dried over $Na_2SO_4$, filtered and concentrated. Purification by silica gel chromatography afforded the desired product as a white foam. $^1$H NMR ($CDCl_3$, 400 MHz) 9.46 (br s, 1H), 9.04 (br s, 1H), 8.27 (m, 1H), 8.15 (m, 1H), 8.01 (m, 1H), 7.23-7.13 (m, 5H), 3.89 (s, 3H), 3.31 (s, 3H), 3.10 (d, J=13.6 Hz, 1H), 2.84 (d, J=13.6 Hz, 1H), 2.94 (s, 3H), 1.59 (s, 3H), 0.90 (t, J=6.4 Hz, 9H), 0.67-0.59 (m, 6H); LCMS $[M+H]^+$=578.

Step C: Dehydration

To a solution of product from Step B (0.067 g, 0.116 mmol) in 1 mL 1,2-dichloroethane was added Burgess reagent (0.083 g, 0.348 mmol). The slurry was microwaved at 120° C. for 8 min, and the reaction was loaded directly onto a silica gel column for purification (5->45% EA/hex) to afford the desired product was a white foam. $^1$H NMR ($CDCl_3$, 400 MHz) 8.51 (m, 1H), 8.20 (m, 1H), 8.16 (m, 1H), 7.24-7.19 (m, 3H), 7.12-7.10 (m, 2H), 3.96 (s, 3H), 3.38 (s, 3H), 3.23 (d, J=13.4 Hz, 1H), 3.15 (d, J=13.4 Hz, 1H), 2.90 (s, 3H), 1.74 (s, 3H), 0.85 (t, J=7.0 Hz, 9H), 0.55-0.43 (m, 6H); LCMS $[M+H]^+$=560.

Step D: Hydrolysis/Deprotection

To a solution of ester (0.025 g, 0.045 mol) in 1 mL THF was added 1M LiOH (0.134 mL, 0.134 mmol). After 3.5 h at rt, the reaction was quenched by the addition of 0.20 mL 1N HCl. After 1.5 h, 0.050 mL 6N HCl was added. After a further 1.5 h, the reaction was quenched by the addition of satd. NaHCO3 and diluted with EtOAc. The layers were separated, and the aqueous washed with EtOAc (3×). The combined organics were dried over $Na_2SO_4$, filtered and concentrated. The resulting white foam was used without further purification. LCMS $[M+H]^+$=432.

Step E: Amide Bond Formation

To a soln of (1R)-1-(4-fluorophenyl)ethanamine (0.010 mL, 0.076 mmol) and unpurified acid (0.022 g, 0.051 mmol) from Step D in 0.80 mL DMF was added EDC (0.015 g, 0.076 mmol) and HOAt (0.002 g, 0.015 mmol). After 18 h, the reaction was directly purified by preparative HPLC (5->95% $CH_3CN/H_2O$, 0.1% added TFA, C18 PRO YMC 20×150 mm), and the fractions containing the desired product were freeze dried to obtain N-[(1R)-1-(4-fluorophenyl)ethyl]-3-[5-(1-hydroxy-1-methyl-2-phenylethyl)-1,3,4-oxadiazol-2-yl]-5-[methyl(methylsulfonyl)amino]benzamide as a flocculent white solid. $^1$H NMR ($CDCl_3$) δ 8.26 (m, 1H), 8.11 (m, 1H), 7.95 (m, 1H), 7.36 (dd, J=8.6, 5.3 Hz, 2H), 7.24 (m, 3H), 7.09-7.00 (m, 4H), 6.43 (d, J=8.1 Hz, 1H), 5.30 (m, 1H), 3.38 (s, 3H), 3.33 (d, J=13.5 Hz, 1H), 3.18 (d, J=13.4 Hz, 1H), 2.89 (s, 3H), 1.75 (s, 3H), 1.62 (d, J=7.0 Hz, 3H). HRMS exact mass calc for $C_{28}H_{29}FN_4O_5S$ $[M+H]^+$: 553.1916; observed: 553.1916.

Example 26

3-[5-((R)-1-amino-1-methyl-2-phenylethyl)-1,3-oxazol-2-yl]-N-[(1)-1-(4-fluorophenyl)ethyl]-5-[methyl(methylsulfonyl)amino]benzamide

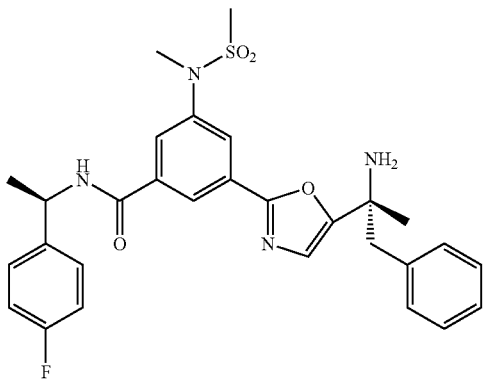

Step A: Amide Bond Formation

To a solution of acid (Intermediate III) (0.295 g, 1.03 mmol) and amine (Intermediate XXXVII) (0.275 g, 0.934 mmol) in 10 mL of DMF was added EDC (0.220 g, 1.15 mmol) and HOAt (0.140 g, 1.03 mmol). The reaction was stirred at rt for 50 h, then diluted with EtOAc. The organic layer washed with $H_2O$, 10% $KHSO_4$, sat. $NaHCO_3$ and 3M LiCl. Drying and solvent evaporation gave A as a thick oil. Used as is in next step. LCMS $[M+H]^+$=564.

Step B: Oxidation

To a solution of A (0.680 g, 1.21 mmol) in 10 mL of $CH_2Cl_2$ was added $Et_3N$ (0.366 g, 3.62 mmol) and sulfur trioxide pyridine (0.480 g, 3.02 mmol) in 2.5 mL of DMSO. After stirring at rt for 3.5 h, the reaction was diluted with EtOAc. The organic layer washed with 10% $KHSO_4$, sat. $NaHCO_3$ and 3M LiCl, dried over $Na_2SO_4$, filtered and concentrated. The residue was purified by normal phase chromatography (5->40% EtOAc/hexanes) to obtain the desired ketone B as a white solid. $^1H$ NMR ($CDCl_3$) δ 8.36 (s, 1M), 8.21 (s, 1H), 8.08 (s, 1H), 7.35-7.29 (m, 3H), 7.13 (d, J=7.2 Hz, 2H), 7.01 (s, 1H), 4.75-4.47 (m, 3H), 3.97 (s, 3H), 3.39-3.34 (m, 4H), 3.08 (d, J=13.7 Hz, 1H), 2.89 (s, 3H), 1.49 (s, 9H) 1.33 (s, 3H). LCMS $[M+H]^+$=562.

Step C: Dehydration

To a solution of B (0.170 g, 0.303 mmol) in 3.5 mL of 1,2-dichloroethane was added Burgess reagent (0.289 g, 1.21 mmol). The solution was microwaved at 80° C. for 15 min. The reaction mixture was loaded directly onto a silica gel column and purified by normal phase chromatography (10->35% EtOAc/hexanes) to obtain the desired oxazole C as a solid. $^1H$ NMR ($CDCl_3$) δ 8.55 (m, 1H), 8.22 (m, 1H), 8.12 (m, 1H), 7.29-7.27 (m, 3H), 7.07-7.04 (m, 2H), 6.95 (s, 1H), 4.80 (s, 1H), 3.98 (s, 3H), 3.41 (s, 3H), 3.16-3.13 (m, 2H), 2.92 (s, 3H), 1.49 (s, 9H) 1.26 (s, 3H). LCMS $[M+H]^+$=544.

Step D: Hydrolysis

To a solution of C (0.059 g, 0.109 mmol) in 0.7 mL of THF was added 1N LiOH (0.27 mL, 0.27 mmol). After 1.5 hr at rt, the reaction was quenched by addition of 1N HCl (0.30 mL, 0.30 mmol) and diluted with EtOAc and $H_2O$. The layers were separated, and the aqueous layer was extracted with EtOAc (3x). The combined organics were dried over $Na_2SO_4$, filtered and concentrated to give the desired acid D as oil. The acid was used without further purification. $^1H$ NMR ($CDCl_3$) δ 8.73 (s, 1H), 8.25 (m, 1H), 8.16 (m, 1H), 7.31-7.26 (m, 3H), 7.08-7.06 (m, 3H), 3.45-3.40 (m, 4H), 3.17 (d, J=13.2 Hz, 1H), 2.94 (s, 3H), 1.62 (s, 3H) 1.26 (s, 9H). LCMS $[M+H]^+$=530.

Step E: Amide Formation

To a solution of acid D (0.020 g, 0.038 mmol) in 0.2 mL of DMF was added (R)-1-(4-fluorophenyl)ethylamine (0.005 g, 0.038 mmol), EDC (0.009 g, 0.045 mmol) and HOAt (0.006 g, 0.042 mmol). The reaction was stirred at rt for 18 h. Purification by reverse phase preparative HPLC (5-95% MeCN/$H_2O$ containing 0.1% TFA, C18 PRO YMC 20×150 mm) gave the desired amide E. LCMS $[M+H]^+$=651.

Step F: Deprotection

A solution of amide E in 0.5 mL of $CH_2Cl_2$ and 0.5 mL of TFA was stirred at rt for 1 hr. The reaction was concentrated, and the residue was freeze dried to give 3-[5-((R)-1-amino-1-methyl-2-phenylethyl)-1,3-oxazol-2-yl]-N-[(1)-1-(4-fluorophenyl)ethyl]-5-[methyl(methylsulfonyl)amino]benzamide as a light yellow solid. $^1H$ NMR ($CDCl_3$) δ 8.32 (s, 1H), 8.08 (s, 1H), 7.98 (s, 1H), 7.40-7.36 (m, 2H), 7.30-7.19 (m, 3H), 7.06-7.01 (m, 2H), 6.89-6.88 (m, 3H), 5.26 (m, 1H), 3.48 (d, J=13.4 Hz, 1H), 3.38 (s, 3H), 3.29 (d, J=13.6 Hz, 1H), 2.99 (s, 3H), 1.65-1.63 (m, 6H). HRMS exact mass calc for $C_{29}H_{31}FN_4O_4S$ $[M+H]^+$: 551.2140; observed: 551.2123.

Example 27

N-{3-[5-((R)-1-amino-1-methyl-2-phenylethyl)-1,3-oxazol-2-yl]-5-[(Z)-2-(2-methylcyclopropyl)vinyl]phenyl}-N-propylmethanesulfonamide

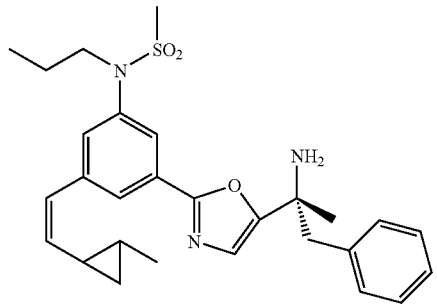

Prepared from Intermediate XV and Intermediate XXXVII using a procedure as described in steps A-C and step F in the Example 26 synthesis.

Example 28 methyl-2-{3-[5-((R)-1-amino-1-methyl-2-phenylethyl)-1,3,4-oxadiazol-2-yl]-5-[(dipropylamino)carbonyl]phenyl}-3-furoate

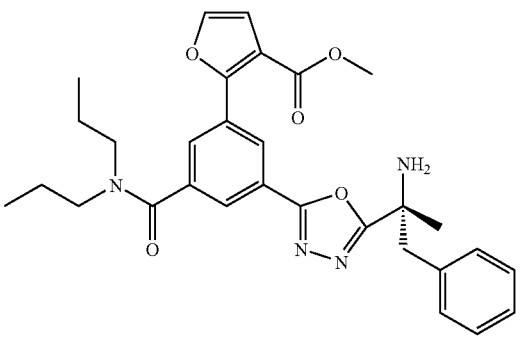

A solution of Intermediate LIV in 0.3 mL of $CH_2Cl_2$ and 0.3 mL of TFA was stirred at rt for 1 hr. The reaction was concentrated, and purified by reverse phase preparative HPLC (5-95% MeCN/$H_2O$ containing 0.1% TFA, C18 PRO YMC 20×150 mm) to give methyl2-{3-[5-((R)-1-amino-1-methyl-2-phenylethyl)-1,3,4-oxadiazol-2-yl]-5-[(dipropylamino)carbonyl]phenyl}-3-furoate as white solid. $^1$H NMR (CDCl$_3$) δ 8.80 (t, J=1.5 Hz, 1H), 8.26-8.25 (m, 1H), 8.06-8.05 (m, 1H), 7.51 (d, J=1.8 Hz, 1H), 7.27-7.20 (m, 3H), 7.03-7.00 (m, 2H), 6.90 (d, J=1.8 Hz, 1H), 3.86 (s, 3H), 3.63-3.29 (m, 6H), 1.86 (s, 3H), 1.78-1.60 (m, 4H), 1.02-0.99 (m, 3H), 0.80 (t, J=7.3 Hz, 3H). LCMS [M+H]$^+$=531

Example 29

2-{3-[5-((R)-1-amino-1-methyl-2-phenylethyl)-1,3,4-oxadiazol-2-yl]-5-[(dipropylamino)carbonyl]phenyl}-3-furoic acid

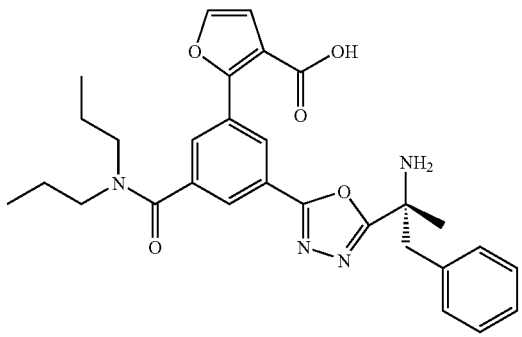

A solution of Intermediate LV in 0.3 mL of CH$_2$Cl$_2$ and 0.3 mL of TFA was stirred at rt for 1 hr. The reaction was concentrated, and the residue was freeze dried to give 2-{3-[5-((R)-1-amino-1-methyl-2-phenylethyl)-1,3,4-oxadiazol-2-yl]-5-[(dipropylamino)carbonyl]phenyl}-3-furoic acid as a white solid. $^1$H NMR (d$_4$-MeOH) δ 8.74 (t, J=1.7 Hz, 1H), 8.37-8.36 (m, 1H), 7.98 (m, 1H), 7.73 (d, J=2.0 Hz, 1H), 7.33-7.31 (m, 3H), 7.12-7.09 (m, 2H), 6.96 (d, J=1.8 Hz, 1H), 3.55-3.30 (m, 6H), 1.87 (s, 3H), 1.79-1.59 (m, 4H), 1.05-1.01 (m, 3H), 0.79-0.75 (m, 3H). HRMS exact mass calc for C$_{29}$H$_{32}$N$_4$O$_5$ [M+H]$^+$: 517.2446; observed: 517.2419.

Example 30

2-{3-[5-((R)-1-amino-1-methyl-2-phenylethyl)-1,3,4-oxadiazol-2-yl]-5-[(dipropylamino)carbonyl]phenyl}-3-furamide

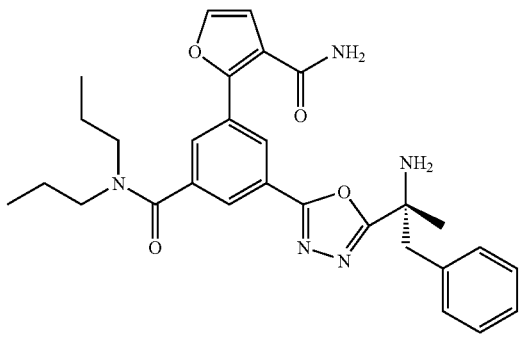

A solution of Intermediate LVI in 0.3 mL of CH$_2$Cl$_2$ and 0.3 mL of TFA was stirred at rt for 1 hr. The reaction was concentrated, and the residue was freeze dried to give the 2-{3-[5-((R)-1-amino-1-methyl-2-phenylethyl)-1,3,4-oxadiazol-2-yl]-5-[(dipropylamino)carbonyl]phenyl}-3-furamide as a white solid. $^1$H NMR (CDCl$_3$) δ 7.79-7.72 (m, 3H), 7.27-7.14 (m, 4H), 6.93-6.91 (m, 2H), 6.52 (s, 1H), 6.20 (s, 1H), 3.65-3.57 (m, 2H), 3.43 (d, J=13.7, 1H), 3.19-3.08 (m, 3H), 2.06 (s, 3H), 1.65-1.49 (m, 4H), 0.97-0.93 (t, J=7.3, 3H), 0.71-0.67 (t, J=7.3, 3H). HRMS exact mass calc for C$_{29}$H$_{33}$N$_5$O$_4$ [M+H]$^+$: 516.2606; observed: 516.2572.

Example 31

3-[5-((R)-1-amino-1-methyl-2-phenylethyl)-1,3,4-oxadiazol-2-yl]-5-(3-cyano-2-furyl)-N,N-dipropylbenzamide

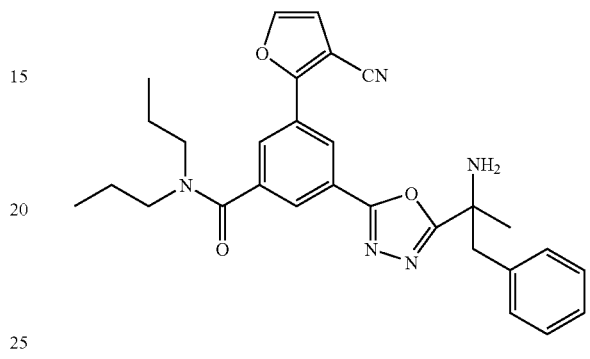

Step A: Nitrile Formation

To a solution of Intermediate LVI (0.005 g, 0.008 mmol) in 0.2 mL of 1,2-dichloroethane was added Burgess reagent (0.004 g, 0.016 mmol). The solution was microwaved at 100° C. for 5 minutes. The reaction was concentrated, and purified by reverse phase preparative HPLC (5-95% MeCN/H$_2$O containing 0.1% TFA, C18 PRO YMC 20×150 mm) to give nitrile I as white solid. LCMS [M+H]$^+$=598.

A solution of nitrile I in 0.4 mL of CH$_2$Cl$_2$ and 0.4 mL of TFA was stirred at rt for 1 hr. The reaction was concentrated, and the residue was freeze dried to give the desired product as a white solid. $^1$H NMR (CDCl$_3$) δ 8.76 (s, 1H), 8.22 (s, 1H), 8.17 (s, 1H), 7.60 (d, J=1.8 Hz, 1H), 7.28-7.21 (m, 3H), 7.04-7.0 (m, 2H), 6.78 (d, J=2.0 Hz, 1H), 3.69-3.30 (m, 6H), 1.85 (s, 3H), 1.80-1.66 (m, 4H), 1.03-0.99 (m, 3H), 0.85-0.81 (m, 3H). HRMS exact mass calc for C$_{29}$H$_{31}$N$_5$O$_3$ [M+H]$^+$: 498.2500; observed: 498.2514.

Example 32

3-[5-((R)-1-amino-1-methyl-2-phenylethyl)-1,3,4-oxadiazol-2-yl]-N,N-dipropylbenzamide

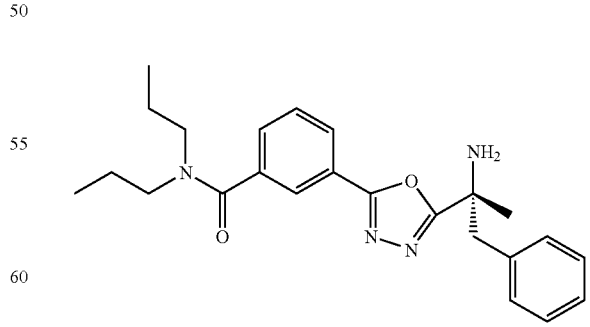

3-[5-((R)-1-(tertbutoxycarbonylamino)-1-methyl-2-phenylethyl)-1,3,4-oxadiazol-2-yl]-N,N-dipropylbenzamide was obtained as a byproduct of Step A in the synthesis of Intermediate LIV. A solution of this byproduct in 0.2 mL of CH$_2$Cl$_2$ and 0.2 mL of TFA was stirred at rt for 1 hr. The reaction was concentrated, and the residue was freeze dried to give 3-[5-((R)-1-amino-1-methyl-2-phenylethyl)-1,3,4-oxadiazol-2-yl]-N,N-dipropylbenzamide as a white solid. $^1$H NMR (CDCl$_3$) δ 8.22 (d, J=7.7 Hz, 1H), 8.05 (s, 1H), 7.58-7.47 (m, 2H), 7.26-7.22 (m, 3H), 7.01-6.99 (m, 2H), 3.63-3.23 (m, 6H), 1.83 (s, 3H), 1.77-1.57 (m, 4H), 1.00 (t, J=7.3 Hz, 3H), 0.81-0.78 (m, 3H). LCMS [M+H]$^+$=407.

Example 33 methyl2-[3-[5-((R)-1-amino-1-methyl-2-phenylethyl)-1,3,4-oxadiazol-2-yl]-5-({[(R)-1-(4-fluorophenyl)ethyl]amino}carbonyl)phenyl]-3-furoate

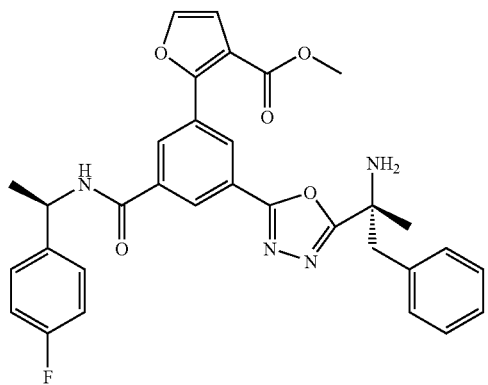

Prepared using a procedure similar to that used in the synthesis of Example 27.

Example 34

2-[3-[5-((R)-1-amino-1-methyl-2-phenylethyl)-1,3,4-oxadiazol-2-yl]-5-({[(R)-1-(4-fluorophenyl)ethyl]amino}carbonyl)phenyl]-3-furoic acid

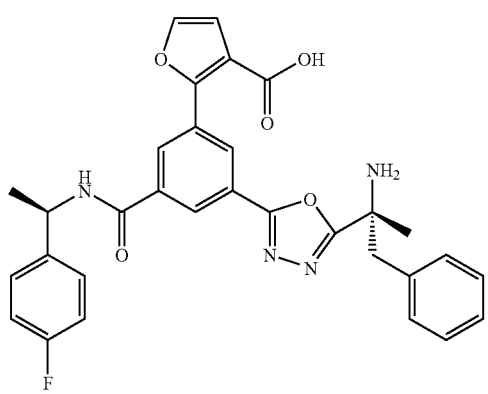

Prepared using a procedure similar to that used in the synthesis of Example 29.

Example 35

3-[5-((R)-1-amino-1-methyl-2-phenylethyl)-1,3,4-oxadiazol-2-yl]-5-(3-cyano-2-furyl)-N—[(R)-1-(4-fluorophenyl)ethyl]benzamide

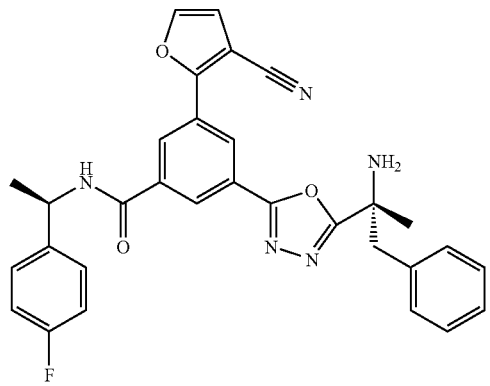

Prepared using a procedure similar to that used in the synthesis of Example 31.

Example 36

3-[5-(1-amino-1-methyl-2-phenylethyl)-1,3,4-oxadiazol-2-yl]-N—[(R)-1-(4-fluorophenyl)ethyl]benzamide

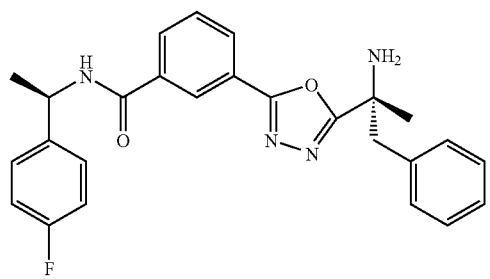

Prepared using a procedure similar to that used in the synthesis of Example 32.

Example 37

N-(3-[5-((R)-1-amino-1-methyl-2-phenylethyl)-1,3,4-oxadiazol-2-yl]-5-{[(2,2,2-trifluoro-1-phenylethyl)amino]methyl}phenyl)-N-methylmethanesulfonamide

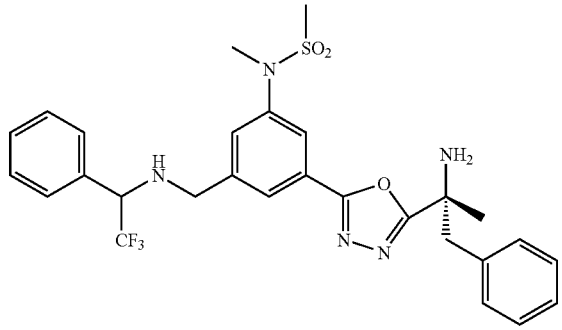

To a solution of Intermediate XXVII (0.015 g, 0.026 mmol), in 500 µL DMF was added (2,2,2-trifluoro-1-phenylethyl)amine (Prepared according to the procedure described by Watanabe et al, *Journal of Fluorine Chemistry*, 1997, 83(1), 15-19) (0.023 g, 0.129 mmol). The resulting solution was microwaved at 100° C. for 5 min. The reaction mixture was purified directly by preparative HPLC (5->95% CH$_3$CN/H$_2$O, 0.1% added TFA, C18 PRO YMC 20×150 mm) to give the desired product as a colorless oil which was taken up in 1.0 mL of 4.0M HCl in dioxane (1.0 mL, 4.00 mmol). After 3 hr, the reaction was concentrated under reduced pressure and freeze dried from dioxane/water to give N-(3-[5-((R)-1-amino-1-methyl-2-phenylethyl)-1,3,4-oxadiazol-2-yl]-5-{[(2,2,2-trifluoro-1-phenylethyl)amino]methyl}phenyl)-N-methylmethanesulfonamide. $^1$H NMR (CD$_3$OD, 400 MHz) δ 8.04 (s, 1H), 8.02 (s, 1H), 7.71 (s, 1H), 7.58-7.50 (m, 5H), 7.33-7.29 (m, 3H), 7.12-7.07 (m, 2H), 5.00-4.93 (m, 1H), 4.19 (A of AB, d, J=13.7 Hz, 1H), 4.14 (B of AB, d, J=13.7 Hz, 1H), 3.47 (s, 2H), 3.37 (s, 3H), 2.99 (s, 3H), 1.89 (s, 3H). LCMS [M+H]$^+$=574.

Example 38

3'-[5-((R)-1-amino-1-methyl-2-phenylethyl)-1,3-oxazol-2-yl]-5'-[((R)-2-prop-1-yn-1-ylpyrrolidin-1-yl)carbonyl]biphenyl-2-carbonitrile

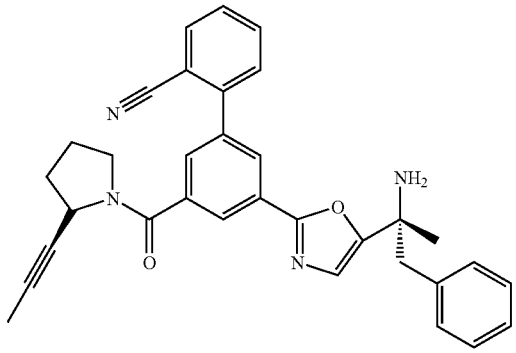

3'-[5-((R)-1-amino-1-methyl-2-phenylethyl)-1,3-oxazol-2-yl]-5'-[((R)-2-prop-1-yn-1-ylpyrrolidin-1-yl)carbonyl]biphenyl-2-carbonitrile was prepared in a similar manner to Example # 25 from Intermediate XVII, Intermediate XL and Intermediate LIII. LCMS [M+H]$^+$=515.

Example 39

3-(N-Methyl-N-(methylsulfonyl)amino)-5-(3-((R)-2-amino-1-phenylpropan-2-yl)isoxazol-5-yl)-N—((R)-1-(4-fluorophenyl)ethyl)benzamide

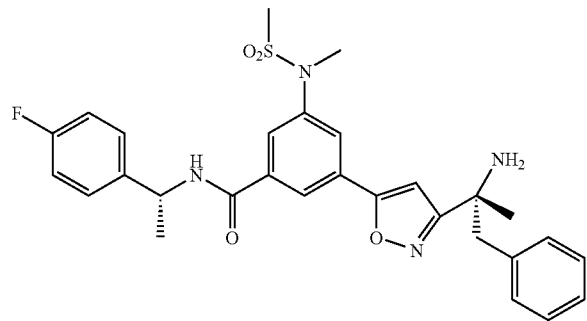

Step A: Sonagshira Coupling

To a solution of 3-(N-methyl-N-(methylsulfonyl)amino)-5-bromo-N—((R)-1-(4-fluorophenyl)ethyl)benzamide (200 mg, 0.46 mmol), copper(I)iodide (3.6 mg, 0.019 mmol), bis (tri-t-butylphosphine) palladium (0) (14 mg, 0.028 mmol) and tris(dibenzylide acetone) dipalladium (0) chloroform adduct (14.2 mg, 0.014 mmol) in 0.5 mL degassed dioxane was added diisopropylamine (0.084 mL, 0.60 mmol) and (trimethylsilyl)acetylene (0.085 mL, 0.60 mmol). The reaction was stirred at rt overnight and then heated to 60° C. for an additional night. The mixture was diluted with EtOAc and filtered through celite. Concentration and flash chromatography (10-50% EtOAc/hexanes) gave 3-(N-methyl-N-(methylsulfonyl)amino)-N—((R)-1-(4-fluorophenyl)ethyl)-5-(2-trimethylsilyl)ethynyl)benzamide. $^1$H NMR (CDCl$_3$) δ 7.77 (m, 1H), 7.67 (m, 1H), 7.61 (m, 1H), 7.35 (m, 2H), 7.05 (m, 2H), 6.28 (d, J=7.3 Hz, 1H), 5.29 (m, 1H), 3.33 (s, 3H), 2.86 (s, 3H), 1.60 (d, J=7.0 Hz, 3H), 0.26 (s, 9H).

Step B: TMS Deprotection

To a solution of 3-(N-methyl-N-(methylsulfonyl)amino)-N—((R)-1-(4-fluorophenyl)ethyl)-5-(2-trimethylsilyl)ethynyl)benzamide from Step A (132 mg, 0.30 mmol) in 0.58 mL methanol was added potassium carbonate (4.1 mg, 0.03 mmol) and the reaction was stirred at rt for 2 h. The mixture was concentrated, diluted with EtOAc and washed with water and brine. Drying, solvent evaporation and flash chromatography (15-55% EtOAc/hexanes) gave 3-(N-methyl-N-(methylsulfonyl)amino)-5-ethynyl-N—((R)-1-(4-fluorophenyl)ethyl)benzamide. $^1$H NMR (CDCl3) δ 7.80 (m, 1H), 7.71 (s, 1H), 7.63 (m, 1H), 7.35 (m, 2H), 7.05 (m, 2H), 6.32 (d, J=7.2 Hz, 1H), 5.29 (m, 1H), 3.33 (s, 3H), 3.16 (s, 1H), 2.86 (s, 3H), 1.60 (d, J=7.0 Hz, 3H).

Step C: Cycloaddition

To a solution of (R)-2-tert-butoxycarbonylamino-2-methyl-3-phenylpropanal oxime (Intermediate L, 30 mg, 0.11 mmol) in 0.5 mL DMF, cooled to 5° C., was added a solution of N-bromosuccinimide from Step B (29 mg, 0.165 mmol) in 0.5 mL DMF dropwise. After stirring at 5° C. for 1 h, a solution of 3-(N-methyl-N-(methylsulfonyl)amino)-5-ethynyl-N—((R)-1-(4-fluorophenyl)ethyl)benzamide (124 mg, 0.33 mmol) and triethylamine (0.023 mL, 0.165 mmol) in 0.2 mL DMF was added. The reaction was stirred at rt for 1 week and then heated to 50° C. overnight. Purification by reverse phase preparative HPLC (5-95% CH$_3$CN in water containing 0.1% TFA) gave 3-(N-methyl-N-(methylsulfonyl)amino)-5-(3-((R)-2-tert-butoxycarbonylamino-1-phenylpropan-2-yl)isoxazol-5-yl)-N—((R)-1-(4-fluorophenyl)ethyl)benzamide. $^1$H NMR (CDCl$_3$) δ 8.02 (s, 1H), 7.90 (m, 1H), 7.86 (m, 1H), 7.38 (m, 2H), 7.26 (m, 3H), 7.08 (m, 4H), 6.60 (s, 1H), 6.44 (d, J=7.6 Hz, 1H), 5.31 (m, 1H), 5.01 (bs, 1H), 3.53 (d, J=12.9 Hz, 1H), 3.39 (s, 3H), 3.34 (m, 1H), 2.89 (s, 3H), 1.63 (m, 6H), 1.44 (s, 9H).

Step D: Deprotection

A solution of 3-(N-methyl-N-(methylsulfonyl)amino)-5-(3-((R)-2-tert-butoxycarbonylamino-1-phenylpropan-2-yl)isoxazol-5-yl)-N—((R)-1-(4-fluorophenyl)ethyl)benzamide from Step C (4.8 mg, 0.0074 mmol) in 0.2 mL CH$_2$Cl$_2$ and 0.5 mL TFA was stirred at rt for 1 h. Concentration and lyophilization gave 3-(N-methyl-N-(methylsulfonyl)amino)-5-(3-((R)-2-amino-1-phenylpropan-2-yl)isoxazol-5-yl)-N—((R)-1-(4-fluorophenyl)ethyl)benzamide as the TFA salt. $^1$H NMR (CD$_3$OD) δ 9.00 (d, J=7.6 Hz, 1H), 8.22 (m, 1H), 8.05 (m, 1H), 8.01 (m, 1H), 7.44 (m, 2H), 7.31 (m, 3H), 7.09 (m, 4H), 7.02 (s, 1H), 5.26 (m, 1H), 3.40 (s, 3H), 3.33 (m, 2H), 2.98 (s, 3H), 1.78 (s, 3H), 1.59 (d, J=7.0 Hz, 3H).

Example 40

3-(5-((R)-2-Amino-1-phenylpropan-2-yl)-1,3,4-oxadiazol-2-yl)-5-(cyclobutoxymethyl)-N-methyl-N-(methylsulfonyl)benzenamine

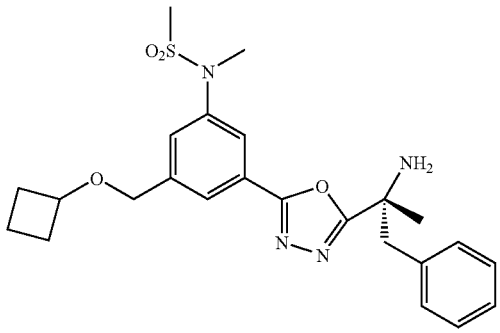

Step A: Etherification

To a solution of cyclobutanol (0.009 mL, 0.115 mmol) in 0.26 mL DMF, cooled to 0° C., was added sodium bis(trimethylsilyl)amide dropwise. After stirring for 5 min, a solution of 3-(5-((R)-2-tert-butoxycarbonylamino-1-phenylpropan-2-yl)-1,3,4-oxadiazol-2-yl)-5-(bromomethyl)-N-methyl-N-(methylsulfonyl)benzenamine (13.5 mg, 0.023 mmol) in 0.25 mL DMF was added and the reaction was stirred at 0° C. for 1 h. The reaction mixture was diluted with water, extracted with EtOAc and washed with brine. Drying, solvent evaporation and flash chromatography (15-55% EtOAc/hexanes) gave 3-(5-((R)-2-tert-butoxycarbonylamino-1-phenylpropan-2-yl)-1,3,4-oxadiazol-2-yl)-5-(cyclobutoxymethyl)-N-methyl-N-(methylsulfonyl)benzenamine. $^1$H NMR (CDCl3) δ 7.90 (d, J=9.0 Hz, 2H), 7.58 (s, 1H), 7.27 (m, 3H), 7.06 (m, 2H), 5.09 (bs, 1H), 4.47 (s, 2H), 4.05 (m, 1H), 3.57 (d, J=13.6 Hz, 1H), 3.43 (m, 1H), 3.38 (s, 3H), 2.90 (s, 3H), 2.24 (m, 2H), 2.02 (m, 2H), 1.73 (s, 3H), 1.56 (m, 2H), 1.42 (s, 9H).

Step B: Deprotection

A solution of 3-(5-((R)-2-tert-butoxycarbonylamino-1-phenylpropan-2-yl)-1,3,4-oxadiazol-2-yl)-5-(cyclobutoxymethyl)-N-methyl-N-(methylsulfonyl)benzenamine (6.0 mg, 0.010 mmol) in 0.25 mL CH$_2$Cl$_2$ and 0.75 mL TFA was stirred at rt for 1 h. Concentration and lyophilization gave 3-(5-((R)-2-amino-1-phenylpropan-2-yl)-1,3,4-oxadiazol-2-yl)-5-(cyclobutoxymethyl)-N-methyl-N-(methylsulfonyl)benzenamine as the TFA salt. $^1$H NMR (CD$_3$OD) δ 7.94 (m, 2H), 7.68 (s, 1H), 7.33 (m, 3H), 7.09 (m, 2H), 4.53 (s, 2H), 4.10 (m, 1H), 3.45 (s, 2H), 3.38 (s, 3H), 2.96 (s, 3H), 2.23 (m, 2H), 2.00 (m, 2H), 1.88 (s, 3H), 1.74 (m, 1H), 1.57 (m, 1H).

Example 41

3-(5-((R)-2-Amino-1-phenylpropan-2-yl)-1,3,4-oxadiazol-2-yl)-5-((cyclopentyloxy)methyl)-N-methyl-N-(methylsulfonyl)benzenamine

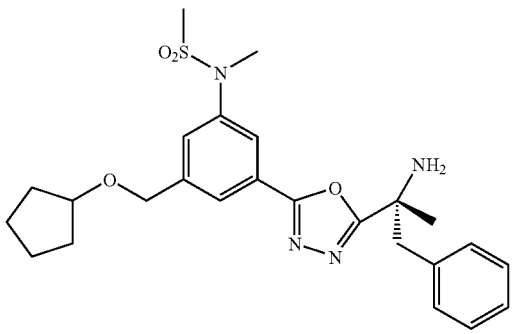

Prepared from cyclopentanol and 3-(5-((R)-2-tert-butoxycarbonylamino-1-phenylpropan-2-yl)-1,3,4-oxadiazol-2-yl)-5-(bromomethyl)-N-methyl-N-(methylsulfonyl)benzenamine using a similar procedure as described for the preparation of Example 40. $^1$H NMR (CD$_3$OD) δ 7.93 (m, 2H), 7.68 (s, 1H), 7.32 (m, 3H), 7.09 (m, 2H), 4.59 (s, 2H), 4.10 (m, 1H), 3.45 (s, 2H), 3.38 (s, 3H), 2.96 (s, 3H), 1.88 (s, 3H), 1.78 (m, 6H), 1.60 (m, 2H).

Example 42

3-(5-((R)-2-Amino-1-phenylpropan-2-yl)-1,3,4-oxadiazol-2-yl)-5-(2-(carbonitrile)phenyl)-N-methyl-N-(methylsulfonyl)benzenamine

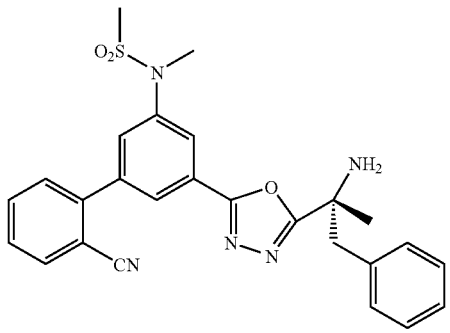

A solution of 3-(5-((R)-2-tert-butoxycarbonylamino-1-phenylpropan-2-yl)-1,3,4-oxadiazol-2-yl)-5-(2-(carbonitrile)phenyl)-N-methyl-N-(methylsulfonyl)benzenamine (20 mg, 0.034 mmol) in 2 mL TFA and 2 mL CH$_2$Cl$_2$ was stirred at rt for 1 h and concentrated. Purification by reverse phase preparative HPLC (5-95% CH$_3$CN in water containing 0.1% TFA) and lyophilization gave 3-(5-((R)-2-amino-1-phenylpropan-2-yl)-1,3,4-oxadiazol-2-yl)-5-(2-(carbonitrile)phenyl)-N-methyl-N-(methylsulfonyl)benzenamine as the TFA salt. $^1$H NMR (CD$_3$OD) δ 8.15 (t, J=1.8 Hz, 1H), 8.11 (t, J=1.6 Hz, 1H), 7.98 (t, J=1.7 Hz, 1H), 7.93 (d, J=7.7 Hz, 1H), 7.84 (m, 1H), 7.72 (d, J=7.9 Hz, 1H), 7.65 (m, 1H), 7.31 (m, 3H), 7.11 (m, 2H), 3.45 (m, 5H), 3.02 (s, 3H), 1.89 (s, 3H).

Example 43

3-(5-((R)-2-Amino-1-phenylpropan-2-yl)-1,3,4-oxadiazol-2-yl)-5-(2-(aminomethyl)phenyl)-N-methyl-N-(methylsulfonyl)benzenamine

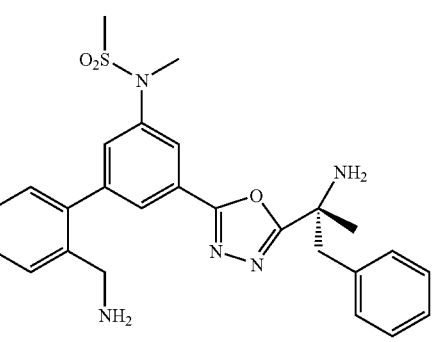

A solution of 3-(5-((R)-2-tert-butoxycarbonylamino-1-phenylpropan-2-yl)-1,3,4-oxadiazol-2-yl)-5-(2-(aminomethyl)phenyl)-N-methyl-N-(methylsulfonyl)benzenamine (10.2 mg, 0.017 mmol) in 0.5 mL TFA and 0.5 mL CH$_2$Cl$_2$ was stirred at rt for 1.5 h, concentrated and lyophilized to give 3-(5-(2-amino-1-phenylpropan-2-yl)-1,3,4-oxadiazol-2-yl)-5-((R)-2-(aminomethyl)phenyl)-N-methyl-N-(methylsulfonyl)benzenamine as the TFA salt. $^1$H NMR (CD$_3$OD) δ 8.08 (m, 1H), 7.92 (m, 1H), 7.76 (m, 1H), 7.63 (m, 1H), 7.58 (m, 2H), 7.48 (m, 1H), 7.32 (m, 3H), 7.10 (m, 2H), 4.14 (s, 2H), 3.45 (m, 5H), 3.03 (s, 3H), 1.89 (s, 3H).

Example 44

3-(5-((R)-2-Amino-1-phenylpropan-2-yl)-1,3,4-oxadiazol-2-yl)-5-(2-(acetamidomethyl)phenyl)-N-meth 1-N-(methylsulfonyl)benzenamine

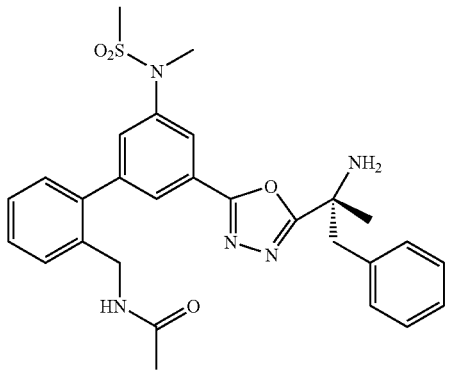

A solution of 3-(5-((R)-2-tert-butoxycarbonylamino-1-phenylpropan-2-yl)-1,3,4-oxadiazol-2-yl)-5-(2-(aminomethyl)phenyl)-N-methyl-N-(methylsulfonyl)benzenamine (10 mg, 0.017 mmol), acetic anhydride (0.008 mL, 0.085 mmol) and triethylamine (0.014 mL, 0.102 mmol) in 0.2 mL CH$_2$Cl$_2$ was stirred at rt for 2 h. The reaction mixture was concentrated, purified by reverse phase preparative HPLC (5-95% CH$_3$CN in water containing 0.1% TFA) and dissolved in 0.5 mL TFA and 0.5 mL CH$_2$Cl$_2$. The reaction was stirred at rt for 1.5 h, concentrated and lyophilized to give 3-(5-((R)-2-amino-1-phenylpropan-2-yl)-1,3,4-oxadiazol-2-yl)-5-(2-(acetamidomethyl)phenyl)-N-methyl-N-(methylsulfonyl)benzenamine as the TFA salt. $^1$H NMR (CD$_3$OD) δ 8.05 (m, 1H), 7.90 (m, 1H), 7.72 (m, 1H), 7.46 (m, 3H), 7.31 (m, 4H), 7.10 (m, 2H), 4.31 (s, 2H), 3.45 (s, 2H), 3.42 (s, 3H), 3.00 (s, 3H), 1.88 (s, 3H), 1.86 (s, 3H).

Example 45

3-(5-((R)-2-Amino-1-phenylpropan-2-yl)-1,3,4-oxadiazol-2-yl)-5-(2-((dimethylamino)methyl)phenyl)-N-methyl-N-(methylsulfonyl)benzenamine

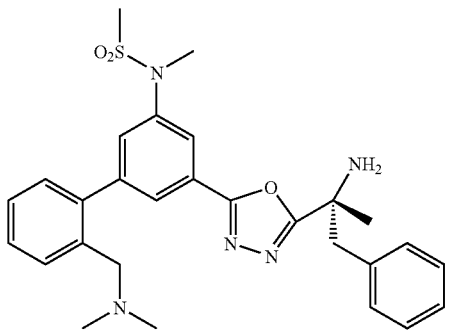

A solution of 3-(5-((R)-2-tert-butoxycarbonylamino-1-phenylpropan-2-yl)-1,3,4-oxadiazol-2-yl)-5-(2-(aminomethyl)phenyl)-N-methyl-N-(methylsulfonyl)benzenamine (10 mg, 0.017 mmol), formaldehyde (37% solution in water, 0.007 mL, 0.085 mmol) and sodium triacetoxyborohydride (7.2 mg, 0.034 mmol) in 0.3 mL dichloroethane and 0.1 mL methanol was stirred at rt overnight. The reaction mixture was concentrated, purified by reverse phase preparative HPLC (5-95% CH$_3$CN in water containing 0.1% TFA) and dissolved in 0.5 mL TFA and 0.5 mL CH$_2$Cl$_2$. The reaction was stirred at rt for 1.5 h, concentrated and lyophilized to give 3-(5-((R)-2-amino-1-phenylpropan-2-yl)-1,3,4-oxadiazol-2-yl)-5-(2-((dimethylamino)methyl)phenyl)-N-methyl-N-(methylsulfonyl)benzenamine as the TFA salt. $^1$H NMR (CD$_3$OD) δ 8.12 (m, 1H), 7.92 (m, 1H), 7.72 (m, 2H), 7.65 (m, 2H), 7.54 (m, 1H), 7.32 (m, 3H), 7.11 (m, 2H), 4.44 (s, 2H), 3.47 (s, 2H), 3.46 (s, 3H), 3.07 (s, 3H), 2.72 (s, 6H), 1.90 (s, 3H).

Example 46

3-(5-(R)-2-Amino-1-phenylpropan-2-yl)-1,3,4-oxadiazol-2-yl)-5-(2-((3,3,3-trifluoropropylamino)methyl)phenyl)-N-methyl-N-(methylsulfonyl)benzenamine

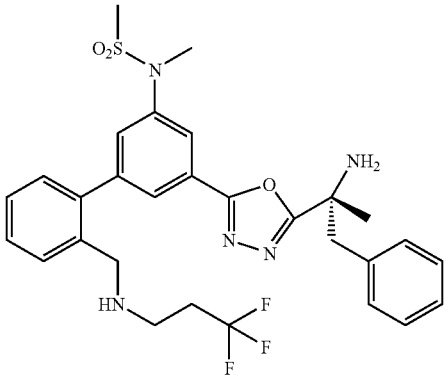

To a solution of 3-(5-((R)-2-tert-butoxycarbonylamino-1-phenylpropan-2-yl)-1,3,4-oxadiazol-2-yl)-5-(2-(aminomethyl)phenyl)-N-methyl-N-(methylsulfonyl)benzenanine (10 mg, 0.017 mmol) and 3,3,3-trifluoropropanal (1.9 mg, 0.017 mmol) in 0.2 mL dichloroethane, cooled to 0° C., was added sodium triacetoxyborohydride (3.8 mg, 0.018 mmol) and acetic acid (catalytic amount). The reaction was stirred at rt overnight and concentrated. Purification by reverse phase preparative HPLC (5-95% CH$_3$CN in water containing 0.1% TFA) gave an oil which was dissolved in 0.5 mL TFA and 0.5 mL CH$_2$Cl$_2$. The reaction was stirred at rt for 1.5 h, concentrated and lyophilized to give 3-(5-(2-amino-1-phenylpropan-2-yl)-1,3,4-oxadiazol-2-yl)-5-(2-((3,3,3-trifluoropropylamino)methyl)phenyl)-N-methyl-N-(methylsulfonyl) benzenamine as the TFA salt. $^1$H NMR (CD$_3$OD) δ 8.10 (s, 1H), 7.93 (s, 1H), 7.79 (s, 1H), 7.69 (m, 1H), 7.62 (m, 2H), 7.53 (m, 1H), 7.32 (m, 3H), 7.10 (m, 2H), 4.31 (s, 2H), 3.46 (m, 5H), 3.27 (m, 2H), 3.05 (s, 3H), 2.64 (m, 2H), 1.89 (s, 3H).

Example 47

3-(5-((R)-2-Amino-1-phenylpropan-2-yl)-1,3,4-oxa-diazol-2-yl)-5-(2-((2,2,2-trifluoroacetamido)methyl)phenyl)-N-methyl-N-(methylsulfonyl)benzenamine

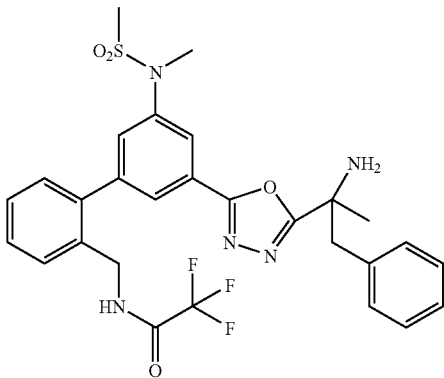

A solution of 3-(5-((R)-2-tert-butoxycarbonylamino-1-phenylpropan-2-yl)-1,3,4-oxadiazol-2-yl)-5-(2-(aminomethyl)phenyl)-N-methyl-N-(methylsulfonyl)benzenamine (10 mg, 0.017 mmol), ethyl trifluoroacetate (0.010 mL, 0.085 mmol) (Intermediate XXIX) and triethylamine (0.014 mL, 0.102 mmol) in 0.2 mL methanol was stirred at rt overnight. The reaction mixture was concentrated, purified by reverse phase preparative HPLC (5-95% CH$_3$CN in water containing 0.1% TFA) and dissolved in 0.75 mL TFA and 0.25 mL CH$_2$Cl$_2$. The reaction was stirred at rt for 1 h, concentrated and lyophilized to give 3-(5-((R)-2-amino-1-phenylpropan-2-yl)-1,3,4-oxadiazol-2-yl)-5-(2-((2,2,2-trifluoroacetamido)methyl)phenyl)-N-methyl-N-(methylsulfonyl)benzenamine as the TFA salt. $^1$H NMR (CD$_3$OD) δ 8.06 (m, 1H), 7.90 (m, 1H), 7.72 (m, 1H), 7.47 (m, 3H), 7.31 (m, 4H), 7.09 (m, 2H), 4.49 (s, 2H), 3.45 (s, 2H), 3.42 (s, 3H), 3.00 (s, 3H), 1.88 (s, 3H).

Example 48

3-(5-((R)-2-Amino-1-phenylpropan-2-yl)-1,3,4-oxa-diazol-2-yl)-5-(1H-imidazol-4-yl)-N-methyl-N-(methylsulfonyl)benzenamine

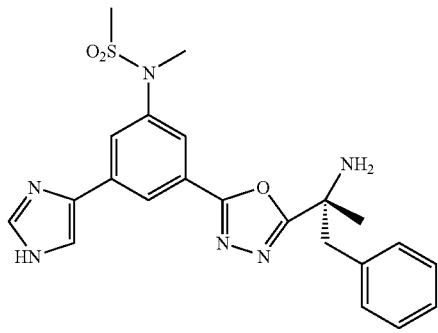

Step A: Coupling

To a solution of 4-iodo-1-trityl-1H-imidazole (Preparation described in Jetter, M. C., Boyd, R. E., Reitz, A. B. *Org. Prep. Proced. Int.* 1996, 28(6), 709-710; 87 mg, 0.20 mmol) in 2 mL TF was added ethylmagnesium bromide (1.0 M solution in THF, 0.24 mL, 0.24 mmol) dropwise. The reaction was stirred at rt for 0.5 h and zinc chloride (0.5 M solution in THF, 0.8 mL, 0.4 mmol) was added. After stirring for 1 h, 3-(5-((R)-2-tert-butoxycarbonylamino-1-phenylpropan-2-yl)-1,3,4-oxadiazol-2-yl)-5-bromo-N-methyl-N-(methylsulfonyl)benzenamine (100 mg, 0.18 mmol) and tetrakis(triphenylphosphine)palladium(0) (20.8 mg, 0.018 mmol) were added. The mixture was heated in a microwave oven to 80° C. for 0.5 h, quenched with saturated ammonium chloride and extracted with EtOAc. The combined organic layers were washed with water and brine. Drying, solvent evaporation and flash chromatography (15-65% EtOAc/hexanes) gave 3-(5-((R)-2-tert-butoxycarbonylamino-1-phenylpropan-2-yl)-1,3,4-oxadiazol-2-yl)-N-methyl-N-(methylsulfonyl)-5-(1-trityl-1H-imidazol-4-yl)benzenamine. $^1$H NMR (CDCl3) δ 8.23 (s, 1H), 7.98 (s, 1H), 7.87 (s, 1H), 7.54 (d, J=0.8 Hz, 1H), 7.40-7.00 (m, 21H), 3.56 (d, J=12 Hz, 1H), 3.44 (d, J=12 Hz, 1H), 3.39 (s, 3H), 2.92 (s, 3H), 1.72 (s, 3H), 1.41 (s, 9H).

Step B: Deprotection

To 3-(5-((R)-2-tert-butoxycarbonylamino-1-phenylpropan-2-yl)-1,3,4-oxadiazol-2-yl)-N-methyl-N-(methylsulfonyl)-5-(1-trityl-1H-imidazol-4-yl)benzenamine (40 mg, 0.050 mmol) was added 1.9 mL TFA and 0.1 mL water. The reaction was stirred at rt overnight. Concentration, purification by reverse phase preparative HPLC (5-95% CH$_3$CN in water containing 0.1% TFA) and lyophilization gave 3-(5-((R)-2-amino-1-phenylpropan-2-yl)-1,3,4-oxadiazol-2-yl)-5-(1H-imidazol-4-yl)-N-methyl-N-(methylsulfonyl)benzenamine as the TFA salt. $^1$H NMR (CD$_3$OD) δ 8.76 (s, 1H), 8.38 (m, 1H), 8.08 (m, 1H), 8.06 (m, 1H), 8.04 (m, 1H), 7.32 (m, 3H), 7.12 (m, 2H), 3.48 (s, 2H), 3.44 (s, 3H), 3.03 (s, 3H), 1.91 (s, 3H).

Example 49

3-(5-((R)-2-Amino-1-phenylpropan-2-yl)-1,3,4-oxa-diazol-2-yl)-5-(1H-imidazol-2-yl)-N-methyl-N-(methylsulfonyl)benzenamine

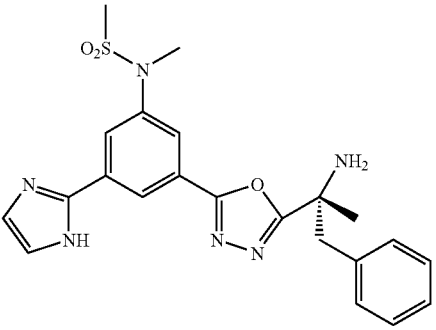

Step A: Coupling

To a solution of N,N-dimethylsulfamoyl)imidazole (Preparation described in Winter, J., Retey, J. *Synthesis.* 1994, 3, 245-246; 47 mg, 0.27 mmol) in 1 mL THF, cooled to −78°

C. was added n-butyllithium (2.5 M solution in hexanes, 0.12 mL, 0.29 mmol) dropwise. The reaction was stirred at −78° C. for 15 min and zinc chloride (0.5 M solution in THF, 1.6 mL, 0.81 mmol) was added. After warming to rt over 1 h, 3-(5-((R)-2-tert-butoxycarbonylamino-1-phenylpropan-2-yl)-1,3,4-oxadiazol-2-yl)-5-bromo-N-methyl-N-(methylsulfonyl) benzenamine (100 mg, 0.18 mmol) and tetrakis (triphenylphosphine)palladium(0) (20.8 mg, 0.018 mmol) were added. The mixture was heated in a microwave oven to 80° C. for 0.75 h, quenched with water and extracted with EtOAc. The combined organic layers were washed with brine. Drying, solvent evaporation and flash chromatography (50-100% EtOAc/hexanes) gave 3-(1-(dimethylsulfamoyl)-1H-imidazol-2-yl)-5-(5-((R)-2-tert-butoxycarbonylamino-1-phenylpropan-2-yl)-1,3,4-oxadiazol-2-yl)-N-methyl-N-(methylsulfonyl)benzenamine. $^1$H NMR (CDCl$_3$) δ 8.26 (m, 1H), 8.15 (m, 1H), 7.87 (m, 1H), 7.49 (d, J=1.6 Hz, 1H), 7.26 (m, 3H), 7.18 (d, J=1.6 Hz, 1H), 7.08 (m, 2H), 3.60 (d, J=12 Hz, 1H), 3.40 (m, 4H), 2.95 (s, 3H), 2.64 (s, 6H), 1.71 (s, 3H), 1.42 (bs, 9H).

Step B: Deprotection

A solution of 3-(1-(dimethylsulfamoyl)-1H-imindazol-2-yl)-5-(5-((R)-2-tert-butoxycarbonylamino-1-phenylpropan-2-yl)-1,3,4-oxadiazol-2-yl)-N-methyl-N-(methylsulfonyl) benzenamine (39 mg, 0.059 mmol) in HCl (10% aqueous solution, 10 mL) and 1 mL MeCN was stirred at rt for 3 days. The reaction was concentrated, made basic with saturated sodium bicarbonate and extracted with chloroform. Drying, solvent evaporation, purification by reverse phase preparative HPLC (5-95% CH$_3$CN in water containing 0.1% TFA) and lyophilization gave 3-(5-((R)-2-amino-1-phenylpropan-2-yl)-1,3,4-oxadiazol-2-yl)-5-(1H-imidazol-2-yl)-N-methyl-N-(methylsulfonyl)benzenamine as the TFA salt. $^1$H NMR (CD$_3$OD) δ 8.59 (s, 1H), 8.23 (s, 1H), 8.20 (s, 1H), 7.56 (s, 2H), 7.32 (m, 3H), 7.10 (m, 2H), 3.49 (s, 2H), 3.46 (s, 3H), 3.05 (s, 3H), 1.90 (s, 3H).

Example 50

N—[(R)-1-(4-fluorophenyl)ethyl]-3-[5-(1-hydroxy-1-methyl-2-phenylethyl)-2-furyl]-5-[methyl(methylsulfonyl)amino]benzamide

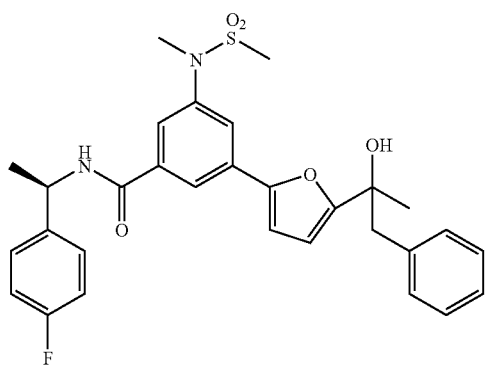

Step A: Grignard Addition

To a solution of Intermediate LVII (0.050 g, 0.11 mmol) in 5 mL THF at 0° C. was added 3M MeMgBr in THF (0.11 mL, 0.34 mmol). The bath was removed, and the reaction was allowed to warm to rt, when it was quenched by the addition od satd. NaHCO$_3$ and diluted with EtOAc. The layers were separated, the aqueous washed with EtOAc (2×), the combined organics were washed with brine, dried over Na2SO4, filtered and conc. The material was used in the next step without further purification. LCMS [M+H]+=461.

Step B: Oxidation

To a solution of alcohol from Step A (0.080 g, 0.17 mmol) in 2 mL CH$_2$Cl$_2$ was added a 1M solution of Dess-Martin periodinane (0.35 mL, 0.35 mmol). After 4 h, the reaction was quenched by the addition of satd. NaHCO$_3$ and diluted with CH$_2$Cl$_2$. The layers were separated, and the organic layer was dried over Na2SO4, filtered and concentrated. The residue was purified by reverse phase preparative HPLC (5-95% CH$_3$CN in water containing 0.1% TFA) to afford the desired ketone. $^1$H NMR (CDCl3) δ 8.10 (m, 1H), 7.93 (m, 1H), 7.81 (m, 1H), 7.38 (m, 2H), 7.30 (d, J=3.7 Hz, 1H), 7.06 (m, 2H), 6.91 (d, J=3.7 Hz, 1H), 6.77 (d, J=7.6 Hz, 1H), 5.32 (m, 1H), 3.39 (s, 3H), 2.54 (s, 3H), 1.65 (d, J=7.0 Hz, 3H). LCMS [M+H]$^+$=459.

Step C: Grignard Addition

To a solution of ketone from Step B in 5 mL THF at 0° C. was added 1M BnMgCl in THF (0.39 mL, 0.39 mmol). After 2 h, the reaction was quenched by the addition of satd. NaHCO$_3$ and diluted with EtOAc. The layers were separated, and The aqueous layer was extracted with EtOAc (2×). The combined organics were washed with brine, dried over Na$_2$SO$_4$, filtered and concentrated. The residue was purified by reverse phase preparative HPLC (5-95% CH$_3$CN in water containing 0.1% TFA) to afford N—[(R)-1-(4-fluorophenyl)ethyl]-3-[5-(1-hydroxy-1-methyl-2-phenylethyl)-2-furyl]-5-[methyl(methyl sulfonyl)amino]benzamide as a white foam after lyophilization. $^1$H NMR (CD$_3$OD) δ 7.87 (m, 1H), 7.71 (m, 1H), 7.64 (m, 1H), 7.39-7.20 (m, 5H), 7.08-6.99 (m, 4H), 6.67 (d, J=3.4 Hz, 1H), 6.44 (d, J=7.5 Hz, 1H), 6.19 (d, J=3.4 Hz, 1H), 5.33 (m, 1H), 3.37 (s, 3H), 3.25 (d, J=13.3 Hz, 1H), 3.14 (d, J=13.3 Hz, 1H), 2.90 (s, 3H), 1.65 (s, 3H). LCMS [M+H]+=551.

Example 51

N—[(R)-1-(4-fluorophenyl)ethyl]-3-[5-(1-amino-1-methyl-2-phenylethyl)-2-furyl]-5-[methyl(methylsulfonyl)amino]benzamide

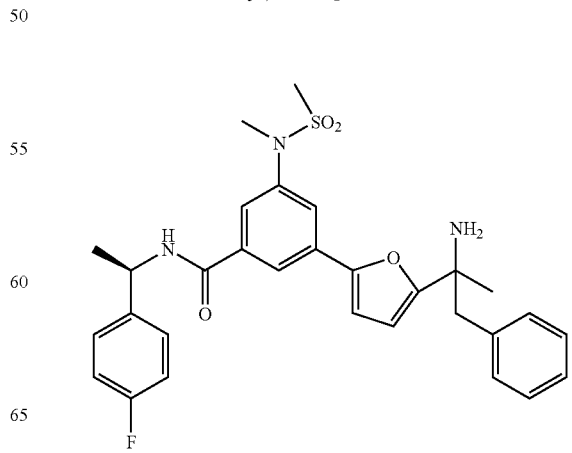

Step A: Ritter Reaction

To a solution of Example 50 (0.080 g, 0.15 mmol) in 1 mL CHCl$_3$ was added a suspension of sodium azide (0.094 g, 1.45 mmol) in TFA (0.06 mL, 0.73 mmol). The solution progressively turned dark over 1 h to afford a mixture of desired product and a byproduct resulting from dehydration. Concentrated and used as is in next reaction. LCMS [M+H]$^+$=575.

Step B: Azide Reduction

To a solution of unpurified material from Step A in 2 mL EtOH was added a spatula tip of palladium on carbon. The reaction vessel was placed under an atmosphere of hydrogen gas for 20 h. Concentrated and purified by reverse phase preparative HPLC (5-95% CH$_3$CN in water containing 0.1% TFA) to afford N—[(R)-1-(4-fluorophenyl)ethyl]-3-[5-(1-amino-1-methyl-2-phenylethyl)-2-furyl]-5-[methyl(methylsulfonyl)amino]benzamide as a white foam after lyophilization. $^1$H NMR (CD$_3$OD) δ 7.87 (m, 1H), 7.71 (m, 1H), 7.64 (m, 1H), 7.39-7.20 (m, 5H), 7.08-6.99 (m, 4H), 6.67 (d, J=3.4 Hz, 1H), 6.44 (d, J=7.5 Hz, 1H), 6.19 (d, J=3.4 Hz, 1H), 5.33 (m, 1H), 3.37 (s, 3H), 3.25 (d, J=13.3 Hz, 1H), 3.14 (d, J=13.3 Hz, 1H), 2.90 (s, 3H), 1.65 (s, 3H). LCMS [M+H]+=551.

Example 52

N—[(R)-1-(4-fluorophenyl)ethyl]-3-[5-(1-amino-2-phenylethyl)-2-furyl]-5-[methyl(methylsulfonyl)amino]benzamide

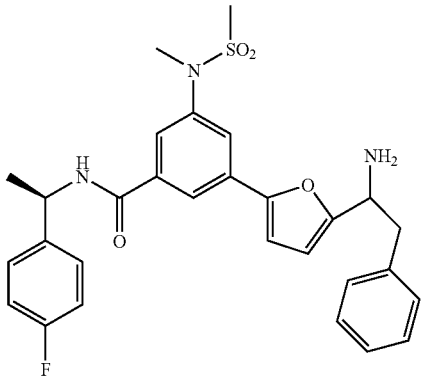

To a solution of Intermediate LVIII (0.040 g, 0.073 mmol) in 10 mL THF at 0° C. was added 1M BnMgBr (0.29 mL, 0.29 mmol), and the reaction was allowed to warm to rt over 30 min. The reaction was quenched by the addition of satd. NaHCO$_3$ and diluted with EtOAc. The layers were separated, and the aqueous layer was extracted with EtOAc (2×). The combined organic were dried over Na$_2$SO$_4$, filtered and concentrated. This residue was immediately taken up in 5 mL MeOH, and 4 mL 4N HCl in dioxane was added. After 1 h at rt, the reaction was concentrated and purified by reverse phase preparative HPLC (5-95% CH$_3$CN in water containing 0.1% TFA) to afford N—[(R)-1-(4-fluorophenyl)ethyl]-3-[5-(1-amino-2-phenylethyl)-2-furyl]-5-[methyl(methylsulfonyl)amino]benzamide as a white foam after lyophilization. $^1$H NMR (CD$_3$OD) δ 8.92 (d, J=7.7 Hz, 1H), 8.10 (m, 1H), 7.92 (m, 1H), 7.79 (m, 1H), 7.42 (m, 2H), 7.27-7.21 (m, 5H), 7.07 (m, 2H), 6.90 (d, J=3.5 Hz, 1H), 6.50 (d, J=3.5 Hz, 1H), 5.25 (m, 1H), 4.74 (dd, J=8.7, 5.4 Hz, 1H), 3.41-3.30 (m, 2H), 3.37 (s, 3H), 2.96 (s, 3H), 1.57 (d, J=6.9 Hz, 3H). HRMS exact mass calc for C$_{29}$H$_{30}$FN$_3$O$_4$S [M+H]$^+$: 536.2014; observed: 536.2021.

Example 53

3'-[5-((R)-1-amino-1-methyl-2-phenylethyl)-1,3,4-oxadiazol-2-yl]-5'-{[(2,2,2-trifluoro-1-phenylethyl)amino]methyl}biphenyl-2-carbonitrile

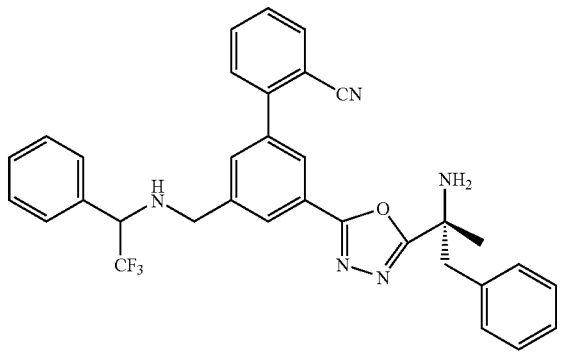

Prepared using a reaction sequence similar to that described for the synthesis of Example 37 using Intermediate LIX. LCMS [M+H]$^+$=568.

Example 54

3'-[5-((R)-1-amino-1-methyl-2-phenylethyl)-1,3,4-oxadiazol-2-yl]-5'-(cyclopropylcarbonyl)biphenyl-2-carbonitrile

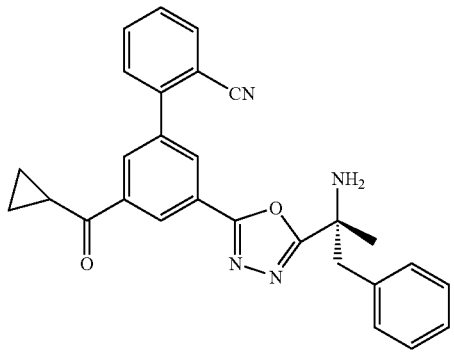

Prepared using a reaction sequence similar to that described for the synthesis of Example 12 using Intermediate XVII.

The following examples in Table 1 were prepared from the relevant acid intermediates and amines using a procedure similar to that reported for the synthesis of Example 9.

| Intermediate | Example | Structure | LC/MS [M + H]+ |
|---|---|---|---|
| | 55 | | 512 |
| | 56 | | 474 |
| | 57 | | 468 |
| | 58 | | 482 |

-continued

| Intermediate | Example | Structure | LC/MS [M + H]+ |
|---|---|---|---|
| | 59 | | 544 |
| | 60 | | 560 |
| | 61 | | 526 |
| | 62 | | 514 |

| Intermediate | Example | Structure | LC/MS [M + H]+ |
|---|---|---|---|
| (structure) | 63 | (structure) | 496 |
| (structure) | 64 | (structure) | 524 |
| (structure) | 65 | (structure) | 510 |
| (structure) | 66 | (structure) | 514 |

-continued

| Intermediate | Example | Structure | LC/MS [M + H]+ |
|---|---|---|---|
| | 67 | | 512 |
| | 68 | | 486 |
| | 69 | | 500 |
| | 70 | | 566 |

-continued

| Intermediate | Example | Structure | LC/MS [M + H]+ |
|---|---|---|---|
| | 71 | | 548 |
| | 72 | | 602 |
| | 73 | | 516 |
| | 74 | | 582 |

-continued

| Intermediate | Example | Structure | LC/MS [M + H]+ |
|---|---|---|---|
| | 75 | | 480 |
| | 76 | | 496 |
| | 77 | | 480 |
| | 78 | | 478 |

| Intermediate | Example | Structure | LC/MS [M + H]+ |
|---|---|---|---|
| | 79 | | 522 |
| | 80 | | 496 |
| | 81 | | 520 |
| | 82 | | 534 |

-continued

| Intermediate | Example | Structure | LC/MS [M + H]+ |
|---|---|---|---|
| | 83 | | 530 |
| | 84 | | 558 |
| | 85 | | 558 |
| | 86 | | 555 |

| Intermediate | Example | Structure | LC/MS [M + H]+ |
|---|---|---|---|
| | 87 | | 633 |
| | 88 | | 508 |
| | 89 | | 582 |
| | 90 | | 476 |

-continued

| Intermediate | Example | Structure | LC/MS [M + H]+ |
|---|---|---|---|
| | 91 | | 502 |
| | 92 | | 516 |
| | 93 | | 504 |

-continued

| Intermediate | Example | Structure | LC/MS [M + H]+ |
|---|---|---|---|
| | 94 | | 506 |
| | 95 | | 528 |
| | 96 | | 542 |
| | 97 | | 542 |

| Intermediate | Example | Structure | LC/MS [M + H]+ |
|---|---|---|---|
| (structure) | 98 | (structure) | 518 |
| (structure) | 99 | (structure) | 518 |
| (structure) | 100 | (structure) | 520 |
| (structure) | 101 | (structure) | 554 |

| Intermediate | Example | Structure | LC/MS [M + H]+ |
|---|---|---|---|
| (structure) | 102 | (structure) | 512 |
| (structure) | 103 | (structure) | 500 |
| (structure) | 104 | (structure) | 482 |
| (structure) | 105 | (structure) | 574 |

| Intermediate | Example | Structure | LC/MS [M + H]+ |
|---|---|---|---|
| (structure) | 106 | (structure) | 456 |
| (structure) | 107 | (structure) | 570 |
| (structure) | 108 | (structure) | 494 |
| (structure) | 109 | (structure) | 516 |

-continued

| Intermediate | Example | Structure | LC/MS [M + H]+ |
|---|---|---|---|
| | 110 | | 543 |
| | 111 | | 557 |
| | 112 | | 508 |
| | 113 | | 572 |

-continued

| Intermediate | Example | Structure | LC/MS [M + H]+ |
|---|---|---|---|
| | 114 | | 502 |
| | 115 | | 490 |
| | 116 | | 480 |
| | 117 | | 522 |

-continued

| Intermediate | Example | Structure | LC/MS [M + H]+ |
|---|---|---|---|
| (structure) | 118 | (structure) | 516 |
| (structure) | 119 | (structure) | 508 |
| (structure) | 120 | (structure) | 548 |
| (structure) | 121 | (structure) | 492 |

-continued

| Intermediate | Example | Structure | LC/MS [M + H]+ |
|---|---|---|---|
| | 122 | | 546 |
| | 123 | | 579 |
| | 124 | | 500 |
| | 125 | | 514 |

-continued

| Intermediate | Example | Structure | LC/MS [M + H]+ |
|---|---|---|---|
| | 126 | | 524 |
| | 127 | | 550 |
| | 128 | | 580 |
| | 129 | | 612 |

The following examples 130-134 in Table 2 were synthesized from Intermediate LVIII using a procedure similar to that described for the preparation of Example 52.

TABLE II

| Example | Structure | LCMS [M + H]$^+$ |
|---------|-----------|------------------|
| 130 | 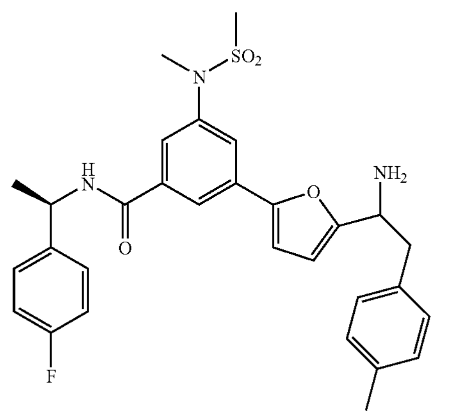 | 550 |
| 131 | 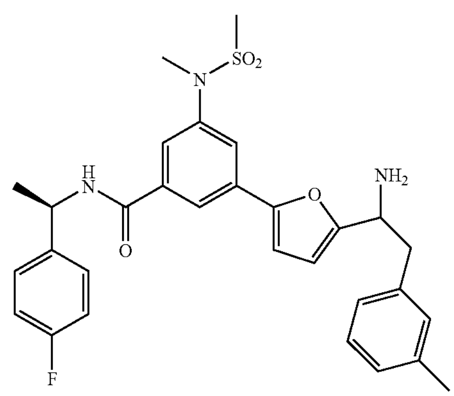 | 550 |
| 132 | 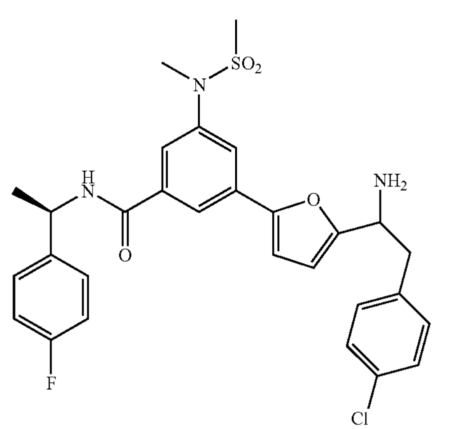 | 570 |

TABLE II-continued

| Example | Structure | LCMS [M + H]+ |
|---|---|---|
| 133 | 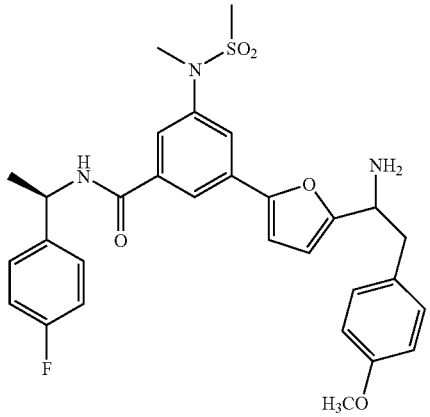 | 566 |
| 134 | 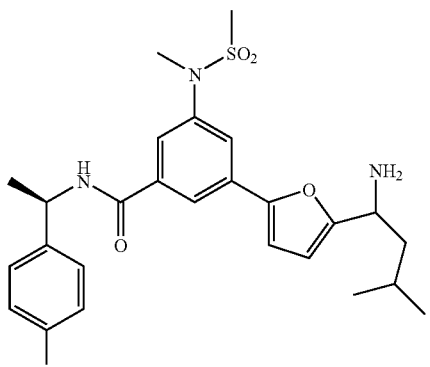 | 502 |

Example 135

(1-{5-[3-{[2-(3-chlorophenyl)pyrrolidin-1-yl]carbonyl}-5-(trifluoromethyl)phenyl]-1,3,4-oxadiazol-2-yl}-1-methyl-2-phenylethyl)amine2-{5-[3-{[2-(3-chlorophenyl)pyrrolidin-1-yl]carbonyl}-5-(trifluoromethyl)phenyl]-1,3,4-oxadiazol-2-yl}-(R)-1-phenylpropan-2-amine

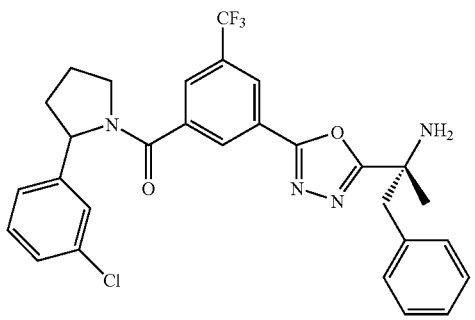

Prepared from diester Intermediate LXII, acylhydrazide Intermediate II and 2-(3-chlorophenyl)pyrrolidine using a procedure as described for the synthesis of Example 9. LCMS [(M)+H]+=546.

Example 136

3'-{5-[(1R)-1-amino-1-methyl-2-phenylethyl]-1,3,4-oxadiazol-2-yl}-3-(tert-butylthio)-5'-{[(21-yn-1-ylpyrrolidin-1-yl]carbonyl}biphenyl-2-carbonitrile

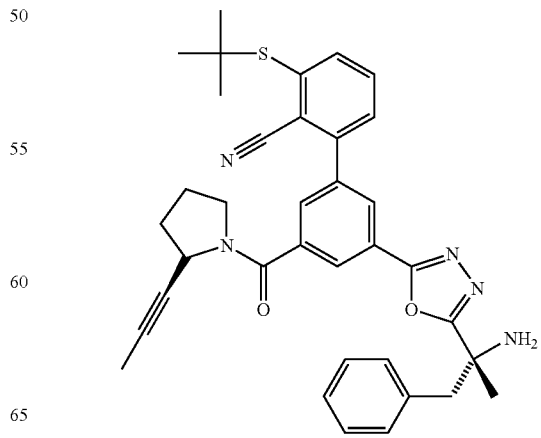

To a solution containing 75 mg (0.12 mmol) of the fluoro nitrile (Intermediate LXIII) in 2.0 mL of THF was added 16 mg (0.14 mmol) of sodium tert-butylate. The reaction mixture was heated at 65° C. for 16 h before it was cooled, evaporated and subjected to reverse phase chromatography to give xx (?) mg (36%) of the corresponding thiol derivative. This compound was dissolved in 3.0 mL of dichloromethane and cooled to 0° C. Trifluoroacetic acid (3.0 mL) was added and the resulting solution was stirred for 3 h. Evaporation of the solvent and reverse phase chromatography left the TFA salt of the desired compound. HRMS (M+H)=604.2696. $^1$H NMR (CD$_3$OD) δ 8.39 (s, 0.3H), 8.28 (s, 0.7H), 8.21 (s, 0.3H), 8.13 (s, 0.7H), 7.97 (s, 0.3H), 7.86 (s, 0.7H), 7.80 (m, 1H), 7.69 (d, J=7.5 Hz, 1H), 7.30-7.21 (m, 5H), 7.20 (d, J=7.5 Hz, 1H), 7.19-7.10 (m, 2H), 4.60 (bs, 1H), 3.67 (bt, 2H), 3.30 (s, 3H), 2.22-2.02 (m, 6H), 1.95 (s, 3H), 1.41 (s, 9H).

The following examples 137-159 in Table III were prepared from the relevant intermediates using a procedure similar to that reported for the synthesis of Example 136.

TABLE III

| Example | Structure | LC/MS M + H |
|---------|-----------|-------------|
| 137 | 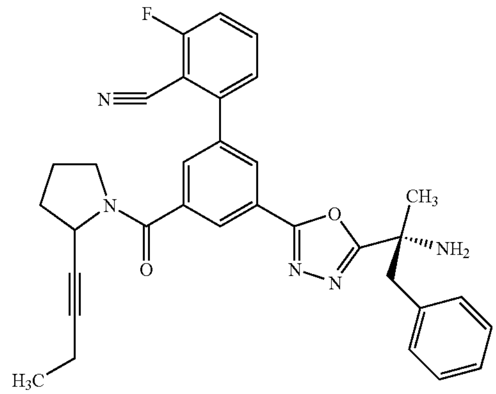 | 548.638 |
| 138 | 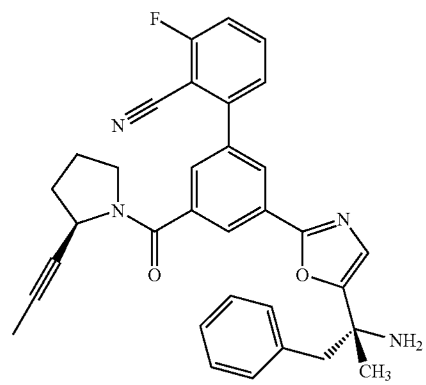 | 533.623<br>Prepared analogously to Example 38 |
| 139 | 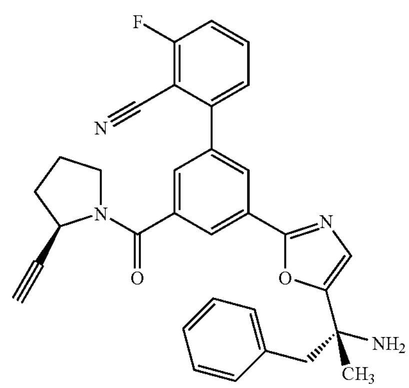 | 519.596 |

TABLE III-continued

| Example | Structure | LC/MS M + H |
|---------|-----------|-------------|
| 140 | 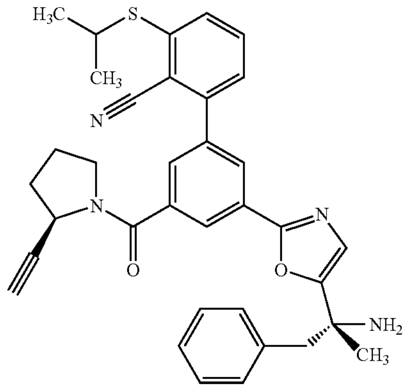 | 575.751 |
| 141 | 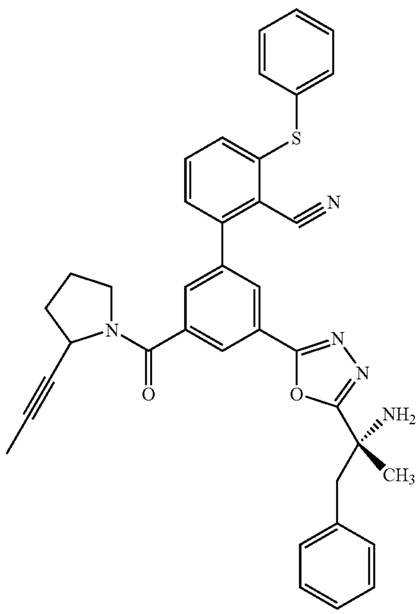 | 624.783 |
| 142 | 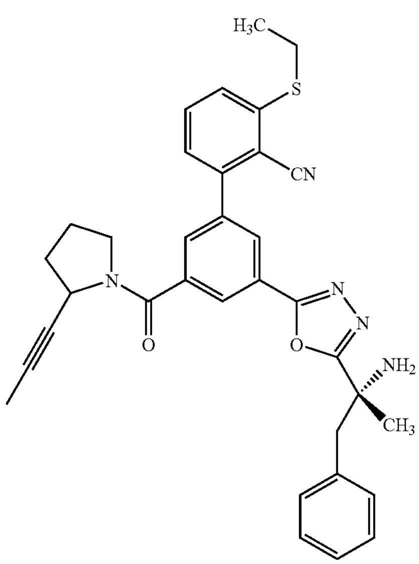 | 576.738 |

TABLE III-continued
| Example | Structure | LC/MS M + H |
|---------|-----------|-------------|
| 143 | 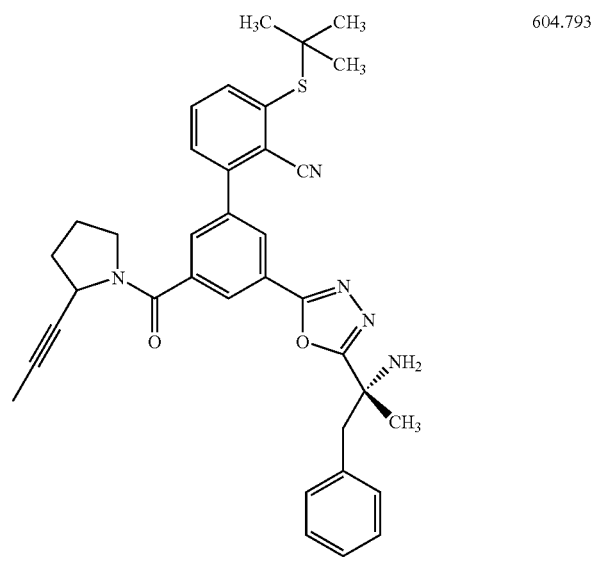 | 604.793 |
| 144 | 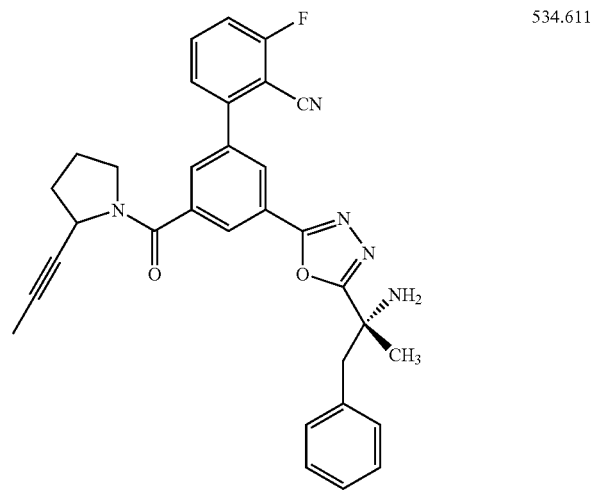 | 534.611 |

TABLE III-continued
| Example | Structure | LC/MS M + H |
|---|---|---|
| 145 | 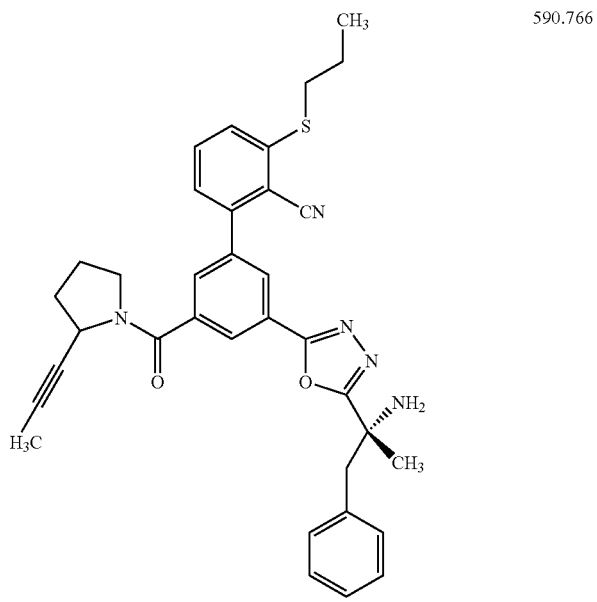 | 590.766 |
| 146 | 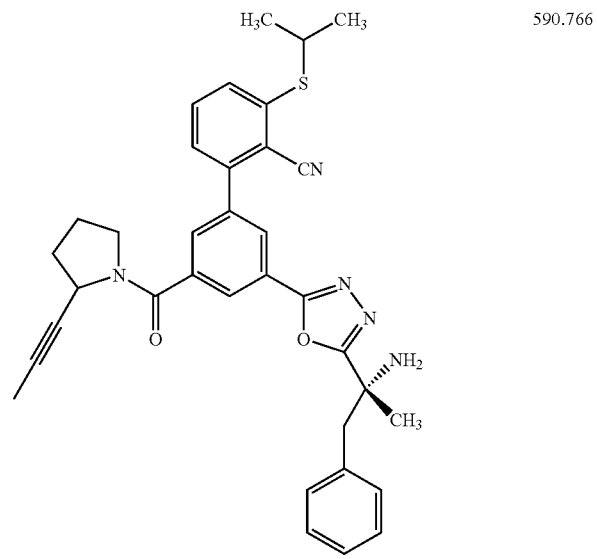 | 590.766 |

TABLE III-continued
| Example | Structure | LC/MS M + H |
|---------|-----------|-------------|
| 147 | 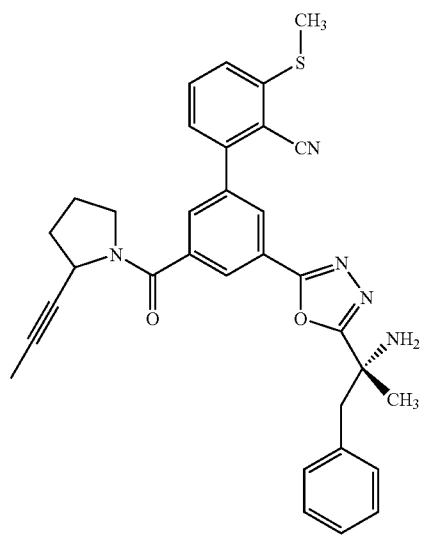 | 562.711 |
| 148 | 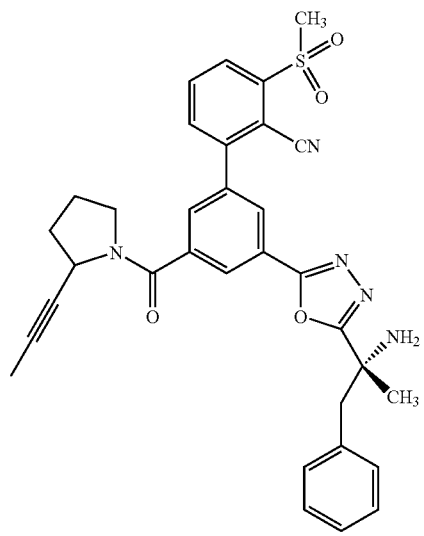 | 594.71<br>thiophenol was oxidized to sulfone with m-CPBA prior to Boo deprotection |

TABLE III-continued
| Example | Structure | LC/MS M + H |
|---------|-----------|-------------|
| 149 | 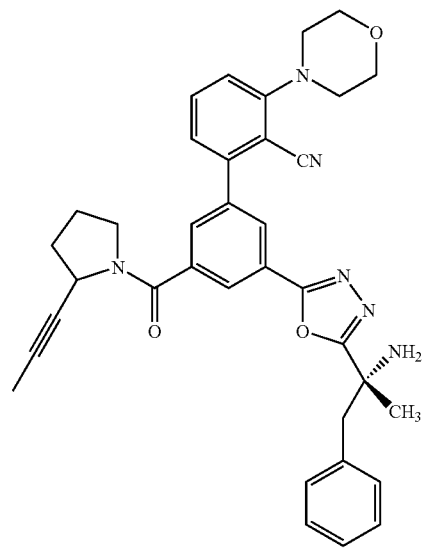 | 601.727 |
| 150 | 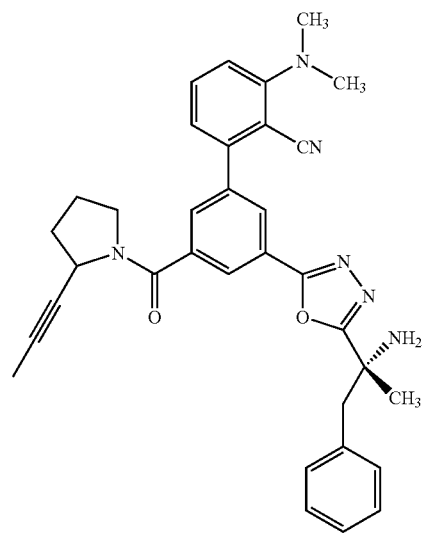 | 559.689 |

TABLE III-continued

| Example | Structure | LC/MS M + H |
|---------|-----------|-------------|
| 151 | 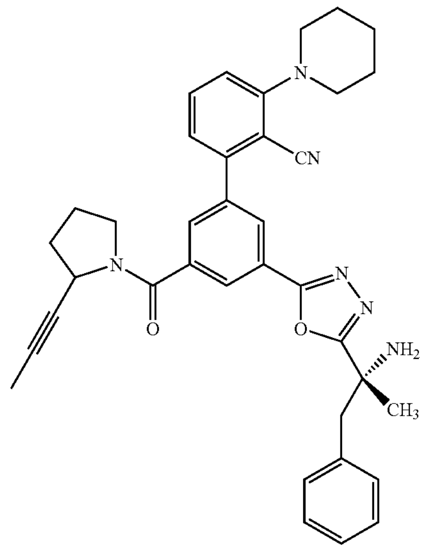 | 599.754 |
| 152 | 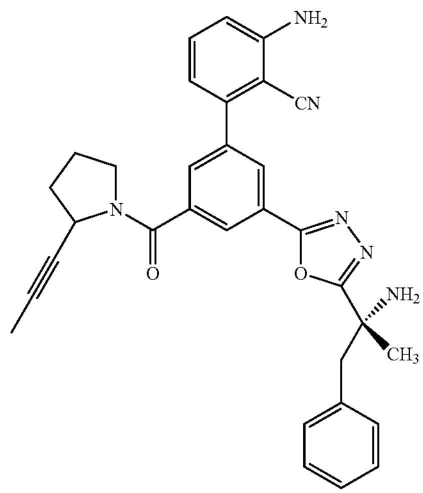 | 531.635 |
| 153 | 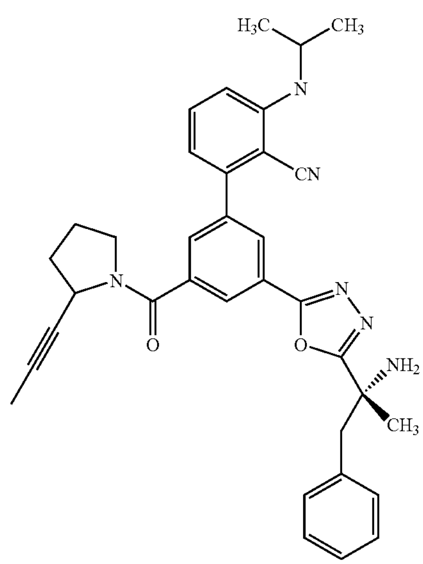 | 573.716 |

TABLE III-continued
| Example | Structure | LC/MS M + H |
|---|---|---|
| 154 | 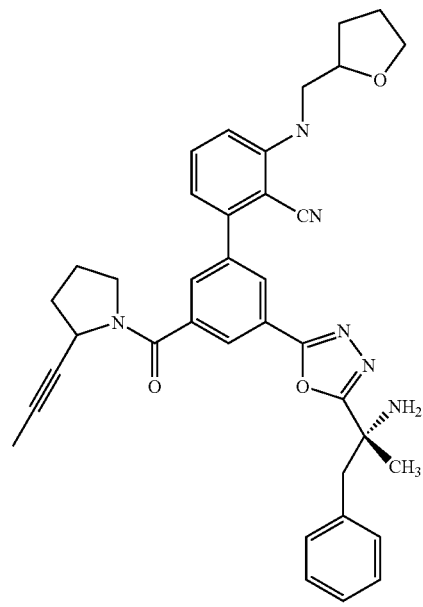 | 616.754 |
| 155 | 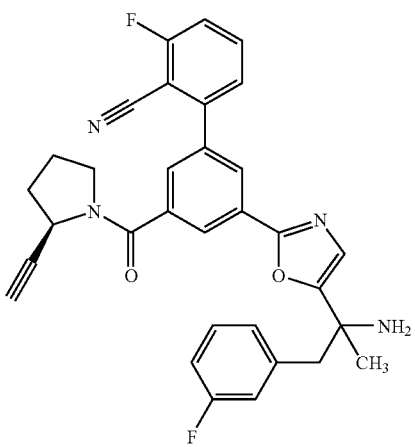 | 537.586 |
| 156 | 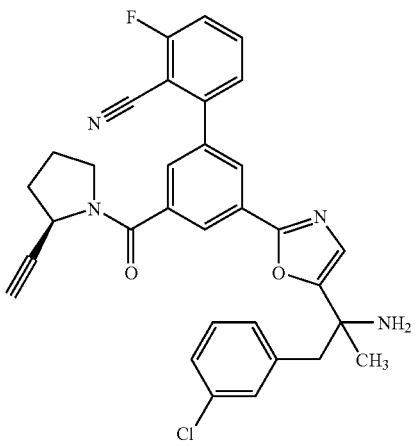 | 554.041 |

TABLE III-continued

| Example | Structure | LC/MS M + H |
|---------|-----------|-------------|
| 157 | 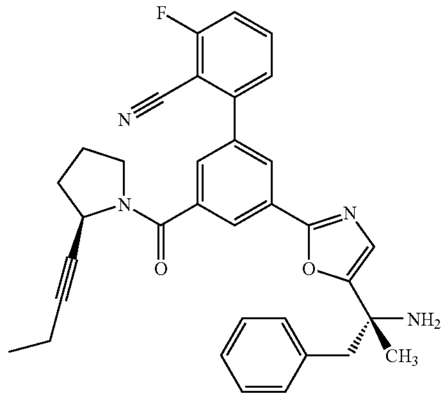 | 547.65 |
| 158 | 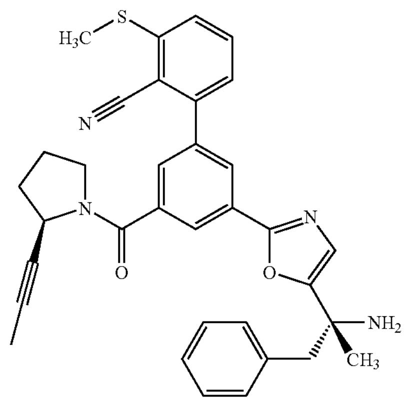 | 561.724 |
| 159 | 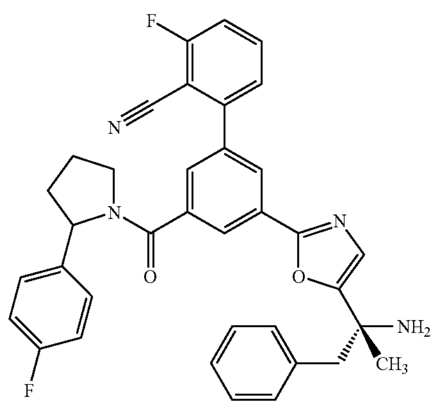 | 589.663 |

The following abbreviations are used throughout the text:
Me: methyl
Et: ethyl
Bu: butyl
t-Bu: tert butyl
i-Bu: isobutyl
Pr: propyl
i-Pr: isopropyl
Ar: aryl
Ph: phenyl
Ac: acetyl
Py: pyridine
DMF: N,N'-dimethyl formamide
THF: tetrahydrofuran
DMSO: dimethylsulfoxide
TMS: trimethyl silyl
TBAF: tetra-n-butyl ammonium fluoride
CBZ: benzyloxycarbonyl
Boc: tert-butyloxy carbonyl
BOP: Benzotriazol-1-yloxy-tris(dimethylamino)phosphonium hexafluorophosphate
CHAPS: 3-[(3-cholamidopropyl)dimethylammonio]-2-hydroxy-1-propanesulfonate
TEA: triethylamine
TFA: trifluoroacetic acid
NIS: N-iodo succinimide
DIBAL: diisopropyl aluminum hydride
DIC: diisopropylcarbodiimide HOBt: hydroxybenztriazole
HOAt: 1-hydroxy-7-aza-benztriazole
TPPTS: Trisulfonated triphenylphosphine, trisodium salt
EDC: 1-(3-dimethylaminopropyl)-3-ethylcarbodiimide hydrochloride
m-CPBA: (meta-chloroperoxybenzioc acid)
HMPA: (Hexamethylphosphoramide)
DMI: 1,3-dimethyl-2-imidazolaninone
rt: room temperature
HPLC: high performance liquid chromatography While some the compounds depicted in the table above are represented in their acid form, the invention is intended to encompass both the salt and free base forms of the compounds described above.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

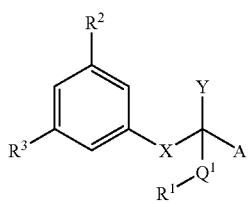

(I)

wherein:
X is selected from the group consisting of

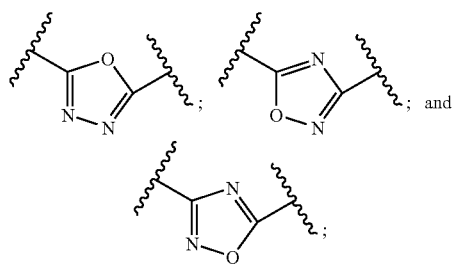

; and ;

A is selected from the group consisting of
(1) hydrogen,
(2) —$C_{1-10}$ alkyl, and
(3) —$C_{2-10}$ alkenyl,
wherein said alkyl or alkenyl is unsubstituted or substituted with one or more
(a) halo,
(b) —$C_{3-12}$ cycloalkyl,
(c) —OH,
(d) —CN,
(e) —O—$C_{1-10}$ alkyl,
(f) phenyl, or
(g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thiophenyl, triazolyl, oxazolyl, isoxazolyl, thiazolyl, oxadiazolyl, indolyl, quinolinyl, isoquinolinyl, benzimidazolyl, benzofuranyl, and benzoxazolyl,
and said phenyl and heteroaryl is unsubstituted or substituted with one or more
(i) halo,
(ii) —OH,
(iii) —CN,
(iv) —O—$C_{1-10}$ alkyl,
(v) —$C_{1-10}$ alkyl, or
(vi) —$C_{3-12}$ cycloalkyl;
Y is selected from the group consisting of
(1) —OH, and
(2) —$NR^hR^i$,
wherein $R^h$ and $R^i$ are selected from the group consisting of
(a) hydrogen,
(b) —$C_{1-10}$ alkyl, and
(c) —$C_{0-6}$ alkyl-$C_{6-10}$ aryl,
or when Y is $NR^hR^i$, and $R^h$ is hydrogen, then $R^i$ and A may be linked together to form the group —$CH_2(CH_2)_q CH_2$—;
$Q^1$ is $C_{0-3}$ alkyl;
$R^1$ is aryl selected from the group consisting of phenyl and napthyl,
wherein said aryl is unsubstituted or substituted with one or more
(a) halo,
(b) —$C_{1-10}$ alkyl, wherein said alkyl is unsubstituted or substituted with one or more halo,
(c) —OH,
(d) —CN,
(e) —O—$C_{1-10}$ alkyl, or
(f) —$C_{3-12}$ cycloalkyl;
$R^2$ is
($R^4$—$SO_2$)N($R^7$)—, wherein $R^4$ is selected from the group consisting of
(a) —$C_{1-10}$ alkyl, or
(b) —$C_{3-12}$ cycloalkyl,
wherein said alkyl and cycloalkyl is unsubstituted or substituted with one or more
(i) halo,
(ii) —OH,
(iii) —CN,
(iv) —$C_{1-10}$ alkyl,
(v) —$C_{1-10}$ alkyl,
(v) —$C_{3-12}$ cycloalkyl,
(vi) aryl selected from the group consisting of phenyl and napthyl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thiophenyl, triazolyl, oxazolyl, isoxazolyl, thiazolyl, oxadiazolyl, indolyl, quinolinyl, isoquinolinyl, benzimidazolyl, benzofuranyl, and benzoxazolyl,
and said aryl and heteroaryl is unsubstituted or substituted with one or more
(A) halo,
(B) —OH,
(C) —CN,
(D) —O—$C_{1-10}$ alkyl,
(E) —$C_{3-12}$ cycloalkyl, or
(F) —$C_{1-10}$ alkyl; and $R^7$ is selected from the group consisting of
(a) hydrogen,
(b) —$C_{1-10}$ alkyl,
(c) aryl selected from the group consisting of phenyl and napthyl, and
(d) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thiophenyl, triazolyl, oxazolyl, isoxazolyl, thiazolyl, oxadiazolyl, indolyl, quinolinyl, isoquinolinyl, benzimidazolyl, benzofuranyl, and benzoxazolyl,
wherein said alkyl, aryl and heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) aryl selected from the group consisting of phenyl and napthyl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thiophenyl, triazolyl, oxazolyl, isoxazolyl, thiazolyl, oxadiazolyl, indolyl, quinolinyl, isoquinolinyl, benzimidazolyl, benzofuranyl, and benzoxazolyl,
wherein said alkyl, cycloalkyl, aryl or heteroaryl is unsubstituted or substituted with one or more
(A) halo,
(B) —OH,
(C) —CN,
(D) —O—$C_{1-10}$ alkyl,
(E) —$C_{3-12}$ cycloalkyl, or
(F) aryl selected from the group consisting of phenyl and napthyl;
$R^3$ is

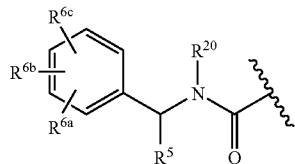

wherein $R^5$ is $C_{1-10}$ alkyl, wherein said alkyl is unsubstituted or substituted with one or more halogen;
$R^{6a}$, $R^{6b}$, and $R^{6c}$ are independently selected from the group consisting of:
(1) hydrogen,
(2) halo,
(3) —$C_{1-10}$ alkyl,
(4) —OH,
(5) —CN,
(6) —$C_{3-12}$ cycloalkyl, and
(7) —O—$C_{1-10}$ alkyl;
$R^{20}$ is selected from the group consisting of
(1) hydrogen, and
(2) $C_{1-10}$ alkyl;

and pharmaceutically acceptable salts thereof, and enantiomers and diastereomers thereof.

2. A compound of claim 1 wherein $R^1$ is phenyl and $Q^1$ is $CH_2$.

3. A compound of claim 1 wherein Y is $NH_2$.

4. A compound of claim 1 wherein A is unsubstituted $C_{1-6}$ alkyl.

5. A compound of claim 1 which is a compound of formula (II)

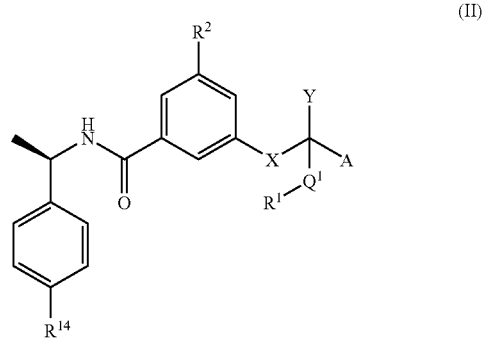

and pharmaceutically acceptable salts thereof, and enantiomers and diastereomers thereof, wherein A, $Q^1$, X, Y, $R^1$ and $R^2$ are as defined in claim 1, and $R^{14}$ is selected from the group consisting of:
(1) hydrogen,
(2) halogen, and
(3) $C_{1-10}$ alkyl.

6. A compound of claim 5 wherein $R^{14}$ is halogen.

7. A compound of claim 5 wherein $R^1$ is phenyl and $Q^1$ is $CH_2$.

8. A compound of claim 1 which is a compound of formula (III)

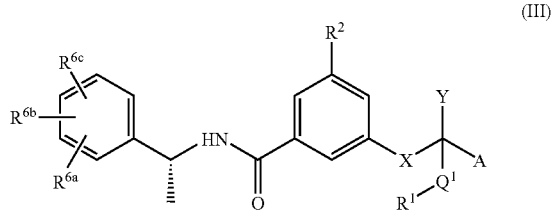

and pharmaceutically acceptable salts thereof, and enantiomers and diastereomers thereof, wherein A, $Q^1$, X, Y, $R^1$, $R^2$, $R^{6a}$, $R^{6b}$ and $R^{6c}$ are defined in claim 1.

9. A pharmaceutical composition comprising a therapeutically effective amount of a compound of claim 1 or a pharmaceutically acceptable salt thereof and a pharmaceutically acceptable carrier.

10. A method for treating Alzheimer's disease in a patient in need thereof comprising administering to the patient a therapeutically effective amount of a compound of claim 1 or a pharmaceutically acceptable salt thereof.

11. A compound of claim 1 which is selected from the group consisting of
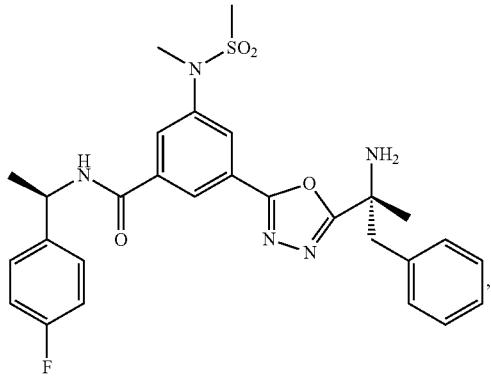
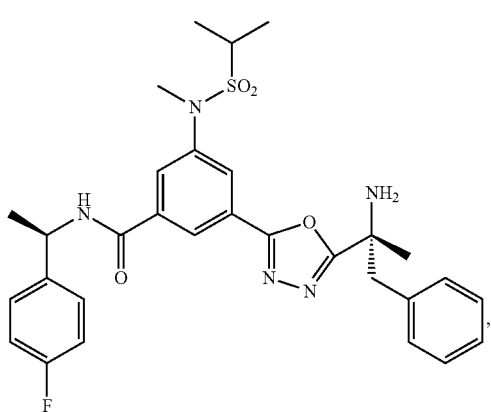
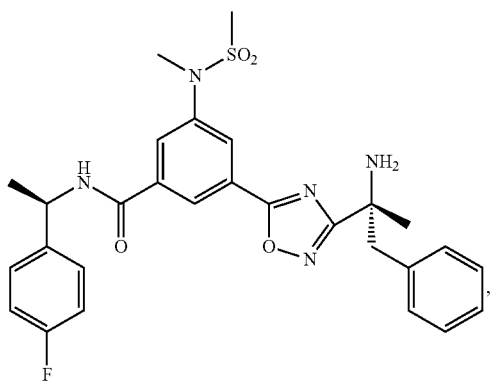
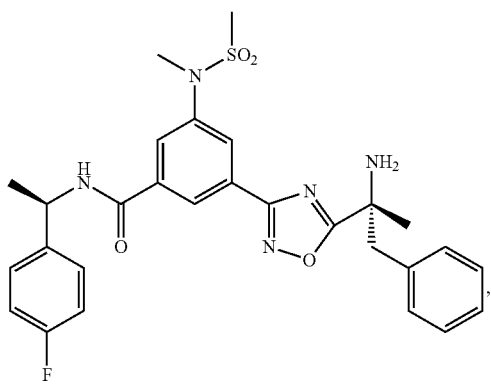
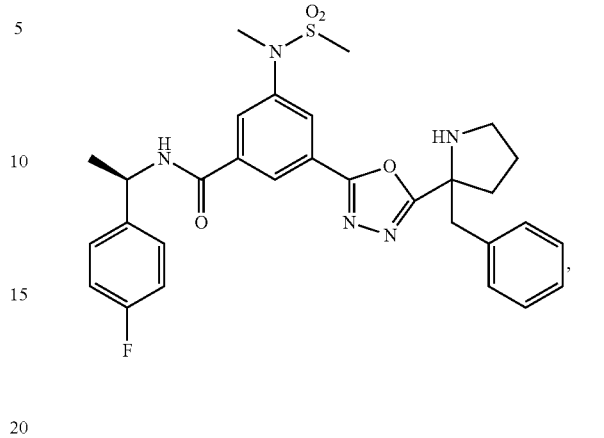
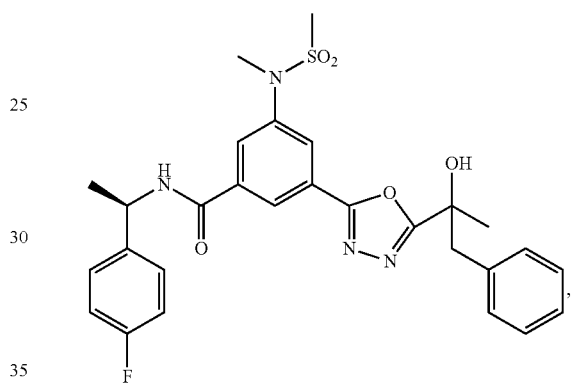
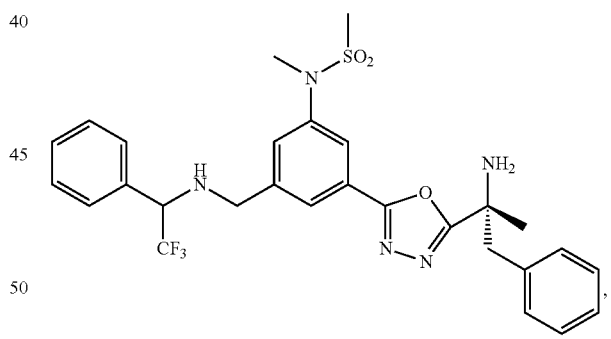
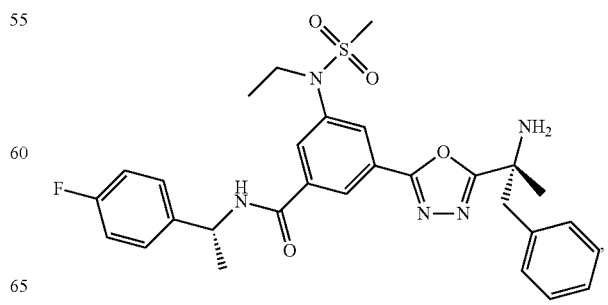

-continued
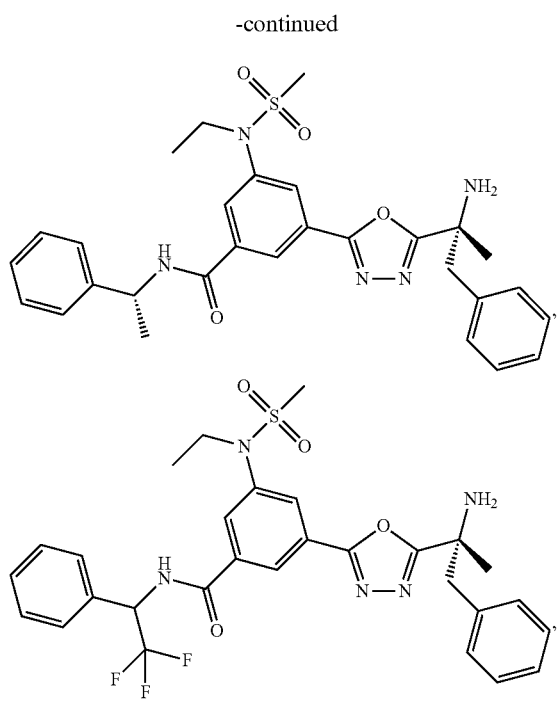
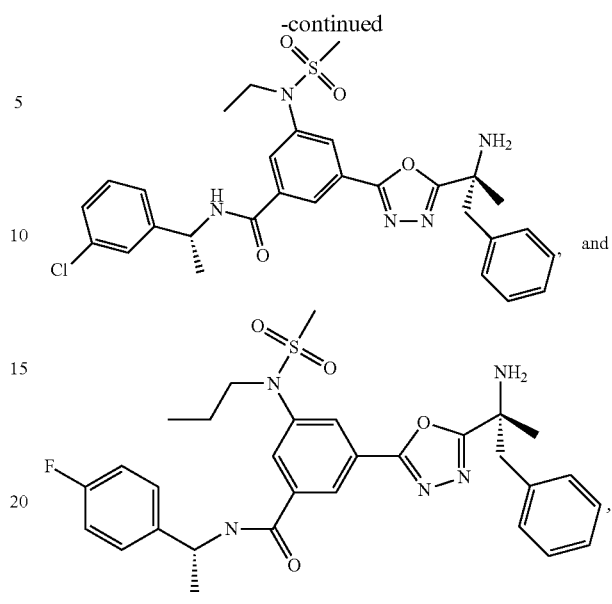
or a pharmaceutically acceptable salt thereof.
* * * * *